United States Patent
Weidner-Wells et al.

(10) Patent No.: US 6,518,285 B2
(45) Date of Patent: Feb. 11, 2003

(54) PIPERIDINYLOXY AND PYRROLIDINYLOXY OXAZOLIDINONE ANTIBACTERIALS

(75) Inventors: Michele A. Weidner-Wells, Hillsborough, NJ (US); Christine Boggs, High Bridge, NJ (US); Dennis Hlasta, Doylestown, PA (US); Erin Nelson, Hillsborough, NJ (US)

(73) Assignee: Ortho McNeil Pharmaceutical, Inc., Raritan, NJ (US)

(*) Notice: Subject to any disclaimer, the term of this patent is extended or adjusted under 35 U.S.C. 154(b) by 0 days.

(21) Appl. No.: 09/729,342

(22) Filed: Dec. 5, 2000

(65) Prior Publication Data

US 2002/0103377 A1 Aug. 1, 2002

Related U.S. Application Data

(60) Provisional application No. 60/172,923, filed on Dec. 21, 1999.

(51) Int. Cl.[7] .................. A61K 31/445; C07D 413/10
(52) U.S. Cl. .................. 514/326; 514/210; 514/256; 514/336; 514/376; 544/335; 546/209; 546/256; 548/229; 548/950
(58) Field of Search .................. 514/210, 256, 514/326, 336, 376; 544/335; 546/209, 256; 548/229, 950

(56) References Cited

U.S. PATENT DOCUMENTS

| | | |
|---|---|---|
| 4,705,799 A | 11/1987 | Gregory |
| 5,565,571 A | 10/1996 | Barbachyn et al. |
| 5,654,428 A | 8/1997 | Barbachyn et al. |
| 5,792,765 A | 8/1998 | Riedle et al. |
| 5,827,857 A | 10/1998 | Riedl et al. |
| 5,837,870 A | 11/1998 | Pearlman et al. |
| 5,883,093 A | 3/1999 | Hutchinson et al. |
| 5,910,504 A | 6/1999 | Hutchinson |
| 5,929,248 A | 7/1999 | Barbachyn et al. |
| 6,090,820 A | 7/2000 | Barbachyn et al. |
| 6,124,334 A | 9/2000 | Hutchinson |

FOREIGN PATENT DOCUMENTS

| | | |
|---|---|---|
| EP | 127902 | 12/1984 |
| EP | 738726 | 10/1996 |
| JP | 11/322729 | 11/1999 |
| WO | WO93/09103 | 5/1993 |
| WO | WO95/07271 | 6/1995 |
| WO | WO96/15130 | 5/1996 |
| WO | WO96/23788 | 8/1996 |
| WO | WO96/35691 | 11/1996 |
| WO | WO98/54161 | 12/1998 |
| WO | WO99/10342 | 3/1999 |
| WO | WO99/12914 | 3/1999 |
| WO | WO 00/27830 * | 5/2000 |
| WO | WO27830 | 5/2000 |

OTHER PUBLICATIONS

Thornber "Isosterism and molecular modification in drug design" Chem. Sci. Rev. v.8(40 p. 563–580 (1979).*
Gregory et al. "Antibacterials. synthesis and structure–activity studies of 3–aryl–2–oxooxazolidines. the B group" J. Med. Chem. v 32 p. 1673–1661 (1989).*
International Search Report No. PCT/US00/33835 dated Mar. 14, 2001.

* cited by examiner

*Primary Examiner*—Ceila Chang

(57) ABSTRACT

Piperidinyloxy, pyrrolidinyloxyl and azetidinyloxy compounds of the formula:

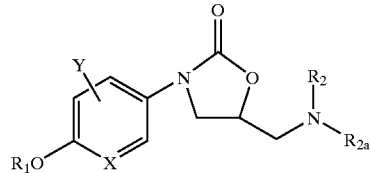

wherein $R_1$ is a piperidinyl, pyrrolidinyl or azetidinyl moiety as described herein and in which the substituents have the meaning indicated in the description. These compounds are useful as antibacterial agents.

25 Claims, No Drawings

PIPERIDINYLOXY AND PYRROLIDINYLOXY OXAZOLIDINONE ANTIBACTERIALS

This application claims the benefit under 35 U.S.C. §119(e) of prior application Ser. No. 60/172,923, filed Dec. 21, 1999.

FIELD OF THE INVENTION

The present invention relates to the field of piperidinyloxy, pyrrolidinyloxy and azetidinyloxy oxazolidinone compounds having antibacterial activity, pharmaceutical compositions containing the compounds, and methods of treating bacterial infections with the compounds.

BACKGROUND OF THE INVENTION

Oxazolidinones have been identified, within the last twenty years, as a new class of antibacterials which are active against numerous multidrug-resistant gram positive organisms. Particularly problematic pathogens include methicillin-resistant *Staphylococcus aureus* (MRSA), vancomycin-resistant enterococci (VRE) and penicillin- and cephalosporin-resistant *Streptococcus pneumoniae*. As a class oxazolidinones exhibit a unique mechanism of action. Studies have shown that these compounds selectively bind to the 50S ribosomal subunit and inhibit bacterial translation at the initiation phase of protein synthesis. Exemplary members of oxazolidinones are linezolid (see WO 95/07271) and eperezolid.

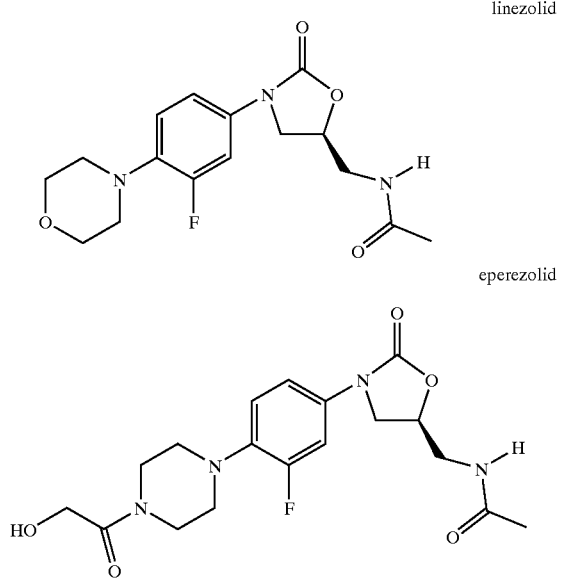

The following references relate to various oxazolidinone type compounds disclosed as having antibacterial activity:

U.S. Pat. No. 4,705,799 to W. A. Gregory discloses aminomethyl oxooxazolidinyl benzene derivatives, including the sulfides, sulfoxides, sulfones and sulfonamides, such as (1)-N-[3-[4-(methylsulfinyl)-phenyl]-2-oxooxazolidin-5-ylmethyl]acetamide.

U.S. Pat. No. 5,565,571 to Barbachyn et al. discloses substituted aryl- and heteroarylphenyloxazolidinones.

U.S. Pat. No. 5,792,765 to Riedl et al. relates to new substituted oxazolidinones.

U.S. Pat. No. 5,910,504 to Hutchinson discloses phenyloxazolidinone compounds having a nitrogen containing hetero-aromatic ring substitution attached through one of the nitrogen atoms.

WO 93/09103 (Barbachyn et al.) discloses substituted aryl- and heteroarylphenyloxazolidinones.

WO 95/07271 (Barbachyn et al.) discloses oxazine and thiazine oxazolidinone derivatives.

WO 98/54161 (Hester et al.) provides oxazolidinone antibacterial agents having a thiocarbonyl functionality.

SUMMARY OF THE INVENTION

The invention provides new piperidinyloxy, pyrrolidinyloxy and azetidinyloxy compounds of Formula I

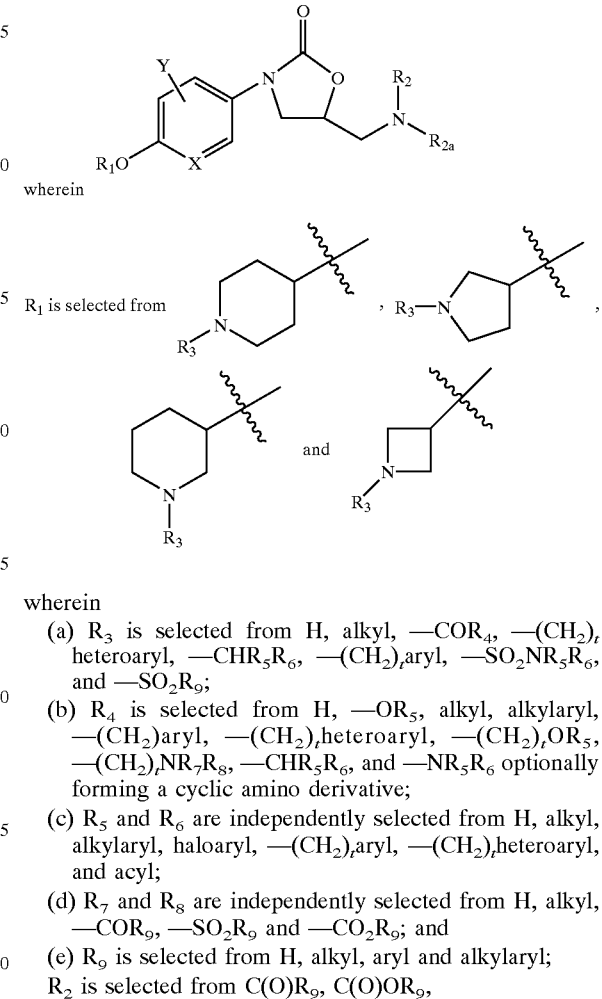

wherein (a) $R_3$ is selected from H, alkyl, —$COR_4$, —$(CH_2)_t$heteroaryl, —$CHR_5R_6$, —$(CH_2)_t$aryl, —$SO_2NR_5R_6$, and —$SO_2R_9$;

(b) $R_4$ is selected from H, —$OR_5$, alkyl, alkylaryl, —$(CH_2)$aryl, —$(CH_2)_t$heteroaryl, —$(CH_2)_tOR_5$, —$(CH_2)_tNR_7R_8$, —$CHR_5R_6$, and —$NR_5R_6$ optionally forming a cyclic amino derivative;

(c) $R_5$ and $R_6$ are independently selected from H, alkyl, alkylaryl, haloaryl, —$(CH_2)_t$aryl, —$(CH_2)_t$heteroaryl, and acyl;

(d) $R_7$ and $R_8$ are independently selected from H, alkyl, —$COR_9$, —$SO_2R_9$ and —$CO_2R_9$; and (e) $R_9$ is selected from H, alkyl, aryl and alkylaryl;

$R_2$ is selected from $C(O)R_9$, $C(O)OR_9$, $R_{2a}$ is H or acyl with the proviso that when $R_3$ is selected from alkyl, —$(CH_2)_t$aryl, —$(CH_2)_t$heteroaryl, and —$CHR_5R_6$, $R_{2a}$ is H;

X is N or CH;

Y is selected from H, halogen, alkoxy, and alkyl; and t is an integer of 0 to 4;

or an optical isomer, enantiomer, diastereomer, racemate or racemic mixture thereof, or a pharmaceutically acceptable salt thereof.

Compounds of the above formula are useful as antibacterial agents for the treatment of bacterial infections in a subject such as human and animal.

The present invention is also directed to a method of treating a subject having a condition caused by or contributed to by bacterial infection, which comprises administering to said subject a therapeutically effective amount of the compound of Formula I.

The present invention is further directed to a method of preventing a subject from suffering from a condition caused by or contributed to by bacterial infection, which comprises administering to the subject a prophylactically effective amount of the compound of Formula I.

Other objects and advantages will become apparent to those skilled in the art from a review of the ensuing specification.

DETAILED DESCRIPTION

Relative to the above description, certain definitions apply as follows.

Unless otherwise noted, under standard nomenclature used throughout this disclosure the terminal portion of the designated side chain is described first, followed by the adjacent functionality toward the point of attachment.

Unless specified otherwise, the terms "alkyl", "alkenyl", and "alkynyl," whether used alone or as part of a substituent group, include straight and branched chains having 1 to 8 carbon atoms, or any number within this range. For example, alkyl radicals include methyl, ethyl, n-propyl, isopropyl, n-butyl, isobutyl, sec-butyl, t-butyl, n-pentyl, 3-(2-methyl) butyl, 2-pentyl, 2-methylbutyl, neopentyl, n-hexyl, 2-hexyl and 2-methylpentyl. "Alkoxy" radicals are oxygen ethers formed from the previously described straight or branched chain alkyl groups. "Cycloalkyl" groups contain 3 to 8 ring carbons and preferably 5 to 7 ring carbons. The alkyl group and alkoxy group may be independently substituted with one or more members of the group including, but not limited to, mono-, di-, tri-, or per-halogen, alkyl, alkoxy, aryl, heteroaryl, heterocyclyl, amino, substituted amino, OH, CN, mercapto, nitro, and $C_{1-8}$ acyloxy.

The term "acyl" as used herein, whether used alone or as part of a substituent group, means an organic radical having 2 to 6 carbon atoms (branched or straight chain) derived from an organic acid by removal of the hydroxyl group.

The term "Ac" as used herein means acetyl.

The term "halo" or "halogen" means fluoro, chloro, bromo and iodo. (Mono-di-, tri-, and per-)halo-alkyl is an alkyl radical substituted by independent replacement of the hydrogen atoms thereon with halogen.

"Aryl" or "Ar," whether used alone or as part of a substituent group, is a carbocyclic aromatic radical including, but not limited to, phenyl, 1- or 2-naphthyl and the like. The carbocyclic aromatic radical may be substituted by independent replacement of 1 to 3 of the hydrogen atoms thereon with halogen, —OH, —CN, mercapto, nitro, amino, substituted amino, alkyl, —O-alkyl, —S-alkyl, —NH-alkyl, —N(alkyl)$_2$, (mono-, di-, tri-, and per-)halo-alkyl, formyl, —COR$_5$, —COOR$_5$, —CONHR$_5$, —CONR$_5$R$_6$, —SOR$_5$, —SO$_2$R$_5$, —SO$_2$NHR$_5$, —SO$_2$NR$_5$R$_6$, alkyl-COO, alkyl-CONH, or carboxamide, wherein R$_5$ and R$_6$ are defined as hereinabove. Illustrative aryl radicals include, for example, phenyl, naphthyl, diphenyl, fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, tolyl, xylyl, dimethylcarbamylphenyl and the like. "Ph" or "PH" denotes phenyl.

Whenever the term "alkyl", "acyl", or "aryl" or either of their prefix roots appear in a name of a substituent (e.g., aralkyl, dialkylamino) it shall be interpreted as including those limitations given above for "alkyl", "acyl", and "aryl." Designated numbers of carbon atoms (e.g., $C_{1-8}$) shall refer independently to the number of carbon atoms in an alkyl or cycloalkyl moiety or to the alkyl portion of a larger substituent in which alkyl appears as its prefix root.

Whether used alone or as part of a substituent group, "heteroaryl" refers to a cyclic aromatic radical having from five to ten ring atoms of which one ring atom is selected from S, O, and N; 0–2 ring atoms are additional heteroatoms independently selected from S, O, and N; and the remaining ring atoms are carbon. The radical being joined to the rest of the molecule via any of the ring atoms, for example, pyridinyl, pyrazinyl, pyrimidinyl, pyrroyl, pyrazolyl, imidazolyl, thiazolyl, oxazolyl, isoxazolyl, thiadiazolyl, triazolyl, oxadiazolyl, thienyl, furanyl, quinolinyl, isoquinolinyl, and the like. The heteroaryl group may be substituted by independent replacement of 1 to 3 of the hydrogen atoms thereon with halogen, —OH, —CN mercapto, nitro, amino, substituted amino, alkyl, —O-alkyl, —S-alkyl, —NH-alkyl, —N(alkyl)$_2$, (mono-, di-, tri-, and per-)halo-alkyl, formyl, —COR$_5$, —COOR$_5$, —CONHR$_5$, —CONR$_5$R$_6$, —SOR$_5$, —SO$_2$RS, —SO$_2$NHR$_5$, —SO$_2$NR$_5$R$_6$, alkyl-COO, alkyl-CONH, or carboxamide, wherein R$_5$ and R$_6$ are defined as hereinabove. Heteroaryl may also be substituted with a mono-oxo to give 4-oxo-1H-quinoline and the like.

A "cyclic amino" derivative is a 4 to 8 membered nitrogen containing cyclic group where the other remaining members are selected from carbon, nitrogen, oxygen or sulfur, for instance an azetidinyl group, pyrrolidinyl group, piperidinyl group, morpholino group, piperazinyl, or groups of the following formulae:

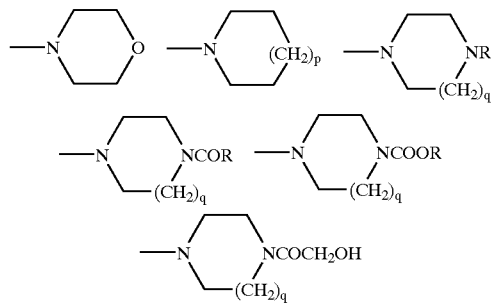

wherein p is -2 to 4 and q is 1–4.

"Heterocyclyl" or "heterocycle" is a 3- to 8-member saturated or partially saturated single or fused ring system which consists of carbon atoms and from one to three heteroatoms selected from N, O and S. The heterocyclyl group may be attached at any heteroatom or carbon atom, which results in the creation of a stable structure. Examples of heterocyclyl groups include, but are not limited to pyridine, pyrimidine, oxazoline, pyrrole, imidazole, morpholine, furan, indole, benzofuran, pyrazole, pyrrolidine, piperidine, and benzimidazole. "Heterocyclyl" or "heterocycle" may be substituted with one or more independent groups including, but not limited to, H, halogen, oxo, OH, alkyl, substituted alkyl, amino, substituted amino, carboxyl, alkylcarboxyl, and alkoxy.

Unless specified otherwise, it is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The compounds of the instant invention are asymmetric in the oxazolidinone ring at the 5-position and thus exist as optical antipodes. As such, all possible optical antipodes, enantiomers or diastereomers resulting from additional asymmetric centers that may exist in optical antipodes, racemates and Aft racemic mixtures thereof are also part of this invention. The antipodes can be separated by methods known to those skilled in the art such as, for example, fractional recrystallization of diastereomeric salts of enantiomerically pure acids. Alternatively, the antipodes can be separated by chromatography on a Pirkle column.

The phrase "a pharmaceutically acceptable salt" denotes salts of the free base which possess the desired pharmacological activity of the free base and which are neither biologically nor otherwise undesirable. These salts may be derived from inorganic or organic acids. Examples of inorganic acids are hydrochloric acid, nitric acid, hydrobromic acid, sulfuric acid, or phosphoric acid. Examples of organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicyclic acid and the like. Suitable salts are furthermore those of inorganic or organic bases, such as KOH, NaOH, $Ca(OH)_2$, $Al(OH)_3$, piperidine, morpholine, ethylamine, triethylamine and the like.

Also included within the scope of the invention are the hydrated forms of the compounds which contain various amounts of water, for instance, the hydrate, hemihydrate and sesquihydrate forms.

The term "subject" includes, without limitation, any animal or artificially modified animal. As a particular embodiment, the subject is a human.

The term "drug-resistant" or "drug-resistance" refers to the characteristics of a microbe to survive in presence of a currently available antimicrobial agent such as an antibiotic at its routine, effective concentration.

The compounds described in the present invention possess antibacterial activity due to their novel structure, and are useful as antibacterial agents for the treatment of bacterial infections in humans and animals.

In particular, compounds of Formula I wherein X is CH are embodiments of the present invention for such purposes.

Compounds of Formula I wherein $R_2$ is $C(O)R_9$ wherein $R_9$ is as described above are particular embodiments of this invention.

More particularly, compounds of Formula I wherein $R_9$ is H or alkyl are also embodiments of this invention.

Compounds of Formula I wherein $R_1$

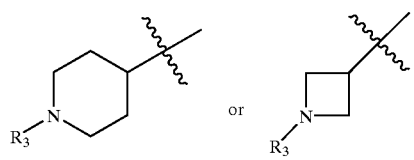

wherein $R_3$ is as described above are further particular embodiments of this invention.

More particularly, compounds of Formula I wherein $R_{2a}$ is H and $R_3$ is selected from $—COR_4$, $—SO_2R_9$ and $(CH_2)_t$ heteroaryl wherein $R_4$, $R_9$ and t are as described above are embodiments of this invention.

Still more particularly, compounds of Formula I wherein $R_4$ is selected from $OR_5$, $—(CH_2)_tOR_5$, alkyl, $—(CH_2)_t$aryl, and $—(CH_2)_t$heteroaryl wherein $R_5$ and t are as described above are embodiments of this invention.

The following are yet other particular embodiments of the present invention for such purposes:

(S)-N-[[3-[3-fluoro-4-{N-(benzyloxyacetyl)piperidinyl-4-oxy}phenyl]-2-oxo-5-oxazolidinyl]methyl] acetamide;

(S)-N-[[3-[3-fluoro-4-{N-(α-hydroxyacetyl)piperidinyl-4-oxy}phenyl]-2-oxo-5-oxazolidinyl]methyl] acetamide;

(S)-N-[[3-[3-fluoro-4-{N-(methanesulfonyl)piperidinyl-4-oxy}phenyl]-2-oxo-5-oxazolidinyl]methyl] acetamide;

(S)-N-[[3-[3-fluoro-4-{N-(methoxycarbonyl)piperidinyl-4-oxy}phenyl]-2-oxo-5-oxazolidinyl]methyl] acetamide;

(S)-N-[[3-[3-fluoro-4-{N-(2-pyrimidinyl)piperidinyl-4-oxy}phenyl]-2-oxo-5-oxazolidinyl]methyl]acetamide;

(S)-N-[[3-[3-fluoro-4-{N-(3-cyanobenzoyl)piperidinyl-4-oxy}phenyl]-2-oxo-5-oxazolidinyl]methyl] acetamide;

(S)-N-[[3-[3-fluoro-4-{N-(5-cyano-2-pyridyl) piperidinyl-4-oxy}phenyl]-2-oxo-5-oxazolidinyl] methyl]acetamide;

(S)-N-[[3-[3-fluoro-4-{N-(2-thienylcarbonyl)piperidinyl-4-oxy}phenyl]-2-oxo-5-oxazolidinyl]methyl] acetamide;

(S)-N-[[3-[3-fluoro-4-{N-(α-hyd roxyacetyl)piperidinyl-3-oxy}phenyl]-2-oxo-5-oxazolidinyl]methyl] acetamide; and (S)-N-[[3-[3-Fluoro-4-{N-(benzyloxyacetyl)pyrrolidinyl-3-oxy}phenyl]-2-oxo-5-oxazolidinyl]methyl] acetamide.

Finally, this invention provides a process for preparing a compound of Formula Ia Formula Ia

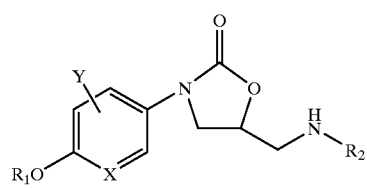

wherein R₁ is a moiety of the formula:

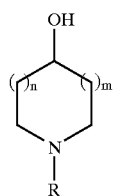

a wherein:

R is selected from Boc, —CH(Ph)₂ or —COCH₂OCH₂Ph, n is 0, 1 or 2, m is 0 or 1, and R₂, X, and Y are as described above, which process comprises:

(a) reacting a compound of Formula a with a compound of Formula a' or a" to form a compound of Formula b;

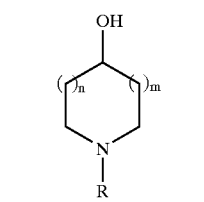

a

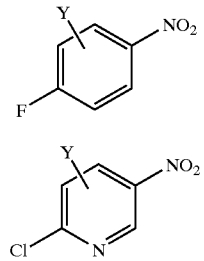

a' a"

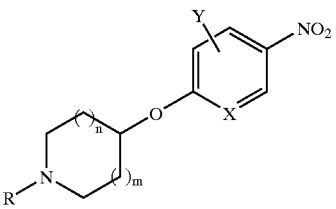

b

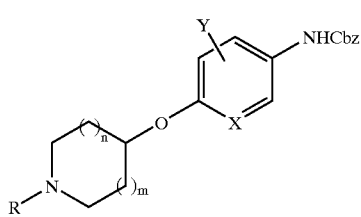

d (b) converting the compound of Formula b to a compound of Formula d;

(c) reacting the compound of Formula d with

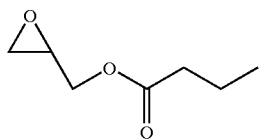

to form a compound of Formula e;

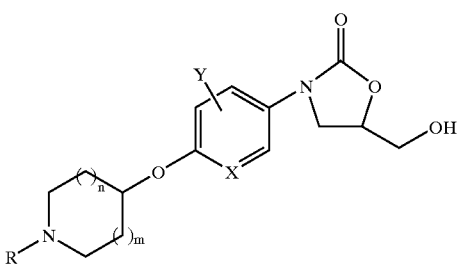

e

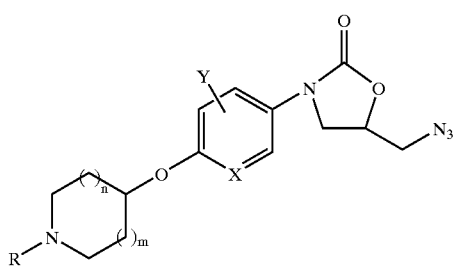

f (d) converting the compound of Formula e to a compound of Formula f;
(e) converting the compound of Formula f to a compound of Formula g;

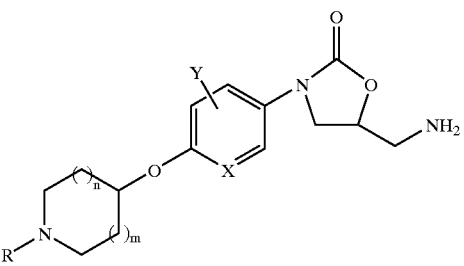

g

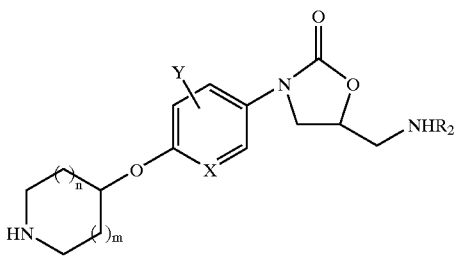

p (f) converting the compound of Formula g to a compound of Formula p; and
(g) converting the compound of Formula p to a compound of Formula Ia.

The compounds of Formula I may be prepared from readily available starting materials such as known oxazolidinone intermediates in accordance with synthetic methods well known in the art. The following are representative procedures outlined in Schemes I and II:

Scheme I
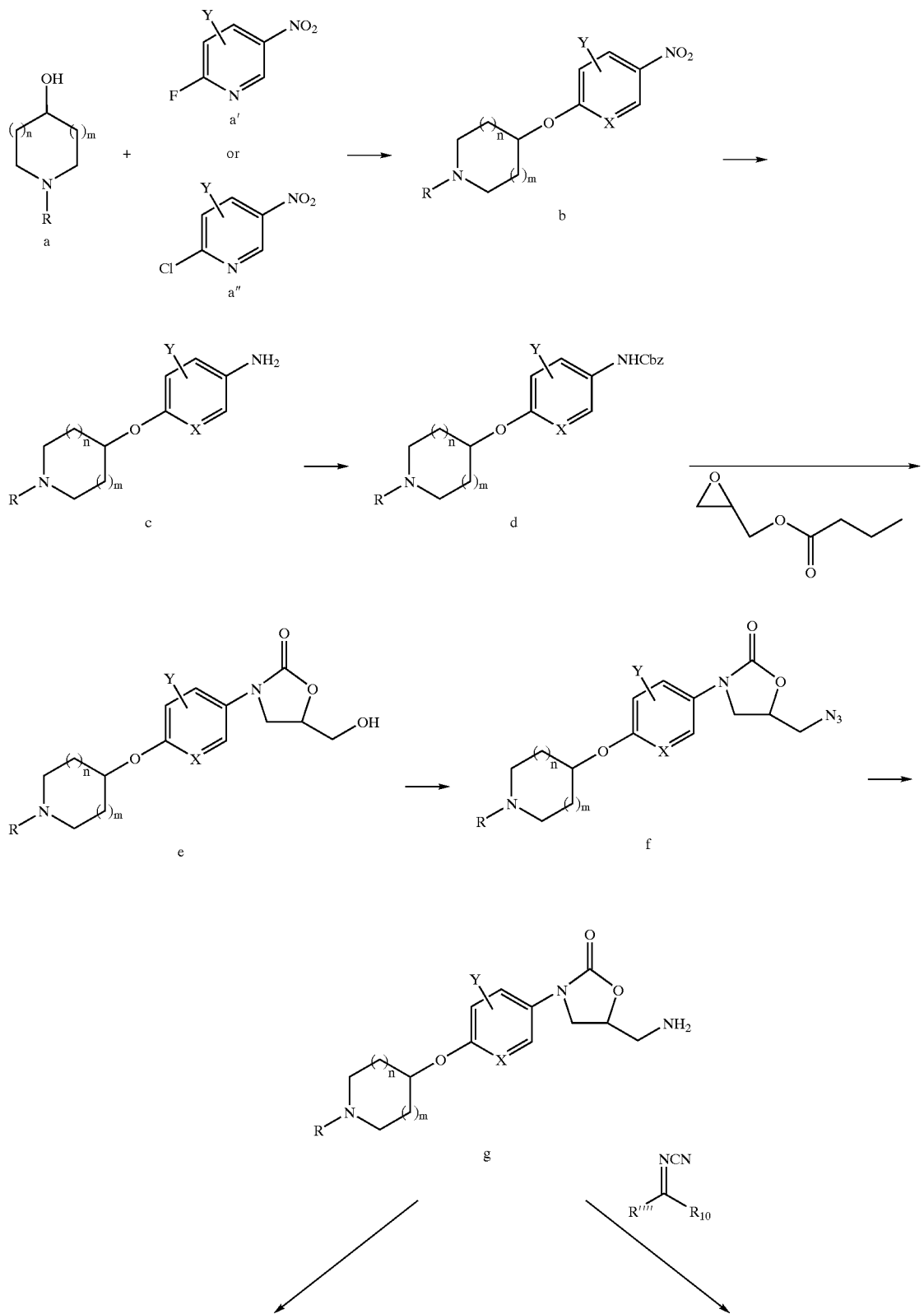

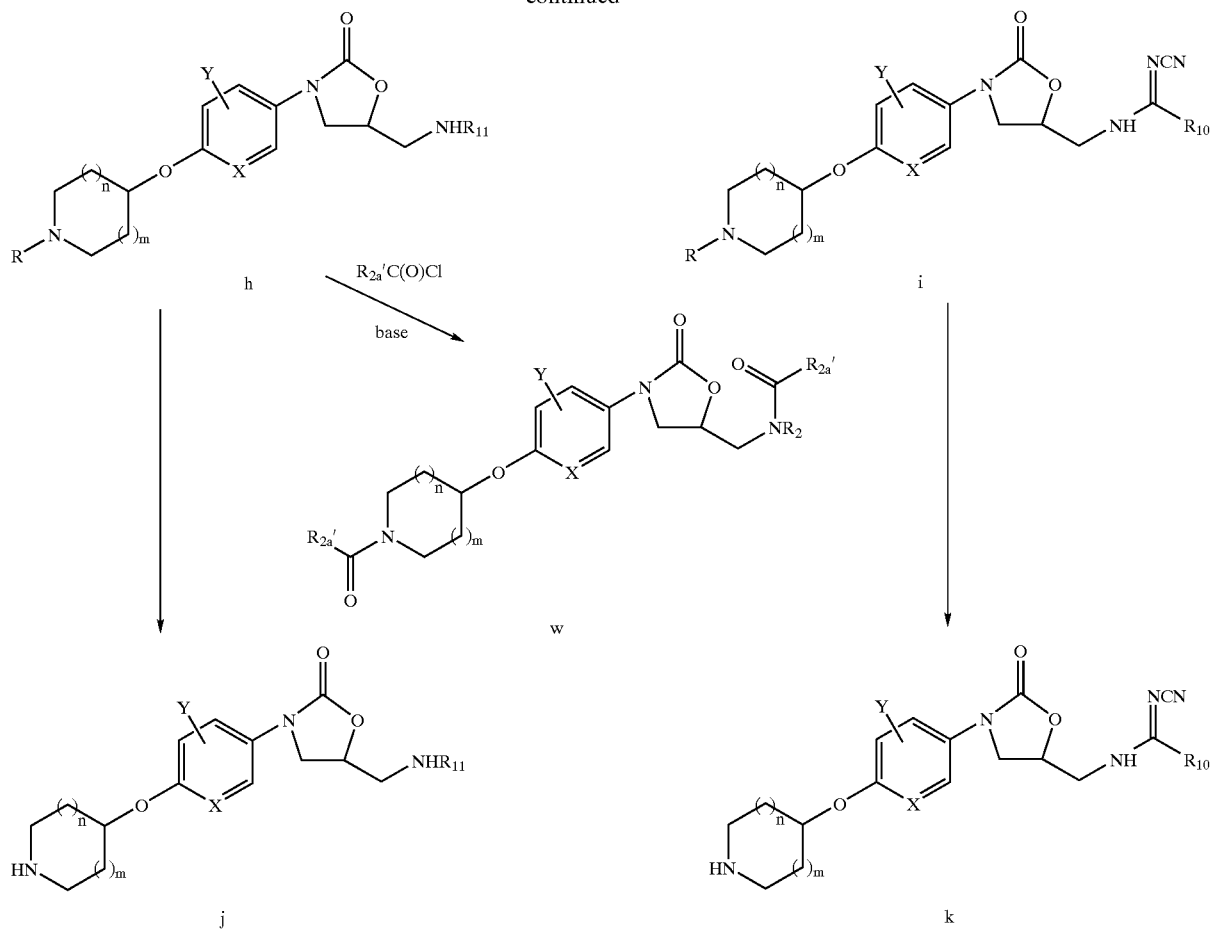

In accordance with Scheme I, wherein R is Boc, —CH(Ph)₂ or —COCH₂OCH₂Ph, $R_{11}$ is —COR₉ or —CO₂R₉, R' is any of the substituents on an aryl or heteroaryl group as described above, R" is selected from R₉ and —NR₅R₆, R'" is selected from alkyl, substituted alkyl and —CHR₅R₆, $R_{2a}'$ is optionally substituted alkyl, R"" is —SCH₃ or —OCH₃, $R_{10}$ is —NR₉R₉, R₉, —SR₉, or —NHR₉, n is 0, 1 or 2 and m is 0 or 1, and X, Y, R₄, R₅, R₆, R₉, and t are as described above, an appropriately substituted halo-nitrobenzene such as that of Formula a' or an appropriately substituted halo-nitropyridine such as that of Formula a" is added to a compound of Formula a (all of which are either commercially available or may be readily prepared by known methods) in acetone, dimethylformamide (DMF), or tetrahydrofuran (THF). The mixture is treated with an appropriate base such as potassium t-butoxide (KOtBu) to obtain the corresponding compound of Formula b. The compound of Formula b may be reduced to the corresponding compound of Formula c under appropriate conditions such as H₂, Pd/C and ethanol (EtOH) or NH₄OCOH, Pd/C and methanol (MeOH). Then compound c is treated with benzylchloroformate (CbzCl) in the presence of an appropriate base such as cesium carbonate (CsCO₃) in an appropriate solvent such as THF, H₂O or acetone to obtain the corresponding compound of Formula d. Compound d is then treated with an appropriate base such as nBuLi, followed by addition of glycidyl butyrate in an appropriate solvent such as THF to obtain the corresponding compound of Formula e. The compound of Formula e is treated with methanesulfonyl chloride (MsCl) and an appropriate base such as triethylamine (NEt₃) in an appropriate solvent such as methylene chloride (CH₂Cl₂). After standard workup, sodium azide (NaN₃) is then added into the mixture in an appropriate solvent such as dimethylformamide (DMF) and heated at a preferred temperature range of 70° C. to 90° C. to obtain the corresponding compound of Formula f. The compound of Formula f may be reduced under appropriate conditions such as H₂ and Pd/C in an appropriate solvent such as ethyl acetate (EtOAc), or the compound of Formula f may be reduced using triphenylphosphine (PPh₃) and THF/H₂O to obtain the corresponding compound of Formula g.

The compound of Formula g can be treated with an appropriate acylating agent such as acetic anhydride (AC2O) or acetyl chloride (AcCl), along with an appropriate base such as pyridine or NEt₃ to give the corresponding compound of Formula h. The compound of Formula g can also be treated with an appropriate imidate to give the corresponding compound of Formula i. Compound h wherein R is —CH(Ph)₂ can be converted to the corresponding compound of Formula w by reacting with $R_{2a}'C(O)Cl$ in the presence of a base such as TEA. Compounds j and k can be obtained from compounds h and i, respectively, by deprotection with either trifluoroacetic acid (TFA) in an appropriate solvent such as CH₂Cl₂ or with Pd/C in an appropriate solvent such as EtOH or EtOAc.

Compounds of Formulae o, q, r, s, and u may be obtained in accordance with different routes as shown in Scheme II:

Scheme II

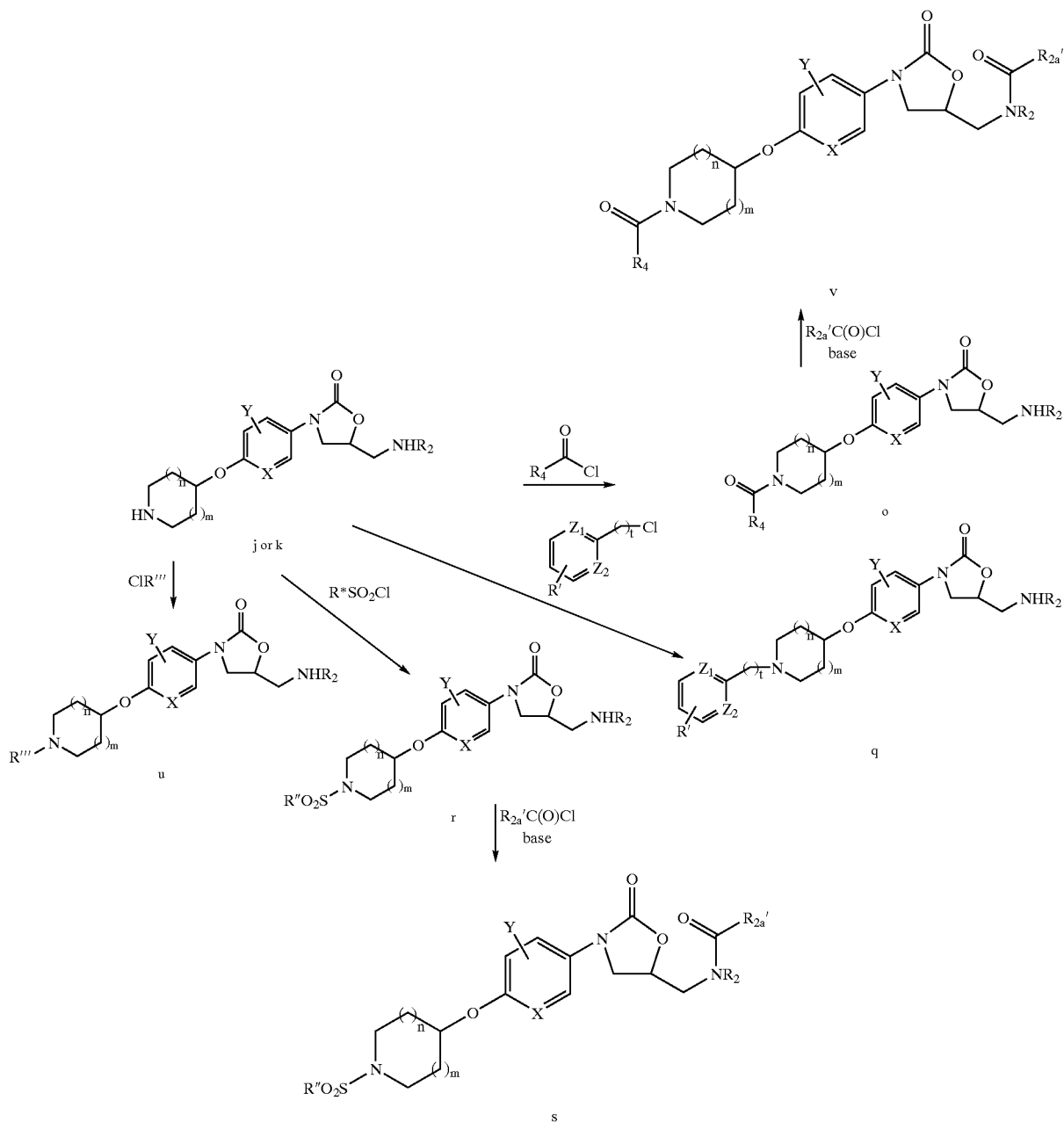

The compound of Formula j or k can be treated with an appropriate alkylating agent represented by ClR''' in the presence of an appropriate base such as NEt₃ in an appropriate solvent such as CH₂Cl₂ or THF to obtain the corresponding compound of Formula u. Alternatively, the compound of Formula j or k can be treated with an appropriate sulfonyl chloride represented by R''SO₂Cl such as MsCl in the presence of an appropriate base such as NEt₃ in an appropriate solvent such as CH₂Cl₂ or THF to obtain the corresponding compound of Formula r. Still alternatively, the compound of Formula j or k can be treated with an appropriate alkylating agent represented by

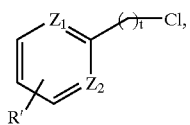

wherein $Z_1$ and $Z_2$ are independently N or CH, in the presence of an appropriate base such as NEt₃ in an appropriate solvent such as CH₂Cl₂ or THF to obtain the corresponding compound of Formula q. In addition, the compound of Formula j or k can also be treated with an appropriate acylating agent represented by R₄COCl such as AcCl in the presence of an appropriate base such as NEt₃ in an appropriate solvent such as $CH_2Cl_2$ or THF to obtain the corresponding compound of Formula o. In several cases, $R_4$ contains a protected amine or protected alcohols moiety. After removal of the protecting group, the resulting amine or alcohol can be further derivatized. Compounds of Formulae o and r can be converted to compounds of Formulae v and s, respectively, by reacting with $R_{2a}'C(O)Cl$ in the presence of a base such as TEA.

These compounds have antimicrobial activity against susceptible and drug resistant *S. aureus*, *S. epidermidis*, *S. pneumoniae*, *E. faecalis*, *E. faecium*, *Moraxella catarrhalis* and *H. influenzae*. These compounds are particularly useful against drug resistant Gram positive cocci such as methicillin-resistant staphylococci and vancomycin-resistant enterococci. These compounds are useful in the treatment of community-acquired pneumonia, upper and lower respiratory tract infections, skin and soft tissue infections, hospital-acquired lung infections, bone and joint infections, and other bacterial infections.

Minimal inhibitory concentration (MIC) has been an indicator of in vitro antibacterial activity widely used in the art. The in vitro antimicrobial activity of the compounds was determined by the microdilution broth method following the test method from the National Committee for Laboratory Standards (NCCLS). This method is described in the NCCLS Document M7-A4, Vol. 17, No. 2, "Methods for Dilution Antimicrobial Susceptibility Test for Bacteria that Grow Aerobically—Fourth Edition", which is incorporated herein by reference.

In this method two-fold serial dilutions of drug in cation adjusted Mueller-Hinton broth are added to wells in microdilution trays. The test organisms are prepared by adjusting the turbidity of actively growing broth cultures so that the final concentration of test organism after it is added to the wells is approximately $5\times10^4$ CFU/well.

Following inoculation of the microdilution trays, the trays are incubated at 35° C. for 16–20 hours and then read. The MIC is the lowest concentration of test is compound that completely inhibits growth of the test organism. The amount of growth in the wells containing the test compound is compared with the amount of growth in the growth-control wells (no test compound) used in each tray. As set forth in Table 1, compounds of the present invention were tested against a variety of Gram positive and Gram negative pathogenic bacteria resulting in a range of activities, from 1 to $\geq 128$ µg/mL depending on the organism tested.

TABLE 1

MIC Values of Some Compounds of Formula I

| Compound No. | MIC (µg/mL) E. faecium OC3312 | MIC (µg/mL) MRSA OC 2878 | MIC (µg/mL) S. aureus Broth | Compound No. | MIC (µg/mL) E. faecium OC3312 | MIC (µg/mL) MRSA OC 2878 | MIC (µg/mL) S. aureus Broth |
|---|---|---|---|---|---|---|---|
| 1 | >32 | 16 | 32 | 32 | 32 | 8 | 16 |
| 2 | 8 | 32 | 8 | 33 | 32 | 16 | 16 |
| 3 | 4 | 2 | 4 | 34 | >128 | 64 | 128 |
| 4 | 8 | 4 | 4 | 35 | 64 | 32 | 32 |
| 5 | 16 | 8 | 8 | 36 | 16 | 8 | 8 |
| 6 | 8 | 4 | 4 | 37 | 16 | 8 | 8 |
| 7 | 16 | 8 | 8 | 38 | 32 | 8 | 16 |
| 8 | 8 | 4 | 8 | 39 | 16 | 16 | 16 |
| 9 | 8 | 4 | 4 | 40 | 16 | 8 | 4 |
| 10 | 32 | 16 | 16 | 41 | >128 | 64 | 128 |
| 11 | 16 | 8 | 16 | 42 | >128 | 32 | 32 |
| 12 | 16 | 8 | 8 | 43 | >128 | 128 | 128 |
| 13 | 16 | 8 | 8 | 44 | 128 | 64 | 32 |
| 14 | 8 | 4 | 4 | 45 | 128 | 64 | 64 |
| 15 | 8 | 8 | 8 | 46 | >128 | 64 | 64 |
| 16 | 32 | 32 | 32 | 47 | >128 | 64 | 64 |
| 17 | 16 | 16 | 8 | 48 | >128 | 32 | 64 |
| 18 | 64 | 16 | 8 | 49 | >128 | 128 | >64 |
| 19 | 32 | 32 | 16 | 50 | >64 | 64 | >64 |
| 20 | 16 | 8 | 8 | 51 | 8 | 8 | 16 |
| 21 | 64 | 32 | 32 | 52 | 4 | 8 | 8 |
| 22 | 8 | 4 | 8 | 53 | 16 | 8 | 8 |
| 23 | 16 | 4 | 16 | 54 | 8 | 8 | 8 |
| 24 | 32 | 16 | 8 | 55 | 8 | 16 | 16 |
| 25 | 64 | 32 | 32 | 56 | 32 | 32 | 32 |
| 26 | 16 | 8 | 16 | 57 | 16 | 16 | 16 |
| 27 | 16 | 16 | 16 | 58 | 4 | 4 | 8 |
| 28 | 16 | 8 | 16 | 59 | 16 | 8 | 4 |
| 29 | 32 | 16 | 32 | 60 | >128 | 16 | 8 |
| 30 | 16 | 8 | 16 | 61 | 128 | 64 | 32 |
| 31 | 32 | 16 | 16 | | | | |

This invention further provides a method of treating bacterial infections, or enhancing or potentiating the activity of other antibacterial agents, in warm-blooded animals, which comprises administering to the animals a compound of the invention alone or in admixture with another antibacterial agent in the form of a medicament according to the invention.

When the compounds are employed for the above utility, they may be combined with one or more pharmaceutically acceptable carriers, e.g., solvents, diluents, and the like, and may be administered orally in such forms as tablets, capsules, dispersible powders, granules, or suspensions containing for example, from about 0.5% to 5% of suspending agent, syrups containing, for example, from about 10% to 50% of sugar, and elixirs containing, for example, from about 20% to 50% ethanol, and the like, or parenterally in the form of sterile injectable solutions or suspensions containing from about 0.5% to 5% suspending agent in an isotonic medium. These pharmaceutical preparations may contain, for example, from about 0.5% up to about 90% of the active ingredient in combination with the carrier, more usually between 5% and 60% by weight.

Compositions for topical application may take the form of liquids, creams or gels, containing a therapeutically effective concentration of a compound of the invention admixed with a dermatologically acceptable carrier.

In preparing the compositions in oral dosage form, any of the usual pharmaceutical media may be employed. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred. These active compounds may also be administered parenterally or intraperitoneally. Solutions or suspensions of these active compounds as a free base or pharmacological acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The effective dosage of active ingredient employed may vary depending on the particular compound employed, the mode of administration and the severity of the condition being treated. However, in general, satisfactory results are obtained when the compounds of the invention are administered at a daily dosage of from about 0.1 mg/kg to about 400 mg/kg of animal body weight, preferably given in divided doses two to four times a day, or in sustained release form. For most large mammals the total daily dosage is from about 0.07 g to 7.0 g, preferably from about 100 mg to 1000 mg. Dosage forms suitable for internal use comprise from about 100 mg to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The production of the above-mentioned pharmaceutical compositions and medicaments is carried out by any method known in the art, for example, by mixing the active ingredients(s) with the diluent(s) to form a pharmaceutical composition (e.g. a granulate) and then forming the composition into the medicament (e.g. tablets).

The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

EXAMPLE 1

(S)-N-[[3-[3-Fluoro-4-{N-(t-butoxycarbonyl)piperidinyl-4-oxy}phenyl]-2-oxo-5-oxazolidinyl]methyl]acetamide Compound 1

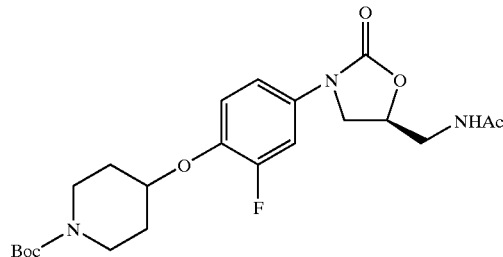

N-(t-Butoxycarbonyl)-4-piperidinol:

To a solution of 25 g (247 mmol) 4-piperidinol in 350 mL dry tetrahydrofuran (THF) at 0° C. was added dropwise 60.2 g (276 mmol) di-t-butylcarbonate in 350 mL dry THF. The reaction was allowed to warm to room temperature (rt) and stirred overnight. The solvent was removed under reduced pressure, the resulting residue dissolved in 700 mL $CH_2Cl_2$ and the solution extracted with $H_2O$ (1×400 mL), dried over $MgSO_4$, filtered and rotary evaporated to yield 45 g (91%) of N-(t-butoxycarbonyl)-4-piperidinol as an oil which slowly solidified to white crystals. $^1H$ NMR ($CDCl_3$) δ 3.75–3.96 (m, 3H); 2.92–3.13 (m, 2H); 1.80–1.93 (m, 4H); and 1.48 (s, 9H).

1-[N-(t-Butoxycarbonyl)piperidinyl-4-oxy]-2-fluoro-4-nitrobenzene:

To a solution of 740 mg (3.7 mmol) of N-(t-butoxycarbonyl)-4-piperidinol in 10 mL dry THF at 0° C. was added dropwise 4 mL (4.0 mmol) 1 M KOtBu. After stirring at 0° C. for 0.5 h, 0.40 mL (3.6 mmol) 3,4-difluoronitrobenzene was added and the reaction warmed to rt and stirred overnight. The reaction was poured into 100 mL $H_2O$ and extracted with $CH_2Cl_2$ (3×100 mL). The combined aqueous layers were washed with $H_2O$, dried with $MgSO_4$, filtered, and the solvent removed by rotary evaporation. Then the solid was triturated with cold hexanes to afford 1.1 g (89%) of 1-[N-(t-butoxycarbonyl)piperidinyl-4-oxy]-2-fluoro-4-nitrobenzene as a pale yellow solid; mp 88–90° C., MS (Cl) [M+Na]$^+$ 364.

1-[4-(N-t-Butoxycarbonyl)piperidinyl-4-oxy]-2-fluoro-4-aminobenzene:

To 1.78 g (5.23 mmol) of 1-[N-(t-butoxycarbonyl)piperidinyl-4-oxy]-2-fluoro-4-nitrobenzene in 100 mL MeOH was added 1.05 g (16.6 mmol) ammonium formate and 70 mg 10% Pd/C and the reaction heated at reflux under $N_2$ for 2 h. The reaction was filtered through a pad of celite and the filtrate evaporated to afford crude aniline as a gold oil. The material was used without further purification in the next step. 2-Fluoro-1-{N-(t-butoxycarbonyl)piperid inyl-4-oxy}4-(phenylmethoxycarbonylamino)benzene:

To 1-[4-(N-t-butoxycarbonyl)piperidinyl-4-oxy]-2-fluoro-4-aminobenzene (5.23 mmol) in 150 mL 2:1 acetone:$H_2O$ at 0° C. was added 1.03 g (12.3 mmol) $NaHCO_3$ and 0.90 mL (6.30 mmol) benzylchloroformate. After stirring at rt for 6 h the volatiles were evaporated, the residue diluted with 300 mL $H_2O$ and extracted with $Et_2O$ (3×150 mL). The combined organic layers were washed with $H_2O$, dried over $MgSO_4$, filtered, and the solvent removed by rotary evaporation. Silica gel chromatography (20% EtOAc in Hexanes) afforded 2.06 g (89%) of 2-fluoro-1-{N-(t-butoxycarbonyl)piperidinyl-4-oxy}-4-(phenylmethoxycarbonylamino)benzene as a yellow, waxy solid. $^1H$ NMR ($CDCl_3$) δ 7.3–7.4 (m, 6H); 6.9–7.0 (m, 2H); 6.60 (brs, 1H); 4.3–4.4 (m, 1H); 3.7–3.8 (m, 2H); 3.2–3.3 (m, 2H); 1.6–1.8 (m, 2H); and 1.48 (s, 9H).

(R)-[3-[3-Fluoro-4-{N-(t-butoxycarbonyl)piperidinyl-4-oxy}phenyl]-2-oxo-5-oxazolidinyl]methanol:

To 1.73 g (3.89 mmol) of 2-fluoro-1-{N-(t-butoxycarbonyl)piperidinyl-4-oxy}-4-(phenylmethoxycarbonylamino)benzene in 25 mL dry THF at −78° C. was added 2 mL (5.0 mmol) 2.5M n-BuLi and the reaction stirred for 1 h. Then 0.71 mL (5.01 mmol) (R)-glycidyl butyrate was added via syringe and the reaction warmed to rt and stirred overnight. The reaction was carefully poured into 150 mL sat. $NH_4Cl$ (aq.) and extracted with EtOAc (3×100 mL). The combined organic layers were washed with $H_2O$, dried over $MgSO_4$, filtered, and the solvent removed by rotary evaporation. Silica gel chromatography (40% EtOAc in hexanes to 70% EtOAc in hexanes) gave 1.15 g (72%) of (R)-[3-[3-fluoro-4-{N-(t-butoxycarbonyl)piperidinyl-4-oxy}phenyl]-2-oxo-5-oxazolidinyl]methanol as a white solid; mp 110–111° C., MS (Cl) [M+Na]$^+$ 433.5.

(R)-[3-[3-Fluoro-4-{N-(t-butoxycarbonyl)piperidinyl-4-oxy}phenyl]-2-oxo-5-oxazolidinyl]methyl Methanesulfonate:

To 1.03 g (2.51 mmol) of (R)-[3-[3-fluoro-4-{N-(t-butoxycarbonyl)piperidinyl-4-oxy}phenyl]-2-oxo-5-oxazolidinyl]methanol in 50 mL $CH_2Cl_2$ at 0° C. was added 0.70 mL (5.02 mmol) $NEt_3$ and 0.37 mL (4.78 mmol) methanesulfonyl chloride. After stirring for 3 h at 0° C. the reaction was poured into 75 mL $H_2O$ and extracted with $CH_2Cl_2$ (100 mL). The combined organic layers were washed with $H_2O$, dried over $MgSO_4$, filtered and the solvent removed by rotary evaporation to yield 1.21 g (99%) of (R)-[3-[3-fluoro-4-{N-(t-butoxycarbonyl)piperidinyl-4-oxy}phenyl]-2-oxo-5-oxazolidinyl]methyl methanesulfonate as a cream solid; mp 127–129° C., MS (Cl) [M+H-Boc]$^+$ 389.2.

(R)-[3-[3-Fluoro-4-{N-(t-butoxycarbonyl)piperdinyl-4-oxy}phenyl]-2-oxo-5-oxazolidinyl]methylazide:

To a solution of (R)-[3-[3-fluoro-4-{N-(t-butoxycarbonyl)piperidinyl-4-oxy}phenyl]-2-oxo-5-oxazolidinyl]methyl methanesulfonate (5.20 mmol) in 70 mL dimethylformamide (DMF) was added 1.22 g (18.8 mmol) sodium azide and the reaction heated at 75° C. overnight. Then the reaction was poured into 300 mL $H_2O$ and extracted with EtOAc (3×200 mL). The combined organic layers were washed with $H_2O$ (3×200 mL), dried over $MgSO_4$, filtered, and the solvent removed by rotary evaporation to yield 2.07 g (92%) of (R)-[3-[3-fluoro-4-{N-(t-butoxycarbonyl)piperidinyl-4-oxy}phenyl]-2-oxo-5-oxazolidinyl]methylazide as a beige solid. $^1H$ NMR ($CDCl_3$) δ 7.46 (dd, J=12.9 and 2.7 Hz, 1H); 7.14 (dt, J=5 8.9 and 1.4 Hz, 1H); 7.01 (t, J=8.9 Hz, 1H); 4.7–4.8 (m, 1H); 4.3–4.4 (m, 1H); 4.05 (t, J=8.9 Hz, 1H); 3.83 (dd, J=8.9 and 6.2 Hz, 1H); 3.7–3.8 (m, 2H); 3.71 (dd, J=13.2 and 4.6 Hz, 1H); 3.59 (dd, J=13.2 and 4.3 Hz, 1H); 3.2–3.3 (m, 2H); 1.8–2.0 (m, 2H); 1.7–1.8 (m, 2H); and 1.47 (s, 9H).

(S)-N-[[3-[3-Fluoro-4-{N-(t-butoxycarbonyl)piperidinyl-4-oxy}phenyl]-2-oxo-5-oxazolidinyl]methyl]acetamide (Compound 1):

To a solution of (R)-[3-[3-fluoro-4-{N-(t-butoxycarbonyl) piperidinyl4-oxy}phenyl]-2-oxo-5-oxazolidinyl] methylazide (5.20 mmol) in 9 mL dry THF was added 1.51 g (5.75 mmol) triphenylphosphine and the reaction stirred for 3 h at rt. Then 4.5 mL $H_2O$ was added and the reaction heated at 60° C. for 4 h. The volatiles were evaporated and the residue azeotroped with benzene (2×20 mL) to yield the crude amine.

To a solution of this crude amine in 100 mL EtOAc was added 0.58 mL (6.15 mmol) acetic anhydride and 1.2 mL (14.8 mmol) pyridine, and the reaction stirred at rt overnight. The reaction mixture was poured into 250 mL $H_2O$, extracted with EtOAc, dried over $MgSO_4$, filtered, and the solvent removed under reduced pressure. Silica gel chromatography (100% EtOAc to 5% MeOH in EtOAC) yielded 1.85 g (79%) of (S)-N-[[3-[3-fluoro-4-{N-(t-butoxycarbonyl)piperidinyl-4-oxy}phenyl]-2-oxo-5-oxazolidinyl]methyl]acetamide as a white solid; mp 179–180° C., MS (Cl) [M+Na]$^+$ 474.

EXAMPLE 2

(S)-N-[[3-[3-Fluoro-4-{piperidinyl-4-oxy}phenyl]-2-oxo-5-oxazolidinyl]methyl]acetamide

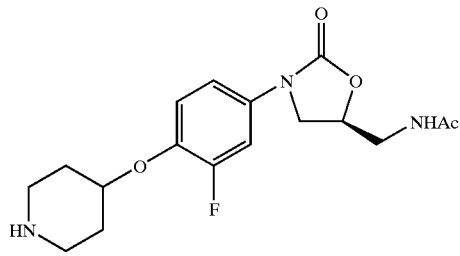

Compound 2

To a solution of 1.94 g (4.30 mmol) of Compound 1 in 225 mL $CH_2Cl_2$ was added 2.5 mL (32.5 mmol) trifluoroacetic acid (TFA) and the reaction stirred at rt for 6 h. The volatiles were evaporated under reduced pressure. The resulting oil (TFA salt) was dissolved in 100 mL $H_2O$, extracted with EtOAc (100 mL), and the aqueous layer was cooled to 0° C. and basicified with 1 N NaOH. This solution was extracted with EtOAc (5×200 mL), the combined extracts washed with brine, dried over $MgSO_4$, filtered, and evaporated under reduced pressure to yield (S)-N-[[3-[3-fluoro-4-{piperidinyl-4-oxy}phenyl]-2-oxo-5-oxazolidinyl]methyl] acetamide as a pale yellow glass; mp 55–59° C., MS (Cl) [M+H]$^+$ 352.

EXAMPLE 3

(S)-N-[[3-[3-Fluoro-4-{N-(benzyloxyacetyl)piperidinyl-4-oxy}phenyl]-2-oxo-5-oxazolidinyl]methyl]acetamide Compound 3

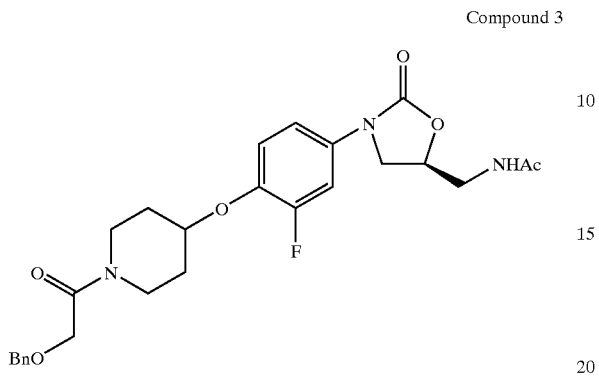

To a suspension of Compound 2 (1.50 mmol) in 50 mL CH$_2$Cl$_2$ was added 0.60 mL (4.3 mmol) NEt$_3$ and 0.25 ml (1.58 mmol) benzyloxyacetyl chloride. After stirring for 18 h, the reaction was poured into 75 mL H$_2$O and extracted with CH$_2$Cl$_2$ (4×50 mL). The combined organic layers were dried over MgSO$_4$, filtered, and evaporated under reduced pressure. Silica gel chromatography (5% MeOH in EtOAc) afforded (S)-N-[[3-[3-fluoro-4-{N-(benzyloxyacetyl)piperidinyl-4-oxy}phenyl]-2-oxo-5-oxazolidinyl]methyl]acetamide as a white glass. $^1$H NMR (CDCl$_3$) δ 7.47 (dd, J=12.9 and 2.5 Hz, 1H); 7.2–7.4 (m, 6H); 6.98 (t, J=8 (m, 1H); 6.24 (brt, J=6.1 Hz, 1H); 4.7–4.8 (m, 1H); 4.61 (s, 2H); 4.4–4.5 (m, 1H); 4.20 (s, 2H); 4.02 (t, J=9.0 Hz, 1H); 3.6–3.8 (m, 6H); 3.4–3.5 (m, 1H); 2.02 (s, 3H); and 1.8–1.9 (m, 4H).

EXAMPLE 4

(S)-N-[[3-[3-Fluoro-4-{N-(α-hydroxyacetyl)piperidinyl-4-oxy}phenyl]-2-oxo-5-oxazolidinyl]methyl]acetamide Compound 4

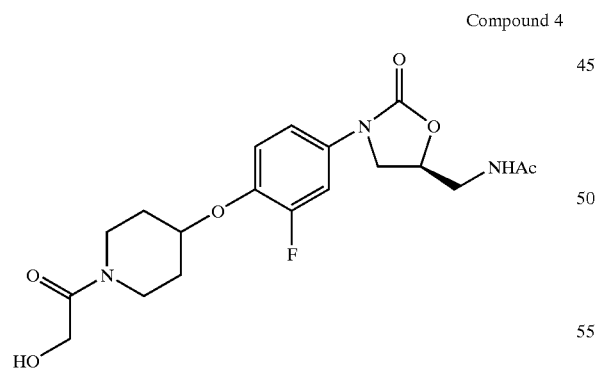

To a solution of 540 mg (1.08 mmol) of Compound 3 in 50 mL MeOH was added 503 mg ammonium formate and a catalytic amount of 10% Pd/C, and the reaction was heated at reflux overnight. Then the reaction was filtered through a pad of celite and the solvent removed under reduced pressure. Silica gel chromatography (2% to 10% MeOH in CH$_2$Cl$_2$) afforded (S)-N-[[3-[3-fluoro-4-{N-(α-hydroxyacetamide)piperidinyl-4-oxy}phenyl]-2-oxo-5-oxazolidinyl]methyl]acetyl as a hygroscopic white foam (93%). $^1$H NMR (CDCl$_3$) δ 7.49 (dd, J=12.9 and 2.6 Hz, 1H); 7.09 (dd, J=8.9 and 1.6 Hz, 1H); 7.00 (t, J=8.9 Hz, 1H); 6.18 (brt, J=6.1 Hz, 1H); 4.7–4.8 (m, 1H); 4.51 (q, J=4.6 Hz, 1H); 4.19 (s, 2H); 4.02 (t, J=9.0 Hz, 1H); 3.5–3.8 (m, 7H); 3.20 (dt, J=13.7 and 5.2 Hz, 1H); 2.03 (s, 3H); and 1.90 (m, 4H).

EXAMPLE 5

(S)-N-[[3-[3-Fluoro-4-{N-(methoxyacetyl)piperidinyl-4-oxy}phenyl]-2-oxo-5-oxazolidinyl]methyl]acetamide Compound 5

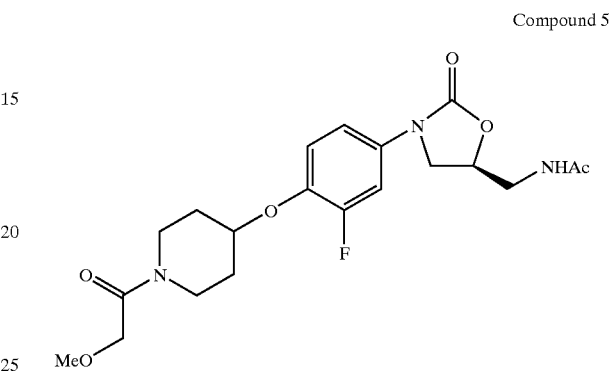

To a solution of (S)-N-[[3-[3-fluoro-4-{piperidinyl-4-oxy}phenyl]-2-oxo-5-oxazolidinyl]methyl]acetamide (0.756 mmol) in 30 mL EtOAc was added 1.0 mL (7.17 mmol) NEt$_3$ and methoxyacetylchloride (0.875 mmol). The reaction stirred at rt for 2.5 h, was poured into 50 mL H$_2$O, and extracted with EtOAc. The organic layer was washed with H$_2$O, dried over MgSO$_4$, filtered, and the solvent removed by rotary evaporation to yield the impure amide. Silica gel chromatography (2.5 to 10% MeOH in CH$_2$Cl$_2$) afforded 101 mg (32%) of (S)-N-[[3-[3-fluoro-4-{N-(methoxyacetyl)piperidinyl-4-oxy}phenyl]-2-oxo-5-oxazolidinyl]methyl]acetamide as a beige foam. $^1$H NMR (CDCl$_3$) δ 7.48 (dd, J=12.9 and 2.5 Hz, 1H); 7.10 (m, 1H); 7.00 (t, J=8.8 Hz, 1H); 6.00 (brt, 1H); 4.77 (m, 1H); 4.46 (m, 1H); 4.13 (s, 2H); 4.03 (t, J=8.9 Hz, 1H); 3.5–3.8 (m, 6H); 3.44 (s, 3H); 3.43 (m, 1H); 2.03 (s, 3H); and 1.7–1.9 (m, 4H).

EXAMPLE 6

(S)-N-[[3-[3-Fluoro-4-{N-(methanesulfonyl)piperidinyl-4-oxy}phenyl]-2-oxo-5-oxazolidinyl]methyl]acetamide Compound 6

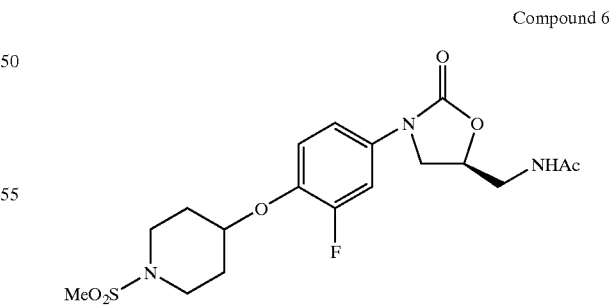

To a solution of 115 mg (0.33 mmol) of Compound 2 in 5 mL CH$_2$Cl$_2$ was added 0.05 mL (0.36 mmol) NEt$_3$ and 0.03 mL (0.39 mmol) methanesulfonyl chloride. The reaction stirred at rt for 22 h, was poured into 50 mL H$_2$O, and extracted with CH$_2$Cl$_2$. The combined organic layers were washed with H$_2$O, dried over MgSO$_4$, filtered, and the solvent removed by rotary evaporation to yield the impure sulfonamide. The sulfonamide was purified by dissolving in EtOAc, washing with sat. NaHCO₃, drying over MgSO₄, and removal of the solvent under reduced pressure to give (S)-N-[[3-[3-fluoro-4-{N-(methanesulfonyl)piperidinyl-4-oxy}phenyl]-2-oxo-5-oxazolidinyl]methyl]acetamide; mp 123–125° C., MS (Cl) [M+H]⁺ 430.

EXAMPLE 7

(S)-N-[[3-[3-Fluoro-4-{N-(acetyl)piperidinyl-4-oxy}phenyl]-2-oxo-5-oxazolidinyl]methyl]acetamide Compound 7

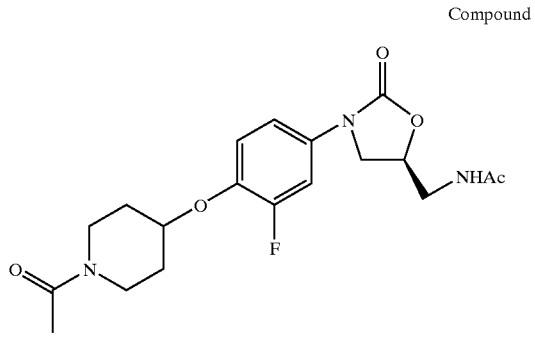

To a solution of 155 mg (0.44 mmol) of Compound 2 in 30 mL CH₂Cl₂ was added 0.10 mL (0.72 mmol) NEt₃ and 0.05 mL (0.70 mmol) acetyl chloride. The reaction stirred at rt for 18 h, was poured into 50 mL H₂O, and extracted with CH₂Cl₂. The combined organic layers were washed with H₂O, dried over MgSO₄, filtered, and the solvent removed by rotary evaporation to yield the impure amide. The amide was purified by dissolving in EtOAc, washing with sat. NaHCO₃, dryng over MgSO₄, and the solvent removed under reduced pressure to give (S)-N-[[3-[3-fluoro-4-{N-(acetyl)piperidinyl-4-oxy}phenyl]-2-oxo-5-fS oxazolidinyl]methyl]acetamide. ¹H NMR (CDCl₃) δ 7.47 (dd, J=12.9 and 2.2 Hz, 1H); 7.06 (m, 2H); 6.97 (brt, J=8.8 Hz, 1H); 4.79 (m, 1H); 4.46 (m, 1H); 4.03 (t, J=9.0 Hz, 1H); 3.6–3.8 (m, 6H); 3.52 (m, 1H); 2.12 (s, 3H); 2.02 (s, (m, 4H)).

EXAMPLE 8

(S)-N-[[3-[3-Fluoro-4-{N-(methoxycarbonyl)piperidinyl-4-oxy}phenyl]-2-oxo-5-oxazolidinyl]methyl]acetamide Compound 8

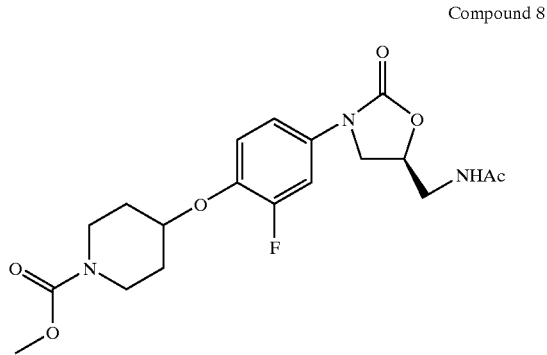

To a solution of 201 mg (0.57 mmol) of Compound 2 in 50 mL EtOAc was added 0.15 mL NEt₃ and 0.10 mL methylchloroformate. The reaction stirred at rt for 20 h, was poured into 50 mL H₂O, and extracted with EtOAc. The combined organic layers were washed with H₂O, dried over MgSO₄, filtered, and the solvent removed by rotary evaporation to yield 167 mg (72%) of (S)-N-[[3-[3-fluoro-4-{N-(methoxycarbonyl)piperidinyl-4-oxy}phenyl]-2-oxo-5-oxazolidinyl]methyl]acetamide as a white solid. ¹H NMR (CDCl₃) δ 7.47 (m, 1H); 7.26 (m, 1H); 7.06 (m, 1H); 6.03 (m, 1H); 4.78 (m, 1H); 4.41 (m, 1H); 4.02 (t, J=8.9 Hz, 1H); 3.71 (s, 3H); (m, 5H); 3.41 (m, 2H); 2.02 (s, 3H); 1.89 (m, 2H); and 1.79 (m, 2H).

EXAMPLE 9

(S)-N-[[3-[3-Fluoro-4-{N-(2-pyrimidinyl)piperidinyl-4-oxy}phenyl]-2-oxo-5-oxazolidinyl]methyl]acetamide Compound 9

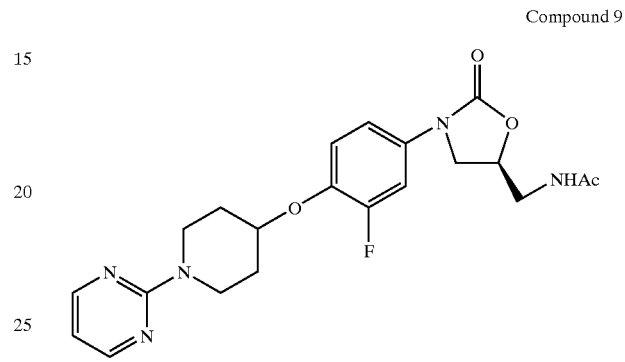

To a solution of 176 mg (0.50 mmol) of Compound 2 in 7.5 mL EtOH was added 0.23 mL NEt₃ and 61 mg (0.53 mmol) 2-chloropyrimidine and the reaction heated at reflux for 21 h. After cooling, the reaction was poured into 50 mL sat. NaHCO₃, and extracted with CH₂Cl₂ (4×50 mL). The combined organic layers were washed with H₂O, dried over MgSO₄, filtered, and the solvent removed by rotary evaporation to yield 174 mg (81%) of (S)-N-[[3-[3-fluoro-4-{N-(2-pyrimidinyl)piperid inyl⁴-oxy}phenyl]-2-oxo-5-oxazolidinyl]methyl]acetamide; mp 121–123° C., MS (Cl) [M+H]⁺ 430.

EXAMPLE 10

(S)-N-[[3-[3-Fluoro-4-{N-(3-trifluoromethylbenzoyl)piperidinyl-4-oxy}phenyl]-2-oxo-5-oxazolidinyl]methyl]acetamide Compound 10

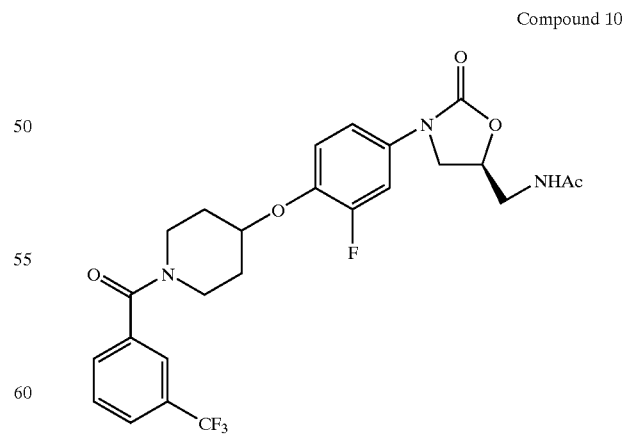

To a solution of 101 mg (0.29 mmol) of Compound 2 in 10 mL CH₂Cl₂ was 5 added 260 mg AMBERLYST 21 Basic Resin and 1.0 mL (6.6 mmol) 3-trifluoromethylbenzoyl chloride and the reaction shaken for 3.5 h at rt. Then 2.4 g P-trisamine was added and the reaction shaken overnight. The reaction was filtered and the resin washed with $CH_2Cl_2$. The combined organic layers were washed with sat. $NaHCO_3$, dried over $MgSO_4$, filtered, and the solvent removed by rotary evaporation to yield the crude amide. The amide was triturated with hexanes 3 times to afford 100 mg (67%) of (S)-N-[[3-[3-fluoro-4-{N-(3-trifluoromethylbenzoyl)piperidinyl-4-oxy}phenyl]-2-oxo-5-oxazolidinyl]methyl]acetamide as a white powder; mp 150–152° C., MS (Cl) [M+H]$^+$ 524.

EXAMPLE 11

(S)-N-[[3-[3-Fluoro-4-{N-(4-cyanobenzoyl) piperidinyl-4-oxy}phenyl]-2-oxo-5-oxazolidinyl] methyl]acetamide Compound 11

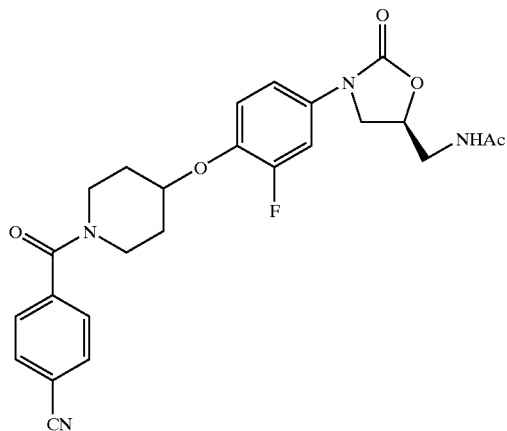

To a solution of 51 mg (0.15 mmol) of Compound 2 in 7.5 mL $CH_2Cl_2$ was added 207 mg AMBERLYST 21 Basic Resin and 116 mg (0.70 mmol) 4-cyanobenzoyl chloride and the reaction was shaken for 18 h at rt. Then 250 mg P-trisamine was added and the reaction was shaken for 20 h. The reaction was filtered and the resin washed with $CH_2Cl_2$. The organic solvent was removed by rotary evaporation to yield 63 mg (91%) of (S)-N-[[3-[3-fluoro-4-{N-(4-cyanobenzoyl)piperidinyl-4-oxy}phenyl]-2-oxo-5-oxazolidinyl]methyl]acetamide; mp 75–78° C., MS (Cl) [M+H]$^+$ 481.

EXAMPLE 12

(S)-N-[[3-[3-Fluoro-4-{N-(3-cyanobenzoyl) piperidinyl-4-oxy}phenyl]-2-oxo-5-oxazolidinyl] methyl]acetamide Compound 12

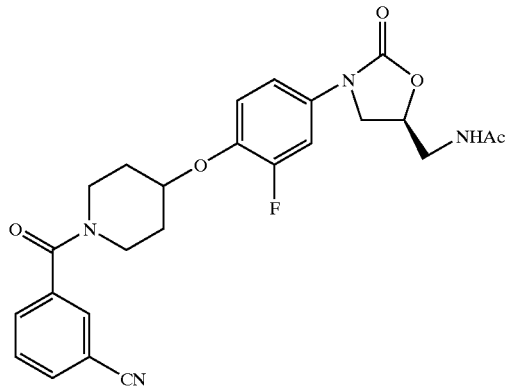

To a solution of 75 mg (0.21 mmol) of Compound 2 in 7.5 mL $CH_2Cl_2$ was added 200 mg AMBERLYST 21 Basic Resin and 128 mg (0.77 mmol) 3-cyanobenzoyl chloride and the reaction was shaken for 18 h at rt. Then 300 mg P-trisamine was added and the reaction was shaken for 20 h. The reaction was filtered and the resin washed with $CH_2Cl_2$. The organic solvent was removed by rotary evaporation to yield 103 mg (100%) of (S)-N-[[3-[3-fluoro-4-{N-(3-cyanobenzoyl)piperidinyl-4-oxy}phenyl]-2-oxo-5-oxazolidinyl]methyl]acetamide; mp 82–85° C., MS (Cl) [M+H]$^+$ 481.

EXAMPLE 13

(S)-N-[[3-[3-Fluoro-4-{N-(4-methoxybenzoyl) piperidinyl-4-oxy}phenyl]-2-oxo-5-oxazolidinyl] methyl]acetamide Compound 13

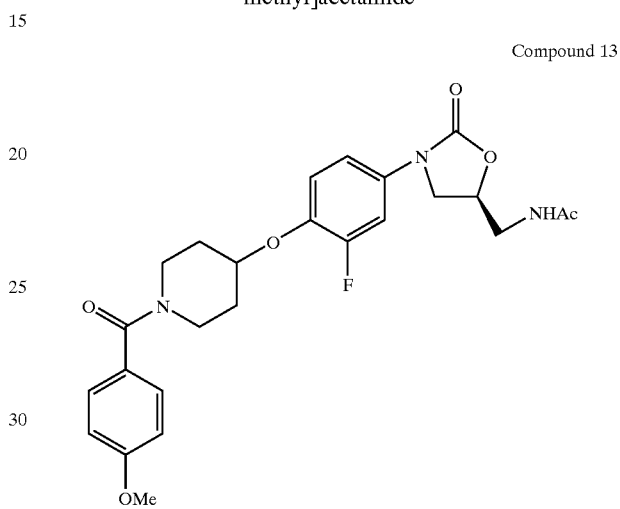

To a solution of 133 mg (0.29 mmol) of Compound 2 in 10 mL $CH_2Cl_2$ was 5 added 350 mg AMBERLYST 21 Basic Resin and 255 mg (1.49 mmol) p-anisoyl chloride and the reaction was shaken for 3 h at rt. Then 1.0 g P-trisamine was added and the reaction was shaken for 48 h. The reaction was filtered and the resin washed with $CH_2Cl_2$. The organic solvent was removed by rotary evaporation to yield (S)-N-[[3-[3-fluoro-4-{N-(4-methoxybenzoyl)piperidinyl-4-oxy}phenyl]-2-oxo-5-oxazolidinyl]methyl]acetamide as a yellow glass; $^1$H NMR (CDCl$_3$) δ 7.50 (m, 1H); 7.39 (m, 2H); 7.05 (m, 1H); 7.03 (m, 1H); 6.90 (m, 2H); 7H); 2.06 (s, 3H); and 1.95 (m, 4H).

EXAMPLE 14

(S)-N-[[3-[3-Fluoro-4-{N-(5-cyano-2-pyridyl) piperidinyl-4-oxy}phenyl]-2-oxo-5-oxazolidinyl] methyl]acetamide Compound 14

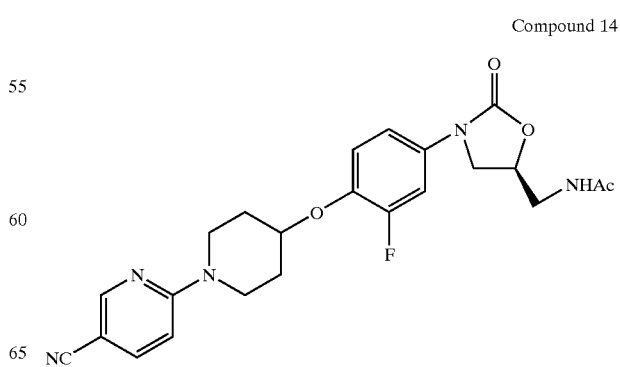

To a solution of 170 mg (0.48 mmol) of Compound 2 in 15 mL EtOH was added 0.15 mL NEt$_3$ and 80 mg (0.58 mmol) 2-chloropyridine-5-carbonitrile and the reaction was heated at 80° C. for 72 h. After cooling, the reaction was poured into 50 mL H$_2$O and extracted with CH$_2$Cl$_2$. The combined organic layers were dried over MgSO$_4$, filtered, and the solvent removed by rotary evaporation to yield the crude product. Silica gel chromatography (1% MeOH in EtOAc) yielded 160 mg (73%) of (S)-N-[[3-[3-fluoro-4-{N-(5-cyano-2-pyridyl)piperidinyl-4-oxy}phenyl]-2-oxo-5-oxazolidinyl]methyl]acetamide as a yellow solid; mp 78–84° C., MS (Cl) [M+H]$^+$ 454.

EXAMPLE 15
(S)-N-[[3-[3-Fluoro-4-{N-(α-phenylmethoxycarbonylaminoacetyl)piperidinyl-4-oxy}phenyl]-2-oxo-5-oxazolidinyl]methyl] acetamide Compound 15

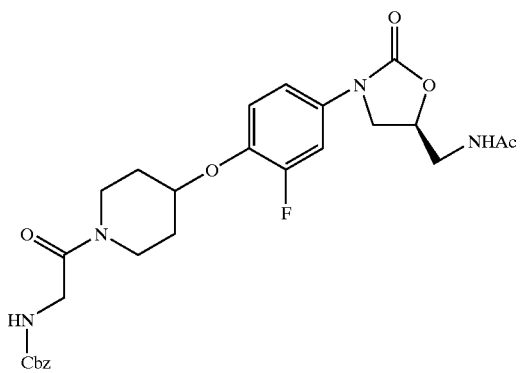

To a solution of 266 mg (0.76 mmol) of Compound 2 in 15 mL CH$_2$Cl$_2$ was added 0.2 mL NEt$_3$ and 188 mg (0.89 mmol) phenylmethoxycarbonylglycine acid fluoride and the reaction was stirred at rt for 1.5 h. Then the reaction was poured into 50 mL sat. NaHCO$_3$ and extracted with CH$_2$Cl$_2$. The combined organic layers were dried over MgSO$_4$, filtered, and the solvent removed by rotary evaporation afford 375 mg (91%) of crude (S)-N-[[3-[3-fluoro-4-{N-(α-phenylmethoxycarbonylamino acetyl)piperidinyl-4-oxy}phenyl]-2-oxo-5-oxazolidinyl]methyl]acetamide. $^1$H NMR (CDCl$_3$) δ 7.50 (m, 1H); 7.39 (m, 5H); 7.11 (m, 1H); 7.03 (m, 1H); 6.24 (m, 1H); 5.87 (m, 1H); 5.15 (s, 2H); 4.75 (m, 1H); 4.52 (m, 1H); 4.06 (m, 3H); 3.6–3.8 (m, 6H); 3.37 (m, 1H); 2.10 (s, 3H); and 1.90 (m, 4H).

EXAMPLE 16
(S)-N-[[3-[3-Fluoro-4-{N-α-aminoacetyl)piperidinyl-4-oxy}phenyl]-2-oxo-5-oxazolidinyl] methyl]acetamide Compound 16

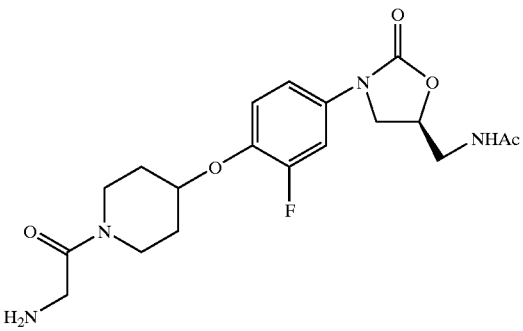

A solution of 340 mg (0.62 mmol) of Compound 15 in 30 mL of EtOH was treated with 36 mg 10% Pd/C, followed by hydrogenation at 50 psi overnight. The suspension was filtered through celite and the filtrate evaporated under reduced pressure to afford crude amine. Trituration of the crude solid with CHCl$_3$ yielded (S)-N-[[3-[3-fluoro-4-{N-(α-amino acetyl)piperidinyl-4-oxy}phenyl]-2-oxo-5-oxazolidinyl]methyl]acetamide; mp 142–146° C., MS (Cl) [M+H]$^+$ 409.

EXAMPLE 17
(S)-N-[[3-[3-Fluoro-4-{N-(α-methylsulfonylaminoacetyl)piperidinyl-4-oxy}phenyl]-2-oxo-5-oxazolidinyl]methyl] acetamide Compound 17

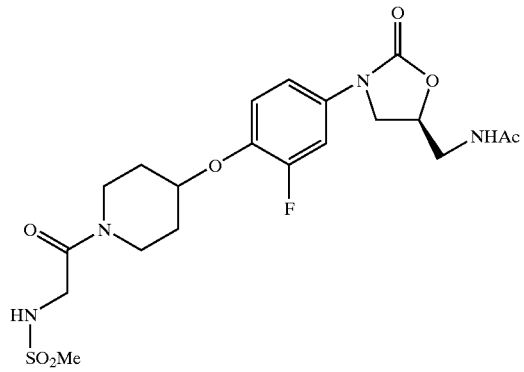

To a solution of 750 mg (4.28 mmol) Boc-glycine in 25 mL CH$_2$Cl$_2$ was added 0.6 mL DAST and the reaction stirred at rt for 20 min. Then the reaction was washed with cold H$_2$O, the organic layer dried over MgSO$_4$, filtered, and the solvent removed under reduced pressure to give a brown solid. To a solution of this acid fluoride in 40 mL CH$_2$Cl$_2$ was added 327 mg (0.70 mmol) of the TFA salt from Example 2 and 0.23 mL NEt$_3$ and the reaction stirred at rt for 16 h. The reaction was poured into 50 mL sat. NaHCO$_3$, extracted with CH$_2$Cl$_2$ washed with H$_2$O, dried over MgSO$_4$, filtered, and the solvent removed under reduced pressure to give 388 mg of the amide as a beige foam. To a solution of 0.70 mmol of this amide was added 0.55 mL trifluoroacetic acid and the reaction stirred at rt for 20 h. The volatiles were evaporated under reduced pressure to give a brown oil. To this TFA salt in 30 mL CH$_2$Cl$_2$ was added 0.23 mL NEt$_3$ and 0.07 mL (0.90 mmol) methanesulfonyl chloride and the reaction stirred at rt for 18 h. The reaction was poured into 50 mL sat. NaHCO$_3$, extracted with CH$_2$Cl$_2$, washed with H$_2$O, dried over MgSO$_4$, filtered, and the solvent removed under reduced pressure to give the crude sulfonamide. Purification by silica gel chromatography (5% MeOH in CH$_2$Cl$_2$) yielded 109 mg (32%) of (S)-N-[[3-[3-fluoro-4-{N-(α-methylsulfonylaminoacetyl)piperidinyl-4-oxy}phenyl]-2-oxo-5-oxazolidinyl]methyl]acetamide as a white foam; mp 78–82° C., MS (Cl) [M+H]$^+$ 487.

EXAMPLE 18

(S)-N-[[3-[3-Fluoro-4-{N-(α-N-acetylaminoacetyl)piperidinyl-4-oxy}phenyl]-2-oxo-5-oxazolidinyl]methyl]acetamide Compound 18

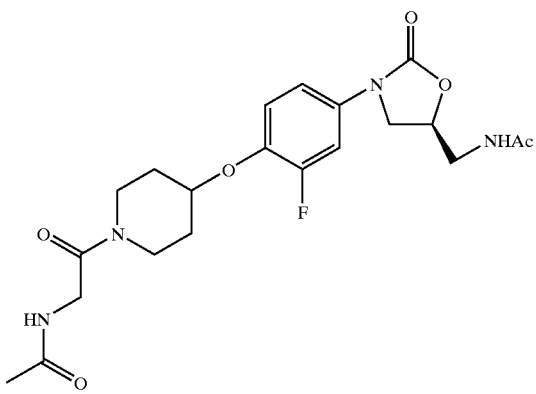

To a solution of 74 mg (0.63 mmol) N-acetylglycine in 10 mL CH$_2$Cl$_2$ was added 125 mg (0.65 mmol) EDCl and the reaction stirred at rt for 2 h. Then a solution of 304 mg (0.65 mmol) TFA salt from Example 2 and 0.15 mL (1.07 mmol) NEt$_3$ in 10 mL CH$_2$Cl$_2$ was added and the reaction stirred at rt for 3 h. The reaction was poured into 10 mL H$_2$O and extracted with CH$_2$Cl$_2$. The combined organic layers were dried over MgSO$_4$, filtered, and the solvent removed by rotary evaporation to yield the crude product as a yellow oil. Silica gel chromatography (5% MeOH in CH$_2$Cl$_2$) yielded 161 mg of (S)-N-[[3-[3-fluoro-4-{N-(α-N-acetylaminoacetyl)piperidinyl-4-oxy}phenyl]-2-oxo-5-oxazolidinyl]methyl]acetamide; mp 66–68° C., MS (Cl) [M+H]$^+$ 451.

EXAMPLE 19

(S)-N-[[3-[3-Fluoro-4-{N-(3-pyridoyl)piperidinyl-4-oxy}phenyl]-2-oxo-5-oxazolidinyl]methyl]acetamide Compound 19

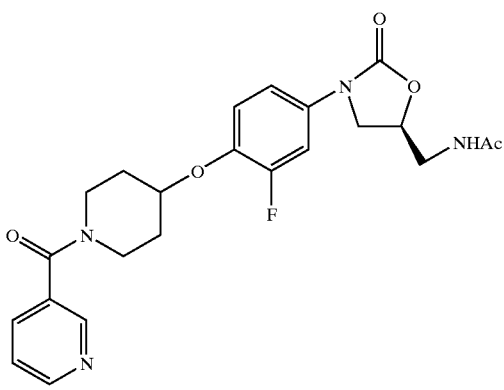

To a solution of 257 mg (0.55 mmol) of the TFA salt in Example 2 in 20 mL CH$_2$Cl$_2$ was added 0.4 mL (2.86 mmol) NEt$_3$ and 105 mg (0.59 mmol) nicotinoyl chloride hydrochloride and the reaction stirred at rt for 20 h. The reaction was poured into 50 mL sat. NaHCO$_3$ and extracted with CH$_2$Cl$_2$. The combined organic layers were washed with H$_2$O, dried over MgSO$_4$, filtered, and the solvent removed by rotary evaporation to yield 161 mg (64%) of (S)-N-[[3-[3-fluoro-4-{N-(3-pyridoyl)piperidinyl-4-oxy}phenyl]-2-oxo-5-oxazolidinyl]methyl]acetamide; mp 49–53° C., MS (Cl) [M+H]$^+$ 457.

EXAMPLE 20

(S)-N-[[3-[3-Fluoro-4-{N-(2-pyridoyl)piperidinyl-4-oxy}phenyl]-2-oxo-5-oxazolidinyl]methyl]acetamide Compound 20

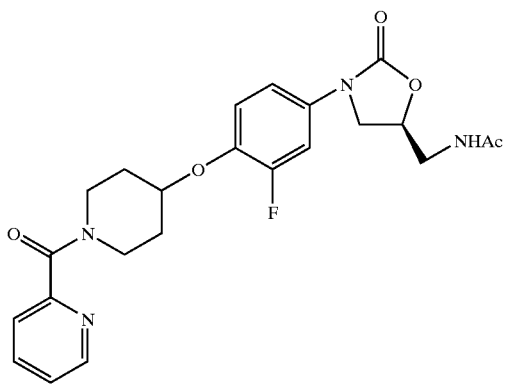

To a solution of 281 mg (0.60 mmol) of the TFA salt in Example 2 in 50 mL CH$_2$Cl$_2$ was added 0.3 mL NEt$_3$ and 110 mg (0.62 mmol) pyridine 2-carbonyl chloride hydrochloride and the reaction stirred at rt for 72 h. The reaction was poured into 50 mL sat. NaHCO$_3$, and extracted with CH$_2$Cl$_2$. The combined organic layers were washed with H$_2$O, dried over MgSO$_4$, filtered, and the solvent removed by rotary evaporation to yield 190 mg (69%) of (S)-N-[[3-[3-fluoro-4-{N-(2-pyridoyl)piperidinyl-4-oxy}phenyl]-2-oxo-5-oxazolidinyl]methyl]acetamide; mp 55–58° C., MS (Cl) [M+H]$^+$ 457.

EXAMPLE 21

(S)-N-[[3-[3-Fluoro-4-{N-(4-pyridoyl)piperidinyl-4-oxy}phenyl]-2-oxo-5-oxazolidinyl]methyl]acetamide Compound 21

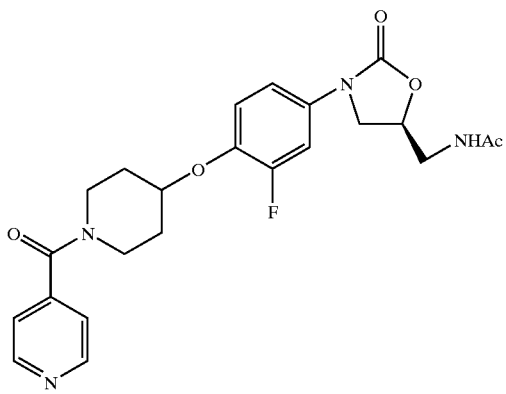

To a solution of 285 mg (0.61 mmol) of the TFA salt in Example 2 in 25 mL CH$_2$Cl$_2$ was added 0.5 mL NEt$_3$ and 123 mg (0.69 mmol) isonicotinoyl chloride hydrochloride and the reaction stirred at rt for 20 h. The reaction was poured into 50 mL sat. NaHCO$_3$, and extracted with CH$_2$Cl$_2$. The combined organic layers were washed with H$_2$O, dried over MgSO$_4$, filtered, and the solvent removed by rotary evaporation to yield 29 mg (10%) of (S)-N-[[3-[3-fluoro-4-{N-(4-pyridoyl)piperidinyl-4-oxy}phenyl]-2-oxo-5-oxazolidinyl]methyl]acetamide as a white foam. $^1$H NMR (CDCl$_3$) δ 8.73 (m, 2H); 7.50 (m, 1H); 7.41 (m, 2H); 7.06 (m, 2H); 6.08 (br t, 1H); 4.69 (m, 1H); 4.54 (m, 1H); 4.04 (m, 1H); 3.90 (m, 2H); 3.6–3.8 (m, 4H); 3.34 (m, 1H); 2.03 (s, 3H); 1.97 (m, 2H); and 1.82 (m, 2H).

EXAMPLE 22

(S)-N-[[3-[3-Fluoro-4-{N-(2-thienylcarbonyl)piperidinyl-4-oxy}phenyl]-2-oxo-5-oxazolidinyl]methyl]acetamide Compound 22

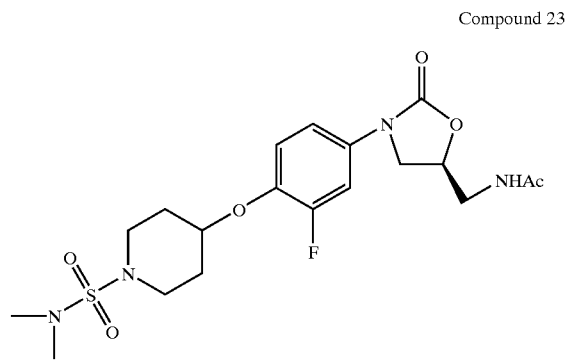

To a solution of 251 mg (0.55 mmol) of the TFA salt in Example 2 in 25 mL CH$_2$Cl$_2$ was added 0.2 mL NEt$_3$ and 0.07 mL (0.65 mmol) 2-thiophenecarbonyl chloride and the reaction stirred at rt for 72 h. The reaction was poured into 50 mL sat. NaHCO$_3$ and extracted with CH$_2$Cl$_2$. The combined organic layers were washed with H$_2$O, dried over MgSO$_4$, filtered, and the solvent removed by rotary evaporation to give the crude product. The crude material was dissolved in 50 mL CH$_2$Cl$_2$, P-trisamine resin added and the mixture stirred for 2 h. The reaction was filtered and the solvent evaporated under reduced pressure to give (S)-N-[[3-[3-fluoro-4-{N-(2-thienylcarbonyl)piperidinyl4-oxy}phenyl]-2-oxo-5-oxazolidinyl]methyl]acetamide; mp 48–51° C., MS (Cl) [M+H]$^+$ 462.

EXAMPLE 23

(S)-N-[[3-[3-Fluoro-4-{N-(dimethylsulfamoyl)piperidinyl-4-oxy}phenyl]-2-oxo-5-oxazolidinyl]methyl]acetamide Compound 23

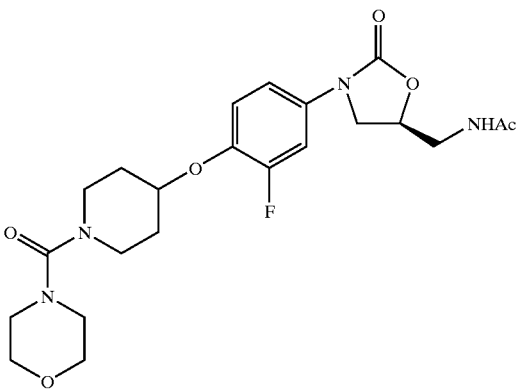

To a solution of 179 mg (0.38 mmol) of the TFA salt in Example 2 in 20 mL CH$_2$Cl$_2$ was added 0.12 mL NEt$_3$ and 0.05 mL (0.47 mmol) dimethylsulfamoyl chloride and the reaction stirred at rt for 18 h. The reaction was poured into 50 mL sat. NaHCO$_3$ and extracted with CH$_2$Cl$_2$. The combined organic layers were washed with H$_2$O, dried over MgSO$_4$, filtered, and the solvent removed by rotary evaporation to give the crude product. The crude oil was crystallized from warm CH$_2$Cl$_2$/Et$_2$O to give (S)-N-[[3-[3-fluoro-4-{N-(dimethylsulfamoyl)piperidinyl-4-oxy}phenyl]-2-oxo-5-oxazolidinyl]methyl]acetamide as a white solid; mp 132–134° C., MS (Cl) [M+H]$^+$ 459.

EXAMPLE 24

(S)-N-[[3-[3-Fluoro-4-{N-(dimethylcarbamoyl)piperidinyl-4-oxy}phenyl]-2-oxo-5-oxazolidinyl]methyl]acetamide Compound 24

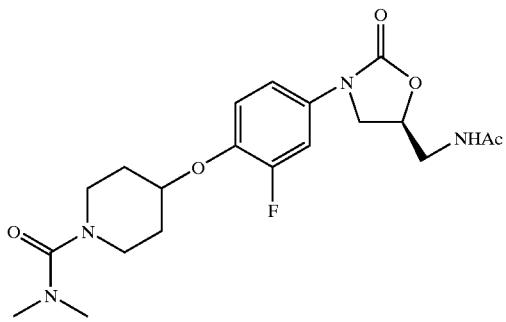

To a solution of 229 mg (0.49 mmol) of the TFA salt in Example 2 in 20 mL CH$_2$Cl$_2$ was added 0.15 mL (1.08 mmol) NEt$_3$ and 0.06 mL (0.65 mmol) dimethylcarbamoylchloride and the reaction stirred at rt overnight. The reaction was poured into 50 mL sat. NaHCO$_3$, and extracted with CH$_2$Cl$_2$. The combined organic layers were washed with H$_2$O, dried over MgSO$_4$, filtered, and the solvent removed by rotary evaporation to give the crude product. The crude oil was crystallized from warm CH$_2$Cl$_2$/Et$_2$O to give 175 mg (85%) of (S)-N-[[3-[3-fluoro-4-{N-(dimethylcarbamoyl)piperidinyl-4-oxy}phenyl]-2-oxo-5-oxazolidinyl]methyl]acetamide as a white solid; mp 129–131° C., MS (Cl) [M+H]$^+$ 423.

EXAMPLE 25

(S)-N-[[3-[3-Fluoro-4-{N-(4-morpholinocarbamoyl)piperidinyl-4-oxy}phenyl]-2-oxo-5-oxazolidinyl]methyl]acetamide Compound 25

To a solution of 205 mg (0.44 mmol) of the TFA salt in Example 2 in 25 mL $CH_2Cl_2$ was added 0.13 mL $NEt_3$ and 0.06 mL (0.51 mmol) 4-morpholinecarbonyl chloride and the reaction stirred for 4 h. The reaction was poured into 50 mL sat. $NaHCO_3$ and extracted with $CH_2Cl_2$. The combined organic layers were washed with $H_2O$, dried over $MgSO_4$, filtered, and the solvent removed by rotary evaporation to give the crude product. The crude product was triturated with $Et_2O$ and hexanes to give 198 mg (97%) of (S)-N-[[3-[3-fluoro-4-{N-(4-morpholinocarbamoyl)piperidinyl-4-oxy}phenyl]-2-oxo-5-oxazolidinyl]methyl]acetamide as a white solid; mp 167–170° C., MS (Cl) [M+H]+ 465.

EXAMPLE 26

(S)-N-[[3-[3-Fluoro-4-{N-(4-pyridin-3-yl-butyryl)piperidinyl-4-oxy}phenyl]-2-oxo-5-oxazolidinyl]methyl]acetamide Compound 26

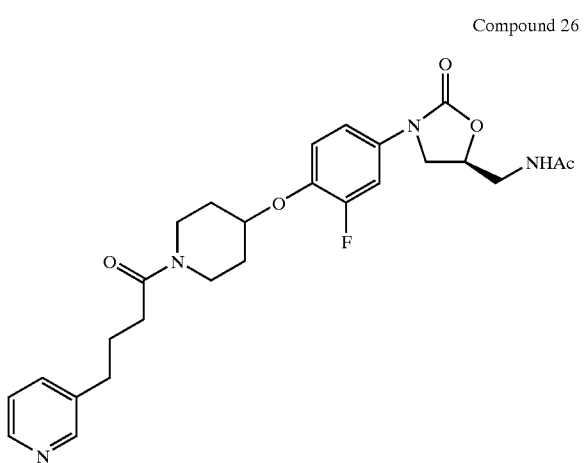

4-Pyridin-3-yl-butyronitrile:

To a solution of 0.66 mL (5.11 mmol) 3-pyridine propanol in 5 mL $CH_2Cl_2$ at 0° C. was added 0.62 mL (7.67 mmol) pyridine and 0.47 mL (6.14 mmol) methanesulfonyl chloride and the reaction stirred for 4 h. The solution was concentrated under reduced pressure and the crude mesylate dissolved in 10 mL DMF. To this solution was added 902 mg (18.41 mmol) sodium cyanide and the reaction stirred at 60° C. for 3 days. Then the solution was cooled, diluted with $H_2O$ (30 mL) and extracted with EtOAc (3×20 mL). The combined organic layers were washed with $H_2O$, dried over $MgSO_4$, and the solvent removed under reduced pressure to give a dark red oil. The crude nitrile was purified by dissolving in EtOAc, washing with $H_2O$, concentrating, and filtering through a silica gel plug (5% MeOH in $CH_2Cl_2$) to yield 425 mg (57%) of the nitrile.

4-Pyridin-3-yl-butyric Acid:

A solution of 425 mg (2.91 mmol) of 4-pyridin-3-yl-butyronitrile in 15 mL conc. HCl was refluxed for 8 h. The volatiles were evaporated under reduced pressure and the residue dissolved in EtOH. Upon addition of acetone and cooling a dark brown solid precipitated. The filtrate was concentrated and triturated with cold acetone to collect a total of 334 mg (69%) of the carboxylic acid.

4-Pyridin-3-yl-butyryl Chloride:

To a solution of 247 mg (1.49 mmol) of 4-pyridin-3-yl-butyric acid in 10 mL $CH_2Cl_2$ was added one drop DMF and 2.3 mL (4.56 mmol) oxalyl chloride and the mixture stirred at rt for 4 h. The volatiles were evaporated under reduced pressure and the material used crude in the following procedure.

(S)-N-[[3-[3-Fluoro-4-{N-(4-pyridin-3-yl-butyryl)piperidinyl-4-oxy}phenyl]-2-oxo-5-oxazolidinyl]methyl]acetamide (Compound 26):

To a solution of 597 mg (1.29 mmol) of the TFA salt in Example 2 in 20 mL $CH_2Cl_2$ was added 0.54 mL (3.86 mmol) $NEt_3$ at 0° C. and the reaction stirred for 30 min, warming to rt. Then the solution was cooled to 0° C., a solution of the previous acid chloride in 20 mL $CH_2Cl_2$ was added, and the reaction allowed to warm to rt. The reaction was diluted with $CH_2Cl_2$, washed with sat. $NaHCO_3$ (2×30 mL), washed with $H_2O$ (2×30 mL), dried over $MgSO_4$, filtered, and the solvent removed by rotary evaporation to give the crude product as a tan foam. Purification by silica gel chromatography (10% MeOH in EtOAc) yielded 152 mg (24%) of (S)-N-[[3-[3-fluoro-4-{N-(4-pyridin-3-yl-butyryl)piperidinyl-4-oxy}phenyl]-2-oxo-5-oxazolidinyl]methyl]acetamide as an off-white foam; mp 42–45° C., MS (Cl) [M+H]+ 499.

EXAMPLE 27

(S)-N-[[3-[3-Fluoro-4-{N-(3-pyridin-3-yl-propionyl)piperidinyl-4-oxy}phenyl]-2-oxo-5-oxazolidinyl]methyl]acetamide Compound 27

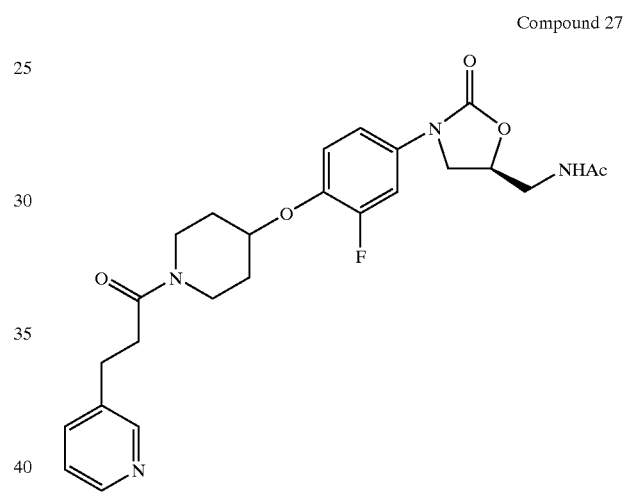

3-Pyridine Propionyl Chloride:

To a solution of 300 mg (1.99 mmol) 3-pyridine propionic acid in 10 mL $CH_2Cl_2$ was added one drop DMF and 2.3 mL (4.56 mmol) oxalyl chloride, and the mixture stirred at rt for 4 h. The volatiles were evaporated under reduced pressure and the material used crude in the following procedure.

(S)-N-[[3-[3-Fluoro-4-{N-(3-pyridin-3-yl-propionyl)piperidinyl-4-oxy}phenyl]-2-oxo-5-oxazolidinyl]methyl]acetamide (Compound 27):

To a solution of 917 mg (1.97 mmol) of the TFA salt in Example 2 in 20 mL $CH_2Cl_2$ was added 0.75 mL (5.41 mmol) $NEt_3$ at 0° C. and the reaction stirred for 30 min, warming to rt. Then the solution was cooled to 0° C., a solution of the previous acid chloride in 20 mL $CH_2Cl_2$ was added along with an additional equivalent of $NEt_3$, and the reaction allowed to warm to rt and stirred overnight. The reaction was diluted with $CH_2Cl_2$, washed with sat. $NaHCO_3$ (2×30 mL), washed with $H_2O$ (2×30 mL), dried over $Na_2SO_4$, filtered, and the solvent removed by rotary evaporation to give the crude product as a dark orange oil. Purification by silica gel chromatography (10% MeOH and 1% $NEt_3$ in EtOAc) yielded 110 mg of (S)-N-[[3-[3-fluoro-4-{N-(3-pyridin-3-yl-propionyl)piperidinyl-4-oxy}phenyl]-2-oxo-5-oxazolidinyl]methyl]acetamide as a foam; mp 45–47° C., MS (Cl) [M+H]+ 485.

EXAMPLE 28

(S)-N-[[3-[3-Fluoro-4-{N-(3-phenyl-propionyl)piperidinyl-4-oxy}phenyl]-2-oxo-5-oxazolidinyl]methyl]acetamide Compound 28

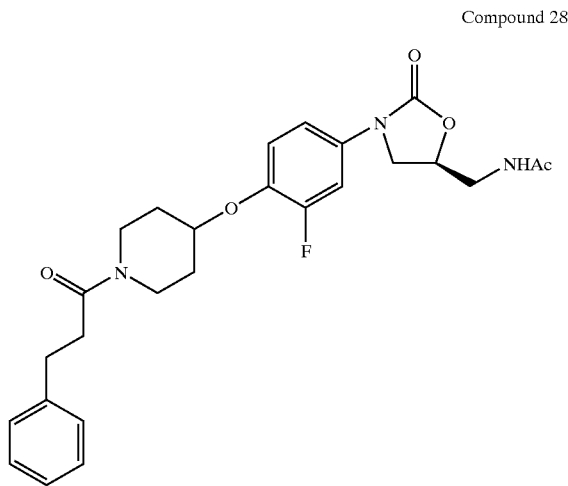

To a solution of 133 mg (0.27 mmol) of the TFA salt in Example 2 in 20 mL CH$_2$Cl$_2$ was added 0.07 mL (0.53 mmol) NEt$_3$ and 0.04 mL (0.29 mmol) hydrocinnamoyl chloride, and the reaction allowed to warm to rt and stirred for 1 h. The reaction was diluted with CH$_2$Cl$_2$, washed with sat. NaHCO$_3$ (2×30 mL), washed with H$_2$O (2×30 mL), dried over Na$_2$SO$_4$, filtered, and the solvent removed by rotary evaporation to give the crude product as a colorless oil. Purification by silica gel chromatography (10% MeOH in EtOAc) yielded a transparent glass. This material was triturated with EtOAc and hexanes to give (S)-N-[[3-[3-fluoro-4-{N-(3-phenyl-propionyl)piperidinyl-4-oxy}phenyl]-2-oxo-5-oxazolidinyl]methyl]acetamide as a white solid; MS (Cl) [M+H]$^+$ 484.

EXAMPLE 29

(S)-N-[[3-[4-{N-(Pyridin-2-ylmethoxyacetyl)piperidinyl-4-oxy}phenyl]-2-oxo-5-oxazolidinyl]methyl]acetamide Compound 29

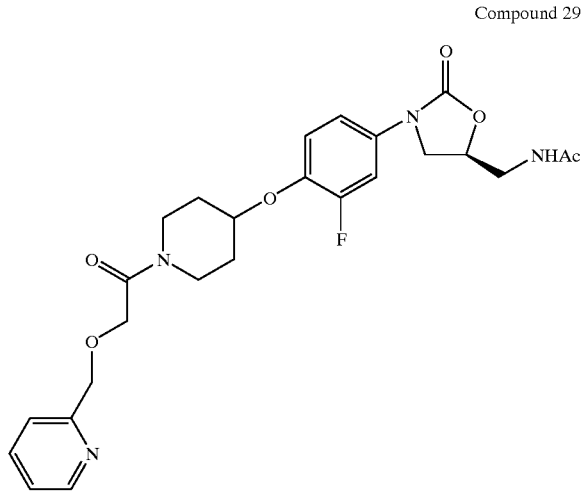

(Pyridin-2-yl-methoxy)-acetic Acid t-Butyl Ester:

To a solution of 0.5 mL (5.18 mmol) 2-pyridylmethanol in 20 mL THF at 0° C. was added 270 mg (6.75 mmol) NaH and the reaction stirred for 0.25 h. Then 0.82 mL t-butylbromoacetate was added and the reaction warmed to rt and stirred for 12 days. The reaction was poured into 100 mL H$_2$O, extracted with CH$_2$Cl$_2$ (2×100 mL), the combined organic layers washed with brine, dried over MgSO$_4$, filtered, and the solvent removed under reduced pressure to give 1.16 g (61%) as a brown oil.

(Pyridin-2-yl-methoxy)-acetic Acid:

To a solution of 706 mg (3.16 mmol) of (pyridin-3-yl-methoxy)-acetic acid t-butyl ester and 1.5 mL of TFA in 25 mL of methylene chloride were stirred at room temperature for 20 hr. The volatiles were evaporated to afford crude acid.

(S)-N-[[3-[4-{N-(Pyridin-2-ylmethoxyacetyl)piperidinyl-4-oxy}phenyl]-2-oxo-5-oxazolidinyl]methyl]acetamide (Compound 29):

To 460 mg (1.63 mmol) of (pyridin-2-yl-methoxy)acetic acid in 100 mL CH$_2$Cl$_2$ was added 405 mg (2.11 mmol) EDCl, 634 mg (1.36 mmol) of the TFA salt from example 1, and 4.5 mL (32.2 mmol) NEt$_3$. The reaction was stirred at rt for 5 days. Then the mixture was poured into 125 mL H$_2$O, extracted with CH$_2$Cl$_2$, the organic layers washed with brine, dried over MgSO$_4$, filtered, and the solvent removed by rotary evaporation. Purification by silica gel chromatography (5% MeOH in CH$_2$Cl$_2$) yielded 403 mg (59%) of (S)-N-[[3-[4-{N-(pyridin-2-ylmethoxyacetyl)piperidinyl-4-oxy}phenyl]-2-oxo-5-oxazolidinyl]methyl]acetamide as a yellow semi-solid. $^1$H NMR (CDCl$_3$) δ 8.54 (m, 1H); 7.72 (m, 1H); 7.49 (m, 2H); 7.23 (m, 1H); 7.09 (m, 1H); 7.00 (m, 1H); 6.10 (m, 1H); 4.78 (m, 1H); 4.71 (s, 2H); 4.48 (m, 1H); 4.32 (s, 2H); 4.04 (m, 1H); 3.6–3.8 (m, 6H); 3.45 (m, 1H); (s, 3H); and 1.83 (m, 4H).

EXAMPLE 30

(S)-N-[[3-[4-{N-(Benzyloxyacetyl)piperidinyl-4-oxy}phenyl]-2-oxo-5-oxazolidinyl]methyl]acetamide Compound 30

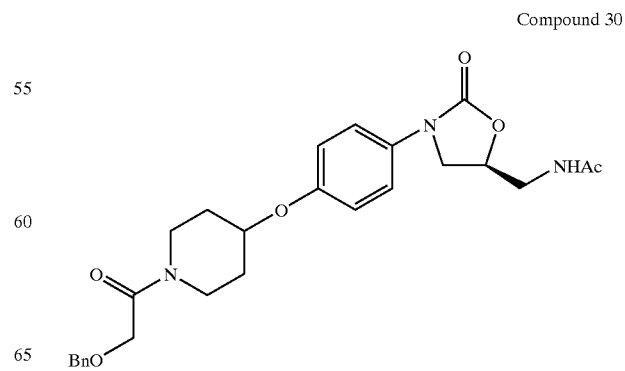

1-[N-(t-Butoxycarbonyl)piperidinyl-4-oxy]-4-nitrobenzene:

To a solution of 10.0 g (49.68 mmol) of N-(t-butoxycarbonyl)-4-piperidinol from example 1 in 125 mL dry THF at 0° C. was added dropwise 74 mL (74.53 mmol) 1 M KOtBu. After stirring at 0° C. for 0.5 h, 5.27 mL (49.68 mmol) p-fluoronitrobenzene was added and the reaction warmed to rt and stirred overnight. The volatiles were removed under reduced pressure and the reaction diluted with 800 mL $H_2O$. The mixture was extracted with $CH_2Cl_2$ (2×500 mL) and a brown solid removed by filtration. The combined aqueous layers were washed with $H_2O$, dried with $MgSO_4$, filtered, and the solvent removed by rotary evaporation to give an orange solid. Purification by silica gel chromatography (3:1 hexane:EtOAc) yielded 6.98 g (44%) of 1-[N-(t-butoxycarbonyl)piperidinyl-4-oxy]-4-nitrobenzene as a pale yellow solid. An additional 3.20 g of product was extracted from the brown solid; MS (Cl) [M+Na]$^+$ 345.

1-[4-(N-t-Butoxycarbonyl)piperidinyl-4-oxy]-4-aminobenzene:

To 6.97 g (21.62 mmol) of 1-[N-(t-butoxycarbonyl)piperidinyl-4-oxy]-4-nitrobenzene in 250 mL MeOH was added 6.81 g (108.1 mmol) ammonium formate and a catalytic amount of 10% Pd/C, and the reaction heated at 50° C. under $N_2$ for 5 h. The reaction was filtered through a pad of celite and the filtrate evaporated to afford crude aniline as an orange oil. The material was used without further purification in the next step.

1-{N-(t-Butoxcarbonyl)piperidinyl-4-oxy}-4-(phenylmethoxcarbonylamino)benzene:

To 6.32 g (21.62 mmol) of 1-[4-(N-t-butoxycarbonyl)piperidinyl-4-oxy]-4-aminobenzene in 300 mL 2:1 acetone:$H_2O$ at 0° C. was added 4.50 g (52.97 mmol) $NaHCO_3$ and 3.30 mL (23.13 mmol) benzylchloroformate. The reaction was allowed to warm to rt and stirred overnight. Then the volatiles were evaporated, the residue diluted with 200 mL $H_2O$ and extracted with $Et_2O$ (2×200 mL). The combined organic layers were washed with $H_2O$, dried over $MgSO_4$, filtered, and the solvent removed by rotary evaporation to give 8.62 g (93%) of 4-{N-(t-butoxycarbonyl)piperidinyl-4-oxy}-1-(phenylmethoxycarbonylamino)benzene as a pink solid; mp 107–108° C., MS (Cl) [M+Na]$^+$ 449.

(R)-[3-[4-{N-(t-Butoxycarbonyl)piperidinyl-4-oxy}phenyl]-2-oxo-5-oxazolidinyl]methanol:

To 8.23 g (19.31 mmol) of 4-{N-(t-butoxycarbonyl)piperidinyl-4-oxy}-1-(phenylmethoxycarbonylamino)benzene in 300 mL dry THF at −78° C. was added 10.8 mL (27.03 mmol) 2.5M n-BuLi and the reaction stirred for 1 h. Then 3.84 mL (27.03 mmol) (R)-glycidyl butyrate was added via syringe and the reaction warmed to rt and stirred for 3 days. Then an additional 2 mL 2.5M n-BuLi was added and the reaction stirred for another day. The reaction was carefully poured into 150 mL sat. $NH_4Cl$ (aq.) and extracted with EtOAc (3×100 mL). The combined organic layers were washed with $H_2O$, dried over $MgSO_4$, filtered, and the solvent removed by rotary evaporation. Silica gel chromatography (EtOAc) gave 4.34 g (57%) of (R)-[3-[4-{N-(t-butoxycarbonyl)piperidinyl-4-oxy}phenyl]-2-oxo-5-oxazolidinyl]methanol as a yellow solid; mp 110–1 12° C., MS (Cl) [M+Na]$^+$415.

(R)-[3-[4-{N-(t-Butoxycarbonyl)piperidinyl-4-oxy}phenyl]-2-oxo-5-oxazolidinyl]methyl Methanesulfonate:

To 4.23 g (10.79 mmol) of (R)-[3-[4-{N-(t-butoxycarbonyl)piperidinyl-4-oxy}phenyl]-2-oxo-5-oxazolidinyl]methanol in 75 mL $CH_2Cl_2$ at 0° C. was added 3.0 mL (21.58 mmol) $NEt_3$ and 1.2 mL (15.11 mmol) methanesulfonyl chloride. The reaction was allowed to warm to rt over an hour and washed with $H_2O$ (2×50 mL), dried over $MgSO_4$, filtered, and the solvent removed by rotary evaporation to yield 5.0 g (99%) of (S)-[3-[4-{N-(t-butoxycarbonyl)piperidinyl-4-oxy}phenyl]-2-oxo-5-oxazolidinyl]methyl methanesulfonate as a white foam.

(R)-[3-[4-{N-(t-Butoxycarbonyl)piperidinyl-4-oxy}phenyl]-2-oxo-5-oxazolidinyl]methylazide:

To a solution of 5.0 g (10.63 mmol) of (R)-[3-[4-{N-(t-butoxycarbonyl)piperidinyl-4-oxy}phenyl]-2-oxo-5-oxazolidinyl]methyl methanesulfonate in 100 mL DMF was added 2.63 g (40.38 mmol) sodium azide and the reaction was heated at 70° C. overnight. Then the reaction was poured into 200 mL $H_2O$ and extracted with EtOAc (3×150 mL). The combined organic layers were washed with $H_2O$ (2×150 mL), dried over $MgSO_4$, filtered, and the solvent removed by rotary evaporation to yield 4.4 g (99%) of (R)-[3-[4-{N-(t-butoxycarbonyl)piperidinyl-4-oxy}phenyl]-2-oxo-5-oxazolidinyl]methylazide as a yellow oil; MS (Cl) [M+Na]$^+$440.

(S)-N-[[3-[4-{N-(t-Butoxycarbonyl)piperidinyl-4-oxy}phenyl]-2-oxo-5-oxazolidinyl]methyl]acetamide:

A solution of 4.48 g (10.73 mmol) of (R)-[3-[4-{N-(t-Butoxycarbonyl)piperidinyl-4-oxy}phenyl]-2-oxo-5-oxazolidinyl]methylazide in 30 mL of EtOAc was treated with a catalytic amount of 10% Pd/C, followed by hydrogenation at 50 psi for 20 h. To this mixture at 0° C. was added 1.1 mL (12.88 mmol) pyridine and 3.2 mL (34.34 mmol) acetic anhydride. The reaction was stirred for 30 min at 0° C., then warmed to rt over 1 h. The reaction was filtered through celite, eluting with EtOAc. The volatiles were removed under reduced pressure and the yellow solid dissolved in EtOAc and washed with $H_2O$ (3×100 mL). A white solid was removed via filtration. The organic layers were concentrated to an orange oil and triturated using EtOAc and hexanes to yield a white solid. The white solids were combined to yield 1.48 g (31%) of (S)-N-[[3-[4-{N-(t-butoxycarbonyl)piperidinyl-4-oxy}phenyl]-2-oxo-5-oxazolidinyl]methyl]acetamide; mp 185–186° C., MS (Cl) [M+Na]$^+$ 456.

(S)-N-[[3-[4-{Piperidinyl-4-oxy}phenyl]-2-oxo-5-oxazolidinyl]methyl]acetamide:

To a solution of 1.48 g (3.41 mmol) of the previous Boc-carbamate ((S)-N-[[3-[4-{N-(t-butoxycarbonyl)piperidinyl-4-oxy}phenyl]-2-oxo-5-oxazolidinyl]methyl]acetamide) in 225 mL $CH_2Cl_2$ was added 2.6 mL (34.14 mmol) trifluoroacetic acid and the reaction stirred at rt for 2 h. The reaction was diluted with 50 mL $CH_2Cl_2$, washed with $NaHCO_3$ (2×100 mL), dried over $MgSO_4$, filtered, and evaporated under reduced pressure to yield 980 mg (86%) of (S)-N-[[3-[4-{piperidinyl-4-oxy}phenyl]-2-oxo-5-oxazolidinyl]methyl]acetamide as a yellow oil.

(S)-N-[[3-[4-{N-(Benzyloxyacetyl)piperidinyl-4-oxy}phenyl]-2-oxo-5-15 oxazolidinyl]methyl]acetamide:

To a suspension of 160 mg (0.48 mmol) of (S)-N-[[3-[4-{piperidinyl-4-oxy}phenyl]-2-oxo-5-oxazolidinyl]methyl]acetamide in 20 mL $CH_2Cl_2$ was added 0.13 mL (0.96 mmol) $NEt_3$ and 0.08 ml (0.53 mmol) benzyloxyacetyl chloride. After stirring for 2 h, the reaction was poured into 75 mL $H_2O$ and extracted with $CH_2Cl_2$ (4×50 mL). The combined organic layers were dried over $MgSO_4$, filtered, and evaporated under reduced pressure. Silica gel chromatography (10% MeOH in EtOAc) afforded (S)-N-[[3-[4-{N-(benzyloxyacetyl)piperidinyl-4-oxy}phenyl]-2-oxo-5-oxazolidinyl]methyl]acetamide as a white foam; mp 53–55° C., MS (Cl) [M+H]$^+$ 482.

EXAMPLE 31

(S)-N-[[3-[4-{N-(α-Hydroxyacetyl)piperidinyl-4-oxy}phenyl]-2-oxo-5-oxazolidinyl]methyl]acetamide Compound 31

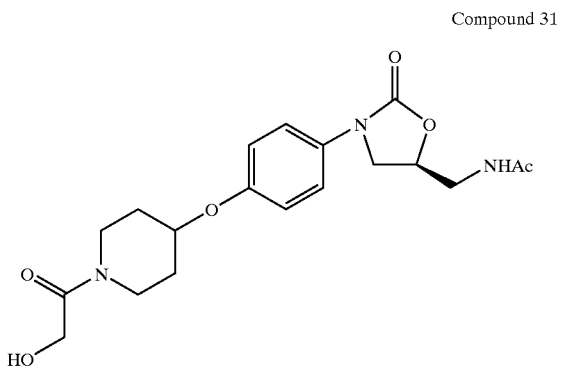

To a solution of 103 mg (0.21 mmol) of Compound 30 in 10 mL MeOH was added 67 mg (1.07 mmol) ammonium formate and a catalytic amount of 10% Pd/C, and the reaction was heated at 50° C. for 3 days. Then the reaction was filtered through a pad of celite, eluted with EtOAc and MeOH, and the solvent removed under reduced pressure to yield 56 mg (66%) of (S)-N-[[3-[4-{N-(α-hydroxyacetyl)piperidinyl-4-oxy}phenyl]-2-oxo-5-oxazolidinyl]methyl]acetamide as a white foam; MS (Cl) [M+H]$^+$ 392.

EXAMPLE 32

(S)-N-[[3-[4-{N-(Acetyl)piperidinyl-4-oxy}phenyl]-2-oxo-5-oxazolidinyl]methyl]acetamide Compound 32

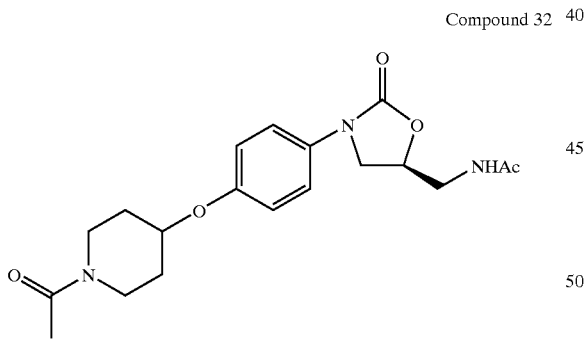

To a solution of 240 mg (0.72 mmol) of (S)-N-[[3-[4-{piperidinyl-4-oxy}phenyl]-2-oxo-5-oxazolidinyl]methyl]acetamide in 20 mL CH$_2$Cl$_2$ was added 0.45 mL (3.24 mmol) NEt$_3$ and 0.08 mL (1.08 mmol) acetyl chloride and the reaction stirred overnight. The reaction was diluted with 50 mL CH$_2$Cl$_2$, washed with H$_2$O, dried over MgSO$_4$, filtered, and the solvent removed by rotary evaporation to give the crude product as a gold oil. Purification by silica gel chromatography (10% MeOH in EtOAc) yielded 130 mg (50%) of (S)-N-[[3-[4-{N-(acetyl)piperidinyl-4-oxy}phenyl]-2-oxo-5-oxazolidinyl]methyl]acetamide as a colorless oil; MS (Cl) [M+Na]$^+$ 398.

EXAMPLE 33

(S)-N-[[3-[4-{N-(Methanesulfonyl)piperidinyl-4-oxy}phenyl]-2-oxo-5-oxazolidinyl]methyl]acetamide Compound 33

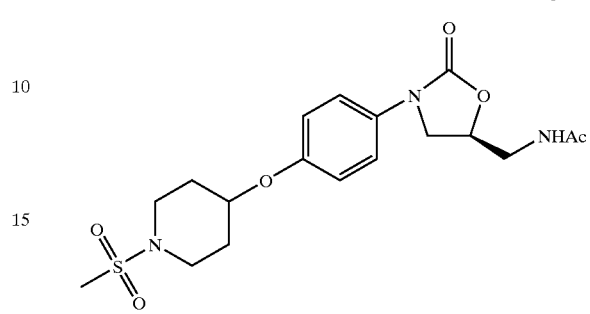

To a solution of 50 mg (0.15 mmol) of (S)-N-[[3-[4-{piperidinyl-4-5 oxy}phenyl]-2-oxo-5-oxazolidinyl]methyl]acetamide in 20 mL CH$_2$Cl$_2$ was added 0.04 mL (0.30 mmol) NEt$_3$ and 0.02mL (0.21 mmol) methanesulfonyl chloride and the reaction stirred overnight. The reaction was diluted with 10 mL CH$_2$Cl$_2$, washed with H$_2$O, dried over MgSO$_4$, filtered, and the solvent removed by rotary evaporation to give the crude product as a gold oil. Purification by silica gel chromatography (10% MeOH in EtOAc) yielded 40 mg (64%) of (S)-N-[[3-[4-{N-(methanesulfonyl)piperidinyl-4-oxy}phenyl]-2-oxo-5-oxazolidinyl]methyl]acetamide as a white solid; MS (Cl) [M+Na]$^+$ 434.

EXAMPLE 34

(S)-N-[[3-[3-Fluoro-4-{N-(t-butoxycarbonyl)piperidinyl-3-oxy}phenyl]-2-oxo-5-oxazolidinyl]methyl]acetamide Compound 34

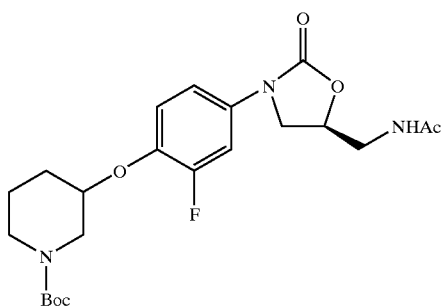

N-(t-Butoxycarbonyl)-3-piperidinol:

A solution of 10.0 g (72.67 mmol) 3-hydroxypiperidine in 100 mL dry THF at 0° C. was added 10.1 mL (72.67 mmol) NEt$_3$ and 15.86 g (72.67 mmol) di-t-butylcarbonate in 100 mL THF and the reaction allowed to warm to rt and stirred overnight. The solvent was removed under reduced pressure, the resulting residue dissolved in 300 mL CH$_2$Cl$_2$ and the solution extracted with H$_2$O (2×200 mL), dried over MgSO$_4$, filtered and rotary evaporated to yield 12.66 g (87%) of N-(t-butoxycarbonyl)-3-piperidinol as an oil which slowly solidified to a white solid.

1-[N-(t-Butoxycarbonyl)piperidinyl-3-oxy]-2-fluoro-4-nitrobenzene:

To a solution of 5.0 g (24.84 mmol) of N-(t-butoxycarbonyl)-3-piperidinol in 75 mL dry THF at 0° C.

was added dropwise 37 mL (37.26 mmol) 1M KOtBu. After stirring at 0° C. for 0.5 h, 2.8 mL (24.84 mmol) 3,4-difluoronitrobenzene was added and the reaction warmed to rt and stirred for 0.5 h. The volatiles were removed under reduced pressure and the residue was dissolved in 400 mL $H_2O$ and extracted with $CH_2Cl_2$ (2×300 mL). The combined aqueous layers were dried with $MgSO_4$, filtered, and the solvent removed by rotary evaporation. Purification by silica gel chromatography (3:1 hexanes:EtOAc) yielded 5.94 g (70%) of 1-[N-(t-butoxycarbonyl)piperidinyl-3-oxy]-2-fluoro-4-nitrobenzene; MS (Cl) $[M+Na]^+$ 363.

1-[4-(N-t-Butoxycarbonyl)piperidinyl-3-oxy]-2-fluoro-4-aminobenzene:

To 5.94 g (17.40 mmol) of 1-[N-(t-butoxycarbonyl)piperidinyl-3-oxy]-2-fluoro-4-nitrobenzene in 200 mL MeOH was added 5.49 g (87.02 mmol) ammonium formate and a catalytic amount of 10% Pd/C, and the reaction heated at 50° C. under $N_2$ overnight. The reaction was filtered through a pad of celite and the filtrate evaporated to afford crude aniline as an orange oil. The product was dissolved in 150 mL EtOAc and washed with $H_2O$ (2×100), dried over $MgSO_4$, filtered, and the solvent removed under reduced pressure to give 4.98 g (92%) as a light yellow oil. The material was used without further purification in the next step.

2-Fluoro-1-{N-(t-butoxycarbonyl)piperidinyl-3-oxy}-4-(phenylmethoxycarbonylamino)benzene:

To 4.98 g (16.08 mmol) of 1-[4-(N-t-butoxycarbonyl)piperidinyl-3-oxy]-2-fluoro-4-aminobenzene in 300 mL 2:1 acetone:$H_2O$ at 0° C. was added 3.31 g (39.40 mmol) $NaHCO_3$ and 2.46 mL (17.20 mmol) benzylchloroformate. After stirring at rt overnight the volatiles were evaporated, the residue diluted with 200 mL $H_2O$ and extracted with $Et_2O$ (3×150 mL). The combined organic layers were washed with $H_2O$, dried over $MgSO_4$, filtered, and the solvent removed by rotary evaporation. Silica gel chromatography (2:3 EtOAc:Hexanes) afforded 5.30 g (75%) of 3-fluoro-4-{N-(t-butoxycarbonyl)piperidinyl-3-oxy}-1-(phenylmethoxycarbonylamino)benzene as a white solid; mp 109–110° C., MS (Cl) $[M+Na]^+$ 467.

(R)-[3-[3-Fluoro-4-{N-(t-butoxycarbonyl)piperidinyl-3-oxy}phenyl]-2-oxo-5-oxazolidinyl]methanol:

To 3.27 g (7.36 mmol) of 2-fluoro-1-{N-(t-butoxycarbonyl)piperidinyl-3-oxy}-4-(phenylmethoxycarbonylamino)benzene in 150 mL dry THF at −78° C. was added 4.1 mL (10.31 mmol) 2.5M n-BuLi and the reaction stirred for 1 h. Then 1.5 mL (10.31 mmol) (R)-glycidyl butyrate was added via syringe and the reaction warmed to rt and stirred overnight. The reaction was carefully poured into 100 mL sat. $NH_4Cl$ (aq.) and extracted with EtOAc (3×100 mL). The combined organic layers were washed with $H_2O$, dried over $MgSO_4$, filtered, and the solvent removed by rotary evaporation. Silica gel chromatography (EtOAc) gave 2.99 g (98%) of (R)-[3-[3-fluoro-4-{N-(t-butoxycarbonyl)piperidinyl-3-oxy}phenyl]-2-oxo-5-oxazolidinyl]methanol as a white foam; mp 48–50° C.

(R)-[3-[3-Fluoro-4-{N-(t-butoxycarbonyl)piperidinyl-3-oxy}phenyl]-2-oxo-5-oxazolidinyl]methyl Methanesulfonate:

To 1.32 g (3.22 mmol) of (R)-[3-[3-fluoro-4-{N-(t-butoxycarbonyl)piperidinyl-3-oxy}phenyl]-2-oxo-5-oxazolidinyl]methanol in 50 mL $CH_2Cl_2$ at 0° C. was added 0.90 mL (6.44 mmol) $NEt_3$ and 0.35 mL (4.51 mmol) methanesulfonyl chloride. The reaction was allowed to warm to rt over 1 h and then washed with $H_2O$ (2×30 mL), dried over $MgSO_4$, filtered and the solvent removed by rotary evaporation to yield 1.50 g (95%) of (R)-[3-[3-fluoro-4-{N-(t-butoxycarbonyl)piperidinyl-3-oxy}phenyl]-2-oxo-5-oxazolidinyl]methyl methanesulfonate as a yellow foam.

(R)-[3-[3-Fluoro-4-{N-(t-butoxncarbonyl)piperidinyl-3-oxy}phenyl]-2-oxo-5-oxazolidinyl]methylazide:

To a solution of 1.50 g (3.07 mmol) of (R)-[3-[3-fluoro-4-{N-(t-butoxycarbonyl)piperidinyl-3-oxy}phenyl]-2-oxo-5-oxazolidinyl]methyl methanesulfonate in 60 mL DMF was added 758 mg (11.66 mmol) sodium azide and the reaction heated at 75° C. overnight. Then the reaction was poured into 100 mL $H_2O$ and extracted with EtOAc (3×100 mL). The combined organic layers were washed with $H_2O$ (3×200 mL), dried over $MgSO_4$, filtered, and the solvent removed by rotary evaporation to yield (R)-[3-[3-fluoro-4-{N-(t-butoxycarbonyl)piperidinyl-3-oxy}phenyl]-2-oxo-5-oxazolidinyl]methylazide as a foam.

(S)-N-[[3-[3-Fluoro-4-{N-(t-butoxycarbonyl)piperidinyl-3-oxy}phenyl]-2-oxo-5-oxazolidinyl]methyl]acetamide:

A solution of 1.34 g (3.07 mmol) of (R)-[3-[3-fluoro-4-{N-(t-butoxycarbonyl)piperidinyl-3-oxy}phenyl]-2-oxo-5-oxazolidinyl]methylazide in 30 mL of EtOAc was treated with a catalytic amount of 10% Pd/C, followed by hydrogenation at 50 psi for 20 h. To this mixture at 0° C. was added 0.3 mL (3.68 mmol) pyridine and 0.93 mL (9.82 mmol) acetic anhydride. The reaction was stirred for 30 min at 0° C., then warmed to rt over 1 h. The reaction was filtered through celite, eluting with EtOAc. The volatiles were removed under reduced pressure. Silica gel chromatography (10% MeOH in EtOAc) yielded (S)-N-[[3-[4-{N-(t-butoxycarbonyl)piperidinyl-3-oxy}phenyl]-2-oxo-5-oxazolidinyl]methyl]acetamide as a white solid; mp 60–63° C., MS (Cl) $[M+Na]^+$ 474.

EXAMPLE 35

(S)-N-[[3-[3-Fluoro-4-{N-(benzyloxyacetyl)piperidinyl-3-oxy}phenyl]-2-oxo-5-oxazolidinyl]methyl]acetamide

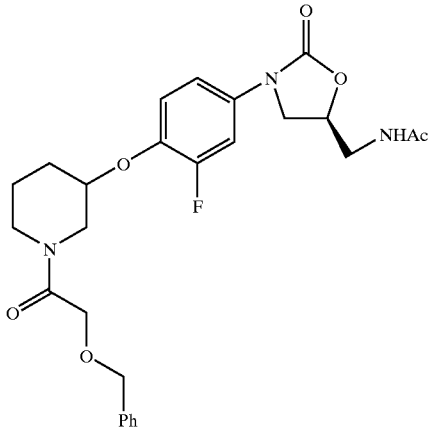

Compound 35

(S)-N-[[3-[3-Fluoro-4-{piperidinyl-3-oxy}phenyl]-2-oxo-5-oxazolidinyl]methyl]acetamide:

To a solution of 589 mg (1.31 mmol) of Compound 34 in 13 mL $CH_2Cl_2$ was added 1.0 mL (13.1 mmol) trifluoroacetic acid and the reaction stirred at rt for 2 h. The volatiles were evaporated under reduced pressure to yield (S)-N-[[3-[3-fluoro-4-{piperidinyl-3-oxy}phenyl]-2-oxo-5-oxazolidinyl]methyl]acetamide.

(S)-N-[[3-[3-Fluoro-4-{N-(benzyloxyacetyl)piperidinyl-3-oxy}phenyl]-2-oxo-5-oxazolidinyl]methyl]acetamide:

To a suspension of 303 mg (0.65 mmol) of (S)-N-[[3-[3-fluoro-4-{piperidinyl-3-oxy}phenyl]-2-oxo-5-oxazolidinyl]

methyl]acetamide in 50 mL CH$_2$Cl$_2$ was added 0.27 mL (1.96 mmol) NEt$_3$ and 0.11 mL (0.72 mmol) benzyloxyacetyl chloride. After stirring for 1 h, the reaction was poured into 75 mL H$_2$O and extracted with CH$_2$Cl$_2$ (4×50 mL). The combined organic layers were dried over MgSO$_4$, filtered, and evaporated under reduced pressure to yield (S)-N-[[3-[3-fluoro-4-{N-(benzyloxyacetyl)piperidinyl-3-oxy}phenyl]-2-oxo-5-oxazolidinyl]methyl]acetamide as a foam; MS (Cl) [M+H]$^+$ 500.

EXAMPLE 36

(S)-N-[[3-[3-Fluoro-4-{N-(α-hydroxyacetyl)piperidinyl-3-oxy}phenyl]-2-oxo-5-oxazolidinyl]methyl]acetamide

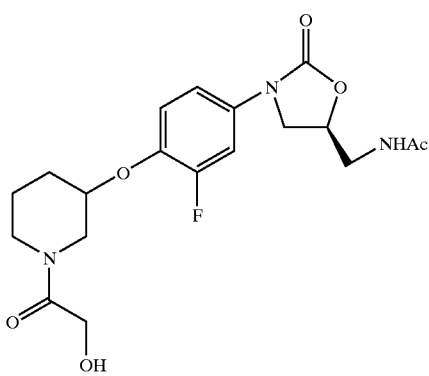

Compound 36

To a solution of 301 mg (0.60 mmol) of Compound 35 in 10 mL MeOH was added 190 mg ammonium formate and a catalytic amount of 10% Pd/C and the reaction was heated at reflux overnight. Then the reaction was filtered through a pad of celite and the solvent removed under reduced pressure. Silica gel chromatography (1 0% MeOH in EtOAc) afforded 231 mg (82%) of (S)-N-[[3-[3-fluoro-4-{N-(α-hydroxyacetyl)piperidinyl-3-oxy}phenyl]-2-oxo-5-oxazolidinyl]methyl]acetamide as a yellow foam; MS (Cl) [M+H]$^+$ 410.

EXAMPLE 37

(S)-N-[[3-[3-Fluoro-4-{N-(acetyl)piperidinyl-3-oxy}phenyl]-2-oxo-5-oxazolidinyl]methyl]acetamide

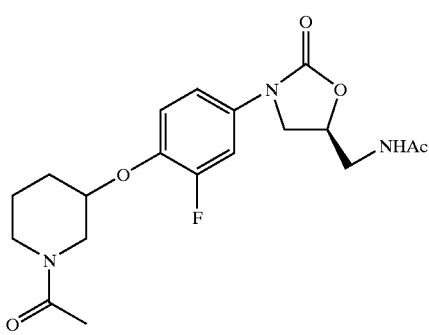

Compound 37

To a solution of 100 mg (0.28 mmol) of (S)-N-[[3-[3-fluoro-4-{piperidinyl-3-oxy}phenyl]-2-oxo-5-oxazolidinyl]methyl]acetamide in 10 mL CH$_2$Cl$_2$ was added 0.12 mL (0.85 mmol) NEt$_3$ and 0.03 mL (0.43 mmol) acetyl chloride. The reaction stirred at rt for 2 h diluted with CH$_2$Cl$_2$, washed with H$_2$O (2×100 mL), dried over MgSO$_4$, filtered, and the solvent removed by rotary evaporation to yield the impure amide. Purification by silica gel chromatography (10% MeOH in EtOAc) and trituration of the resultant oil with EtOAc and hexanes yielded (S)-N-[[3-[3-fluoro-4-{N-(acetyl)piperidinyl-3-oxy}phenyl]-2-oxo-5-oxazolidinyl]methyl]acetamide as a solid.

EXAMPLE 38

(S)-N-[[3-[3-Fluoro-4-{N-(2-pyrimidinyl)piperidinyl-3-oxy}phenyl]-2-oxo-5-oxazolidinyl]methyl]acetamide

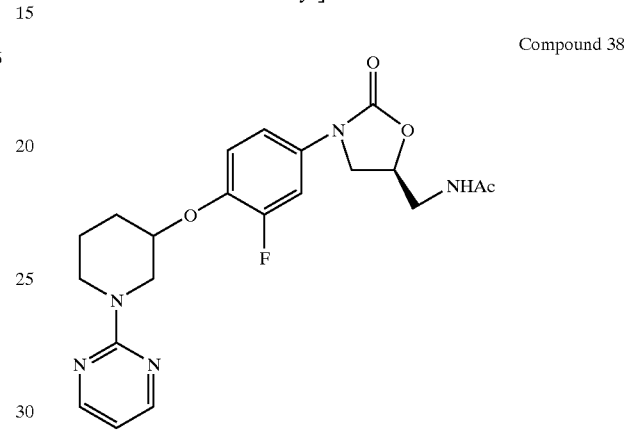

Compound 38

To a solution of 151 mg (0.33 mmol) of (S)-N-[[3-[3-fluoro-4-{piperidinyl-3-oxy}phenyl]-2-oxo-5-oxazolidinyl]methyl]acetamide in 4 mL EtOH was added 0.11 mL (0.82 mmol) NEt$_3$ and 39 mg (0.34 mmol) 2-chloropyrimidine and the reaction heated at reflux for 3 days. The reaction was cooled, poured into 15 mL NaHCO$_3$ (sat.), extracted with CH$_2$Cl$_2$, washed with H$_2$O (2×100 mL), dried over MgSO$_4$, filtered, and the solvent removed by rotary evaporation to yield an orange oil. The crude oil was triturated with EtOAc and Et$_2$O to give 25mg (23%) of (S)-N-[[3-[3-fluoro-4-{N-(2-pyrimidinyl)piperidinyl-3-oxy}phenyl]-2-oxo-5-10 oxazolidinyl]methyl]acetamide as a pale orange solid; mp 130–131° C., MS (Cl) [M+H]$^+$ 429.

EXAMPLE 39

(S)-N-[[3-[3-Fluoro-4-{N-(benzyloxyacetyl)pyrrolidinyl-3-oxy}phenyl]-2-oxo-5-oxazolidinyl]methyl]acetamide

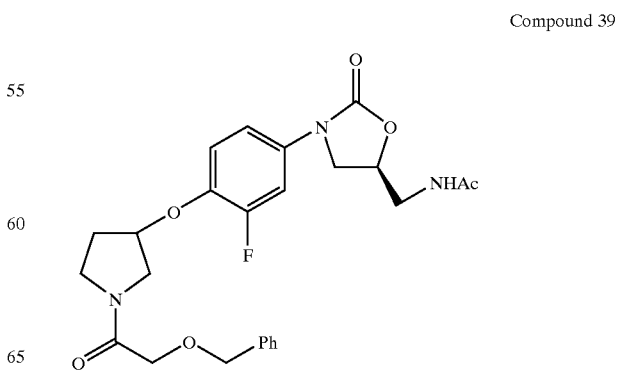

Compound 39

N-(Benzyloxyacetyl)-3-pyrrolidinol:

A solution of 4.4 mL (52.93 mmol) 3-pyrrolidinol in 250 mL CH$_2$Cl$_2$ at 0° C. was added 8.4 mL (60.26 mmol) NEt$_3$ and 8.2 mL (51.97 mmol) benzyloxyacetyl chloride. The reaction was stirred for 3.5 h and then poured into 400 mL H$_2$O. The reaction was extracted with CH$_2$Cl$_2$, dried over MgSO$_4$, filtered and rotary evaporated to yield 12.0 g (98%) of N-(benzyloxyacetyl)-3-pyrrolidinol as a yellow oil.

1-[N-(Benzyloxyacetyl)pyrrolidinyl-3-oxy]-2-fluoro-4-nitrobenzene:

To a solution of 2.03 g (8.63 mmol) of N-(benzyloxyacetamide)-3-pyrrolidinol in 50 mL dry THF at 0° C. was added dropwise 10 mL (10.0 mmol) 1M KOtBu. After stirring at 0° C. for 0.5 h, 0.96 mL (8.67 mmol) 3,4-difluoronitrobenzene was added and the reaction warmed to rt and stirred overnight. The reaction was poured into 100 mL H$_2$O and extracted with EtOAc. The combined organic layers were washed with H$_2$O, dried with MgSO$_4$, filtered, and the solvent removed by rotary evaporation. Then the solid was recrystallized from EtOAc and hexanes to afford 2.49 g (77%) of 1-[N-(benzyloxyacetyl) pyrrolidinyl-3-oxy]-2-fluoro-4-nitrobenzene as a solid. ps 1-[4-(N-Benzyloxyacetyl)pyrrolidinyl-3-oxy]-2-fluoro-4-aminobenzene:

To 1.61 g (4.31 mmol) of 1-[N-(benzyloxyacetamide) pyrrolidinyl-3-oxy]-2-fluoro-4-nitrobenzene in 50 mL EtOH was added 4.86 g (21.5 mmol) SnCl$_2$ and the reaction heated at 70° C. for 2 h. The reaction was poured into ice water and extracted with EtOAc and CHCl$_3$ (2×100 mL). The combined organic layers were dried over MgSO$_4$, filtered, and the solvent removed under reduced pressure to give 880 mg (58%) of 1-[4-(N-benzyloxyacetamide)pyrrolidinyl-3-oxy]-2-fluoro-4-aminobenzene as a yellow oil. The material was used without further purification in the next step.

2-Fluoro-1-{N-(benzyloxyacetyl)pyrrolidinyl-3-oxy}-4-(phenylmethoxycarbonylamino)benzene:

To 466 mg (2.73 mmol) of 1-[4-(N-benzyloxyacetyl) pyrrolidinyl-3-oxy]-2-fluoro-4-aminobenzene in 75 mL 2:1 acetone:H$_2$O at 0° C. was added 527 mg (6.27 mmol) NaHCO$_3$ and 0.88 mL (2.56 mmol) Cbz-Cl. The reaction was allowed to warm to rt and stirred overnight. The volatiles were evaporated, the residue diluted with 200 mL H$_2$O and extracted with EtOAc (3×100 mL). The combined organic layers were washed with H$_2$O, dried over MgSO$_4$, filtered, and the solvent removed by rotary evaporation. Silica gel chromatography (EtOAc) afforded 473 mg (38%) of 3-fluoro-4-{N-(benzyloxyacetyl)pyrrolidinyl-3-oxy}-1-(phenylmethoxycarbonylamino); MS (Cl) [M+H]$^+$ 479.

(R)-[3-[3-Fluoro-4-{N-(benzyloxyacetyl)pyrrolidinyl-3-oxy}phenyl]-2-oxo-5-oxazolidinyl]methanol:

To 473 mg (0.99 mmol) of 2-fluoro-1-{N-(benzyloxyacetyl)pyrrolidinyl-3-oxy}-4-(phenylmethoxycarbonylamino)benzene in 25 mL dry THF at −78° C. was added 0.55 mL (1.38 mmol) 2.5M n-BuLi and the reaction warmed to rt and stirred for 1 h. Then the solution was again cooled to −78° C. and 0.19 mL (1.38 mmol) (R)-glycidyl butyrate was added via syringe and the reaction warmed to rt and stirred overnight. The reaction was carefully poured into 50 mL sat. NH$_4$Cl (aq.) and extracted with EtOAc (3×50 mL). The combined organic layers were washed with H$_2$O, dried over MgSO$_4$, filtered, and the solvent removed by rotary evaporation. Silica gel chromatography (0% to 10% MeOH in EtOAc) gave 107 mg (25%) of (R)-[3-[3-Fluoro-4-{N-(benzyloxyacetyl) pyrrolidinyl-3-oxy}phenyl]-2-oxo-5-oxazolidinyl]methanol as a gold oil; MS (Cl) [M+Na]$^+$ 445.

(R)-[3-[3-Fluoro-4-{N-(benzyloxyacetyl)pyrrolidinyl-3-oxy}phenyl]-2-oxo-5-oxazolidinyl]methyl Methanesulfonate:

To 107 mg (0.24 mmol) of (R)-[3-[3-fluoro-4-{N-(benzyloxyacetyl)pyrrolidinyl-3-oxy}phenyl]-2-oxo-5-oxazolidinyl]methanol in 50 mL CH$_2$Cl$_2$ at 0° C. was added 0.07 mL (0.48 mmol) NEt$_3$ and 0.03 mL (0.34 mmol) methanesulfonyl chloride. After warming to rt and stirring for 1 h the reaction was diluted with 10 mL CH$_2$Cl$_2$, washed with H$_2$O, dried over MgSO$_4$, filtered and the solvent removed by rotary evaporation to yield (R)-[3-[3-fluoro-4-{N-(benzyloxyacetyl)pyrrolidinyl-3-oxy}phenyl]-2-oxo-5-oxazolidinyl]methyl methanesulfonate; MS (Cl) [M+H]$^+$ 523.

(R)-[3-[3-Fluoro-4-{N-(benzyloxyacetyl)pyrrolidinyl-3-oxy}phenyl]-2-oxo-5-oxazolidinyl]methylazide:

To a solution of 2.22 g (4.25 mmol) of (R)-[3-[3-fluoro-4-{N-(benzyloxyacetyl)pyrrolidinyl-3-oxy}phenyl]-2-oxo-5-oxazolidinyl]methyl methanesulfonate in 40 mL DMF was added 1.05 g (16.13 mmol) sodium azide and the reaction heated at 75° C. overnight. Then the reaction was poured into 20 mL H$_2$O and extracted with EtOAc (3×100 mL). The combined organic layers were washed with H$_2$O, dried over Na$_2$SO$_4$, filtered, and the solvent removed by rotary evaporation to yield 1.29 g (65%) of (R)-[3-[3-Fluoro-4-{N-(benzyloxyacetyl)pyrrolidinyl-3-oxy}phenyl]-2-oxo-5-oxazolidinyl]methylazide; MS (Cl) [M+H]$^+$ 471.

(S)-N-[[3-[3-Fluoro-4-{N-(benzyloxyacetyl)pyrrolidinyl-3-oxy}phenyl]-2-oxo-5-oxazolidinyl]methyl]acetamide (Compound 39):

To a solution of 1.29 g (2.74 mmol) of (R)-[3-[3-fluoro-4-{N-(benzyloxyacetyl)pyrrolidinyl-3-oxy}phenyl]-2-oxo-5-oxazolidinyl]methylazide in 30 mL MeOH was added 1.38 mL (13.71 mmol) 1,3-propanedithiol and 1.91 mL (13.71 mmol) NEt$_3$and the reaction stirred overnight at rt. Then 0.78 mL (8.23 mmol) acetic anhydride and 1.33 mL (16.45 mmol) pyridine were added and the reaction stirred at rt for 3 h. The reaction was filtered through a fritted funnel, rinsed with MeOH, and concentrated under reduced pressure. Then the residue was diluted with EtOAc, washed with H$_2$O (3×100 mL), washed with brine, dried over Na$_2$SO$_4$, and the solvent removed under reduced pressure to give an orange oil. Purification by silica gel chromatography (10% MeOH in EtOAc) gave 1.02 g (77%) of (S)-N-[[3-[3-fluoro-4-{N-(benzyloxyacetyl)pyrrolidinyl-3-oxy}phenyl]-2-oxo-5-oxazolidinyl]methyl]acetamide as a white foam; mp 53–55° C., MS (Cl) [M+H]$^+$ 486.

EXAMPLE 40

(S)-N-[[3-[3-Fluoro-4-{N-(α-hydroxyacetyl) pyrrolidinyl-3-oxy}phenyl]-2-oxo-5-oxazolidinyl] methyl]acetamide

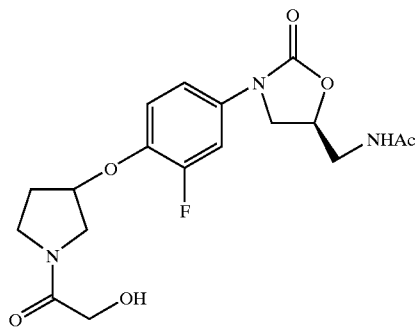

Compound 40

To a solution of 695 mg (1.43 mmol) of Compound 39 in 40 mL MeOH was added 451 mg (7.17 mmol) ammonium formate and a catalytic amount of 10% Pd/C, and the reaction was heated at reflux overnight. Then the reaction was filtered through a pad of celite and the solvent removed under reduced pressure. Trituration with EtOAc, MeOH, and hexanes afforded 363 mg (64%) of (S)-N-[[3-[3-fluoro-4-{N-(α-hydroxyacetyl)pyrrolidinyl-3-oxy}phenyl]-2-oxo-5-oxazolidinyl]methyl]acetamide as a white powder; mp 97–99° C., MS (Cl) [M+H]+ 396.

EXAMPLE 41

(5S)-3-[6-{N-(t-Butoxycarbonyl)piperidinyl-4-oxy}-pyridin-3-yl]-5-methylacetamide-oxazolidin-2-one Compound 41

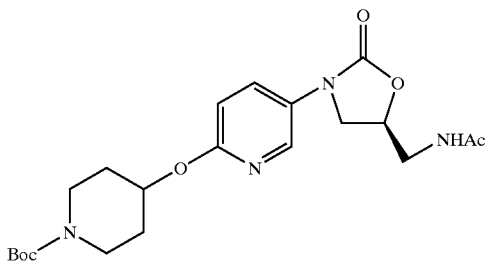

2-[N-(t-Butoxycarbonyl)piperdinyl-4-oxy]-5-nitropyridine:

To a solution of 15.23 g (75.7 mmol) N-(t-butoxycarbonyl)-4-piperidinol in 450 mL THF at 0° C. was added 126 mL (126 mmol) KOtBu and the reaction stirred for 40 min. Then 10.0 g (63 mmol) 2-chloro-5-nitropyridine was added and the reaction warmed to rt and stirred overnight. The reaction was diluted with H₂O, extracted with Et₂O, dried over MgSO₄, filtered, and the solvent removed under reduced pressure to yield the crude product as a black oil. Purification by silica gel chromatography (1:1 EtOAc:hexanes) gave the desired product; MS (Cl) [M+H]+ 324.

2-[N-(t-Butoxycarbonyl)piperdinyl-4-oxy]-5-aminopyridine:

A solution of 280 mg (0.87 mmol) of 2-[N-(t-butoxycarbonyl)piperdinyl-4-oxy]-5-nitropyridine in 30 mL of EtOH was treated with a catalytic amount of 10% Pd/C, followed by hydrogenation at 50 psi overnight. The suspension was filtered through celite and the filtrate evaporated under reduced pressure to afford crude amine as a dark solid; MS (Cl) [M+H]+ 294.

2-{N-(t-Butoxycarbonyl)piperdinyl-4-oxy}-5-(phenylmethoxycarbonylamino)pyridine:

To a solution of 5.4 g (18.4 mmol) of 2-[N-(t-butoxycarbonyl)piperdinyl-4-oxy]-5-aminopyridine in 300 mL 1:1 THF:H₂O was added 7.18 g (22.1 mmol) cesium carbonate and 3.16 mL (22.1 mmol) benzylchloroformate and the reaction stirred at rt overnight. The mixture was diluted with H₂O, extracted with EtOAc, dried over MgSO₄, filtered, and the solvent removed under reduced pressure to give a dark solid. Purification by silica gel chromatography (4:1 hexanes:EtOAc) yielded 6.5 g (83%) of the carbamate as a yellow solid; MS (Cl) [M+H]+ 428.

(R)-[3-[6-{N-(t-Butoxycarbonyl)piperdinyl-4-oxy}pyridin-3-yl]-2-oxo-5-oxazolidinyl]methanol:

A solution of 5.17 g (12.1 mmol) of 2-{N-(t-butoxycarbonyl)piperdinyl-4-10 oxy}-5-(phenylmethoxycarbonylamino)pyridine in 250 mL THF was cooled to −78° C. and 5.32 mL (13.3 mmol) 2.5 M nBuLi was added and the solution stirred for 1 h. Then 1.89 mL (13.3 mmol) R-glycidyl butyrate was added and the reaction allowed to warm to rt and stirred overnight. The reaction was quenched with H₂O, extracted with Et₂O, dried over MgSO₄, filtered, and the solvent removed under reduced pressure to yield 4.22 g (88%) of the alcohol as a brown oil; MS (Cl) [M+H]+ 394.

(R)-[3-[4-{N-(t-Butoxycarbonyl)piperdinyl-4-oxy}pyridin-3-yl]-2-oxo-5-oxazolidinyl]methylmethanesulfonate:

To a solution of 4.22 g (10.7 mmol) of (R)-[3-[6-{N-(t-butoxycarbonyl)piperdinyl-4-oxy}pyridin-3-yl]-2-oxo-5-oxazolidinyl]methanol in 100 mL CH₂Cl₂ at 0° C. was added 2.99 mL (21.4 mmol) NEt₃ and the reaction stirred for 45 min. Then 1.16 mL (15.0 mmol) methanesulfonylchloride was added and the reaction stirred at rt overnight. The reaction was quenched with H₂O, extracted with CH₂Cl₂, dried over MgSO₄, filtered, and the solvent removed under reduced pressure to yield the mesylate as a brown solid.

(R)-[3-[4-{N-(t-Butoxycarbonyl)piperdinyl-4-oxy}pyridin-3-yl]-2-oxo-5-oxazolidinyl]methylazide:

To a solution of (R)-[3-[6-{N-(t-butoxycarbonyl)piperdinyl-4-oxy}pyrid-3-yl]-2-oxo-5-oxazolidinyl]methylmethanesulfonate (10.7 mmol) in 100 mL DMF was added 2.78 g (42.8 mmol) sodium azide and the reaction heated at 75° C. for 5 h.

The reaction was cooled and the solvent removed under reduced pressure. The residue was diluted with H₂O, extracted with EtOAc, dried over MgSO₄, filtered, and the solvent removed under reduced pressure to yield a brown oil which was used crude in the next reaction.

(5S)-3-[6-{N-(t-Butoxycarbonyl)piperidinyl-4-oxy}-pyridin-3-yl]-5-methylacetamide-oxazolidin-2-one (Compound 41):

A solution of 3.3 g (7.9 mmol) of (R)-[3-[6-{N-(t-butoxycarbonyl)piperdinyl-4-oxy}pyridin-3-yl]-2-oxo-5-oxazolidinyl]methylazide in 30 mL of EtOAc was treated with a catalytic amount of 10% Pd/C, followed by hydrogenation at 50 psi overnight. The suspension was filtered through celite and the filtrate evaporated under reduced pressure to afford crude amine as a dark solid. The crude reaction mixture was treated with 0.47 mL (5.8 mmol) pyridine and 2.39 mL (25 mmol) acetic anhydride and stirred overnight at rt. The volatiles were removed under reduced pressure to give a brown oil. Purification by silica gel chromatography (5% MeOH in EtOAc) yielded 1.7 g of (5S)-3-[6-{N-(t-butoxycarbonyl)piperidinyl-4-oxy}-pyridin-3-yl]-5-methylacetamide-oxazolidin-2-one as a white foam; mp 99–101° C., MS (Cl) [M+H]+ 435.

EXAMPLE 42

(5S)-3-[6-{N-(Benzyloxyacetyl)piperidinyl-4-oxy}-pyridin-3-yl]-5-methylacetamide-oxazolidin-2-one Compound 42

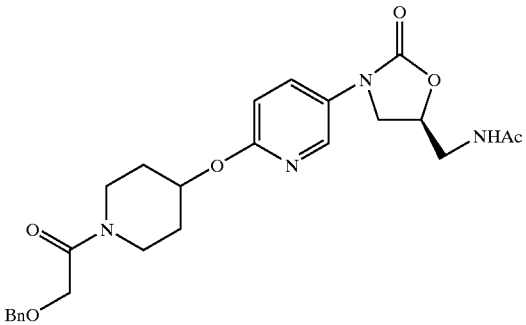

(S)-3-[6-{N-(Piperdinyl-4-oxy)pyridin-3-yl}-2-oxo-5-oxazolidinyl]methyl]acetamide:

To a solution of 500 mg (1.1 mmol) of Compound 41 in 50 mL CH$_2$Cl$_2$ was added 0.88 mL (11.2 mmol) trifluoroacetic acid and the reaction stirred at rt for 3 days. The volatiles were removed under reduced pressure to give the TFA salt as a brown oil.

(5S)-3-[6-{N-(Benzyloxyacetyl)piperidinyl-4-oxy}-pyridin-3-yl]-5-methylacetamide-oxazolidin-2-one (Compound 42):

A solution of 99 mg (0.18 mmol) of (R)-3-[6-{N-(piperdinyl-4-oxy)pyridin-3-yl}-2-oxo5-oxazolidinyl]methyl]acetamide in 20 mL CH$_2$Cl$_2$ was treated with 0.12 mL (0.88 mmol) NEt$_3$ and the reaction stirred at rt for 30 min. Then 0.06 mL (0.36 mmol) benzoxyacetylchloride was added and the reaction stirred overnight. Then 100 mg of PS-Trisamine was added and the suspension stirred for 30 min. The reaction was filtered, quenched with 10 mL H$_2$O, extracted with CH$_2$Cl$_2$ (2×20 mL), dried over MgSO$_4$, and the solvent removed by rotary evaporation to give 31 mg of (5S)-3-[6-{N-(benzyloxyacetyl)piperidinyl-4-oxy}-pyridin-3-yl]-5-methylacetamide-oxazolidin-2-one as a tan semi-solid. $^1$H NMR (CDCl$_3$) δ 8.13 (s, 1H); 7.98 (m, 1H); 7.35 (m, 5H); 6.72 (m, 1H); 6.59 (m, 1H); 5.25 (m, 1H); 4.82 (m, 1H); 4.61 (s, 2H); 4.24 (s, 2H); 3.90 (m, 1H); 3.77 (m, 2H); 3.70 (m, 1H); 3.68 (m, 2H); 3.54 (m, 1H); 3.41 (m, 1H); 2.08 (s, 3H); 2.05 (m, 2H); and 1.83 (m, 2H).

EXAMPLE 43

(5S)-3-[6-{N-(Acetyl)piperidinyl-4-oxy}-pyridin-3-yl]-5-methylacetamide-oxazolidin-2-one

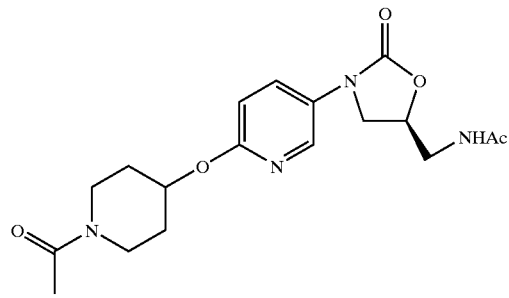

Compound 43

Compound 43 was prepared from 71 mg (0.13 mmol) of the TFA salt from Example 42, 0.09 mL (0.63 mmol) NEt$_3$, and 0.02 mL (0.26 mmol) acetyl chloride as described above to give 20 mg of (5S)-3-[6-{N-(acetyl)piperidinyl-4-oxy}-pyridin-3-yl]-5-methylacetamide-oxazolidin-2-one as a white semi-solid. $^1$H NMR (CDCl$_3$) δ 8.14 (m, 1H); 7.95 (m, 1H); 6.77 (s, 1H); 6.76 (brs, 1H); 5.25 (m, 1H); 4.83 (m, 1H); 4.06 (m, 1H); 3.91 (m, 1H); 3.80 (m, 1H); 3.68 (m, 3H); 3.4–3.6 (m, 2H); 2.15 (s, 3H); 2.04 (s, 3H); 2.02 (m, 2H); and 1.77 (m, 2H).

EXAMPLE 44

(5S)-3-[6-{N-(Methanesulfonyl)piperidinyl-4-oxy}-pyridin-3-yl]-5-methylacetamide-oxazolidin-2-one

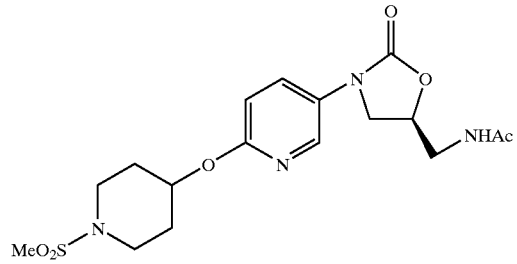

Compound 44

Compound 44 was prepared from 56 mg (0.10 mmol) of the TFA salt from Example 42, 0.07 mL (0.50 mmol) NEt$_3$, and 0.02 mL (0.20 mmol) methanesulfonyl chloride as described above to give 17 mg of (5S)-3-[6-{N-(methanesulfonyl)piperidinyl-4-oxy}-pyridin-3-yl]-5-methylacetamide-oxazolidin-2-one as a white solid; mp 175–176° C., MS (Cl) [M+H]$^+$ 413.

EXAMPLE 45

(5S)-3-[6-{N-(4-Cyanobenzoyl)piperidinyl-4-oxy}-pyridin-3-yl]-5-methylacetamide-oxazolidin-2-one

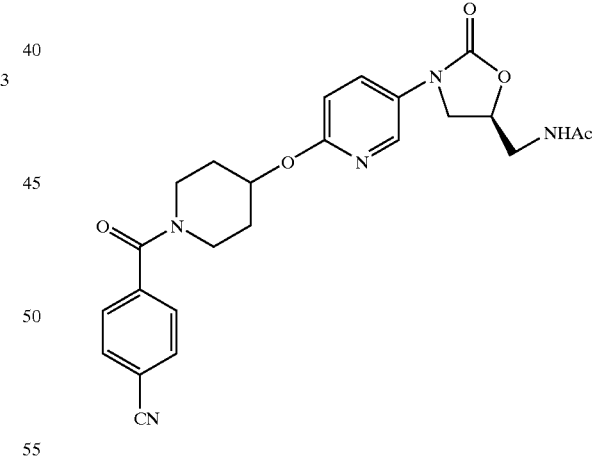

Compound 45

Compound 45 was prepared from 39 mg (0.07 mmol) of the TFA salt from Example 42, 0.05 mL (0.35 mmol) NEt$_3$, and 23 mg (0.14 mmol) 4-cyanobenzoyl chloride as described above to give 30 mg of (5S)-3-[6-{N-(4-cyanobenzoyl)piperidinyl-4-oxy}-pyridin-3-yl]-5-methylacetamide-oxazolidin-2-one as a white semi-solid. $^1$H NMR (CDCl$_3$) δ 8.13 (m, 1H); 7.97 (m, 1H); 7.69 (m, 2H); 7.57 (m, 2H); 6.78 (m, 1H); 6.48 (brt, 1H); 5.34 (m, 1H); 4.82 (m, 1H); 4.18 (m, 2H); 3.5–3.8 (m, 5H); 3.37 (m, 1H); 2.03 (s, 3H); 1.97 (m, 2H); and 1.82 (m, 2H).

EXAMPLE 46

(5S)-3-[6-{N-(Benzoyl)piperidinyl-4-oxy}-pyridin-3-yl]-5-methylacetamide-oxazolidin-2-one Compound 46

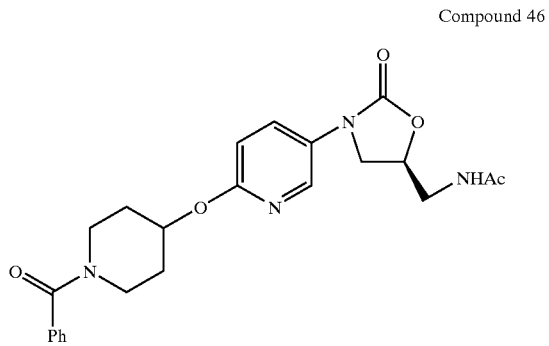

Compound 46 was prepared from 48 mg (0.09 mmol) of the TFA salt from Example 42, 0.06 mL (0.43 mmol) NEt$_3$, and 0.02 mL (0.20 mmol) benzoyl chloride as described above to give 50 mg of (5S)-3-[6-{N-(benzoyl)piperidinyl-4-oxy}-pyridin-3-yl]-5-methylacetamide-oxazolidin-2-one as a yellow solid; mp 180–182° C., MS (Cl) [M+H]$^+$ 439.

EXAMPLE 47

(5S)-3-[6-{N-(3-Fluorobenzoyl)piperidinyl-4-oxy}-pyridin-3-yl]-5-methylacetamide-oxazolidin-2-one Compound 47

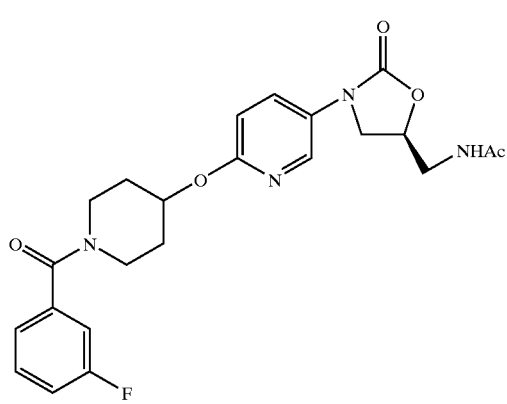

Compound 47 was prepared from 50 mg (0.12 mmol) of the TFA salt from Example 42, 0.08 mL (0.60 mmol) NEt$_3$, and 0.03 mL (0.24 mmol) 3-fluorobenzoyl chloride as described above to give 20 mg of (5S)-3-[6-{N-(3-fluorobenzoyl)piperidinyl-4-oxy}-pyridin-$^3$-yl]-5-methylacetamide-oxazolidin-2-one as a clear oil; MS (Cl) [M+H]$^+$ 457.

EXAMPLE 48

(5S)-3-[6-{N-(3-Methoxybenzoyl)piperidinyl-4-oxy}-pyridin-3-yl]-5-methylacetamide-oxazolidin-2-one Compound 48

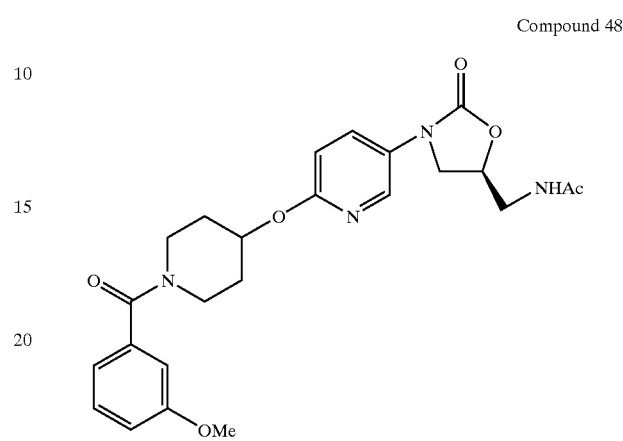

Compound 48 was prepared from 50 mg (0.12 mmol) of the TFA salt from Example 42, 0.08 mL (0.60 mmol) NEt$_3$, and 0.03 mL (0.24 mmol) 3-methoxybenzoyl chloride as described above to give 20 mg of (5S)-3-[6-{N-(3-methoxybenzoyl)piperidinyl-4-oxy}-pyridin-3-yl]-5-methylacetamide-oxazolidin-2-one as a yellow oil; MS (Cl) [M+H]$^+$ 468.

EXAMPLE 49

(5S)-3-[6-{N-(Dimethylcarbamoyl)piperidinyl-4-oxy}-pyridin-3-yl]-5-methylacetamide-oxazolidin-2-one Compound 49

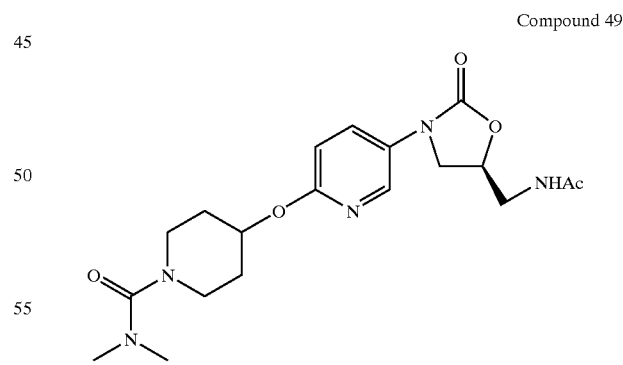

Compound 49 was prepared from 50 mg (0.12 mmol) of the TFA salt from Example 42, 0.08 mL (0.60 mmol) NEt$_3$, and 0.02 mL (0.24 mmol) dimethylcarbamoyl chloride as described above to give 17 mg of (5S)-3-[6-{N-(dimethylcarbamoyl)piperidinyl-4-oxy}-pyridin-3-yl]-5-methylacetamide-oxazolidin-2-one as a white semi-solid; MS (Cl) [M+H]$^+$ 406.

EXAMPLE 50

(5S)-3-[6-{N-(2-Benzyloxycarbonyl-3-methylbutyryl)piperidinyl-4-oxy}-pyridin-3-yl]-5-methylacetamide-oxazolidin-2-one Compound 50

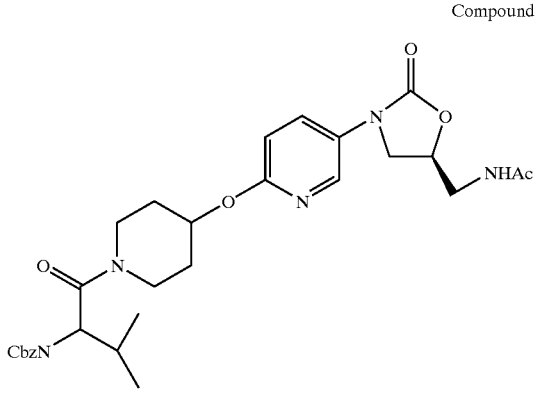

To a solution of 36 mg (0.06 mmol) of the TFA salt from Example 42 in 20 mL CH$_2$Cl$_2$ was added 32 mg (0.13 mmol) Cbz-VAL-OH, 13 mg (0.07 mmol) EDCl, and 35 mg (0.25 mmol) HOBT. The reaction stirred at rt overnight. Then the solution was washed with H$_2$O, extracted with CH$_2$Cl$_2$, washed with sat. NaHCO$_3$, dried with MgSO$_4$ and concentrated to give 10 mg of (5S)-3-[6-{N-(2-Benzyloxycarbonyl-3-methylbutyryl)piperidinyl-4-oxy}-pyridin-3-yl]-5-methylacetamide-oxazolidin-2-one as a clear oil. $^1$H NMR (CDCl$_3$) δ 8.10 (m, 1H); 7.99 (m, 1H); 7.37 (m, 5H); 6.76 (m, 1H); 6.20 (m, 1H); 5.33 (s, 2H); 5.19 (m, 1H); 5.11 (m, 1H); 4.82 (m, 1H); 4.08 (m, 1H); 3.79 (m, 2H); 3.5–3.7 (m, 4H); 3.25 (m, 1H); 2.97 (m, 1H); 2.13 (m, 2H); 2.06 (s, 3H); 1.84 (m, 2H); and 1.30 (s, 6H).

EXAMPLE 51

(S)-N-[[3-[3-Fluoro-4-{N-(2-furoyl)piperdinyl-4-oxy}phenyl]-2-oxo-5-oxazolidinyl]methyl]acetamide Compound 51

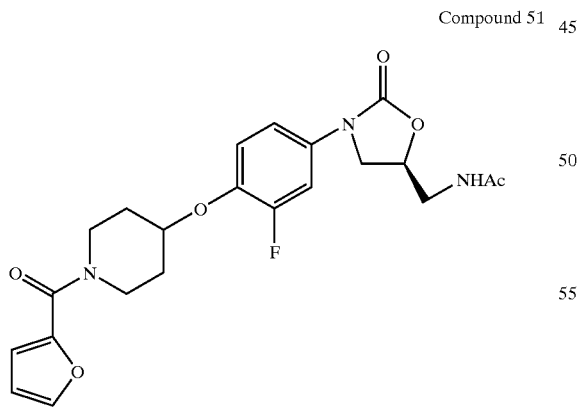

To a solution of 572 mg TFA salt in Example 2 in 50 mL CH$_2$Cl$_2$, was added 5 1.2 mL triethylamine (TEA) and 0.20 mL 2-furanoyl chloride. The reaction was stirred for 18 hours under a nitrogen atmosphere. The reaction was poured into 100 mL water and extracted. The organic layer was dried over MgSO$_4$, filtered and evaporated to an oil. This was triturated with warm ether to afford (S)-N-[[3-[3-fluoro-4-{N-(2-furoyl)piperdinyl-4-oxy}phenyl]-2-oxo-5-oxazolidinyl]methyl]acetamide as a white solid; mp=134–136° C.; MS (Cl) [M+H]$^+$ 446.

EXAMPLE 52

(S)-N-[[3-[3-Fluoro-4-{N-(5-isoxazolylcarbonyl)piperdinyl-4-oxy}phenyl]-2-oxo-5-oxazolidinyl]methyl]acetamide Compound 52

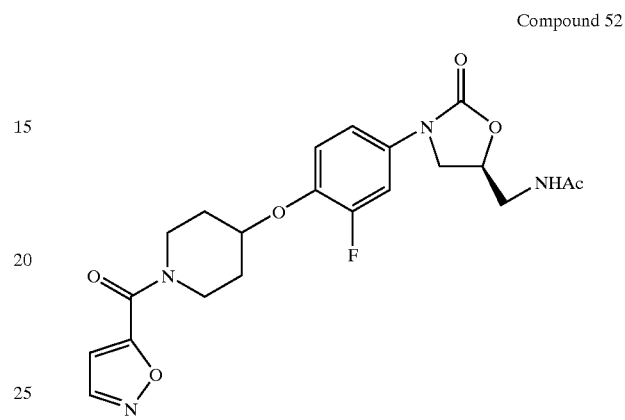

To 433 mg (3.83 mmoles) of 5-isoxazole carboxylic acid in 10 mL CH$_2$Cl$_2$, was added 1 drop of DMF followed by 2 mL oxalyl chloride (2M in CH$_2$Cl$_2$; 4 mmoles). After stirring for 0.5 hour, a solution of 895 mg (1.92 mmoles) TFA salt in Example 2 and 1 mL of TEA in 5 mL CH$_2$Cl$_2$ was added. The reaction was dried over MgSO$_4$, filtered and evaporated. This was purified by column chromatography with 5% MeOH/CH$_2$Cl$_2$ as the eluant to afford (S)-N-[[3-[3-fluoro-4-{N-(5-isoxazolylcarbonyl)piperdinyl-4-oxy}phenyl]-2-oxo-5-oxazolidinyl]methyl]acetamide as a white foam. $^1$H NMR (CDCl$_3$) δ 8.31 (d, J=1.8 Hz, 1H), 7.49 (dd, J=12.9, 2.6 Hz, 1H), 7.08–7.12 (m, 1H), 7.01 (t, J=8.8 Hz, 1H), 6.77 (d, J=1.8 Hz, 1H), 6.04 (t, J=6.0 Hz, 1H), 4.73–4.81 (m, 1H), 4.52–4.57 (m, 1H), 4.03 (t, J=9.0 Hz, 1H), 3.56–3.95 (m, 7H), 2.03 (s, 3H), 1.75–2.00 (M, 4H). MS (Cl) [M+H]$^+$ 447.

EXAMPLE 53

(S)-N-[[3-[3-Fluoro-4-{N-(acetoxyacetyl)piperidinyl-4-oxy}phenyl]-2-oxo-5-oxazolidinyl]methyl]acetamide Compound 53

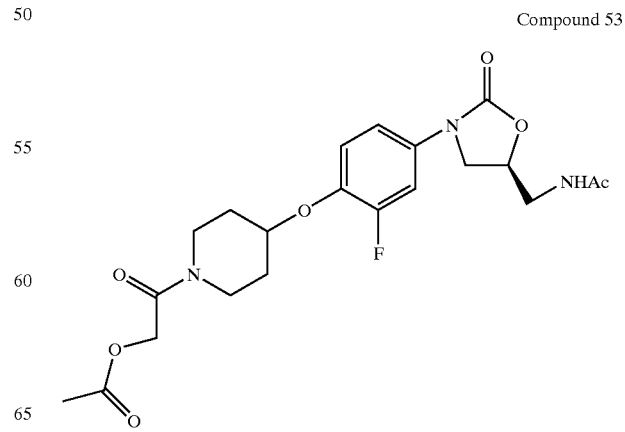

To 2.12 g (4.55 mmol) of TFA salt of Example 2 in 150 mL $CH_2Cl_2$, was added 5 mL TEA. After stirring for 15 min, 0.62 (5.76 mmol) acetoxyacetyl chloride was added and the reaction stirred for 2.5 h. The volatiles were evaporated and the residue chromatographed using 10% $MeOH/CH_2Cl_2$ as the eluant. (S)-N-[[3-[3-Fluoro-4-{N-(acetoxyacetyl) piperidinyl-4-oxy}phenyl]-2-oxo-5-oxazolidinyl]methyl] acetamide was isolated as a pale beige solid; mp=146–20 147.5° C., MS (Cl) $[M+H]^+$ 452.

EXAMPLE 54

(S)-N-[[3-[4-{N-(Pyridin-4-ylmethoxyacetyl) piperidinyl-4-oxy}phenyl]-2-oxo-5-oxazolidinyl] methyl]acetamide Compound 54

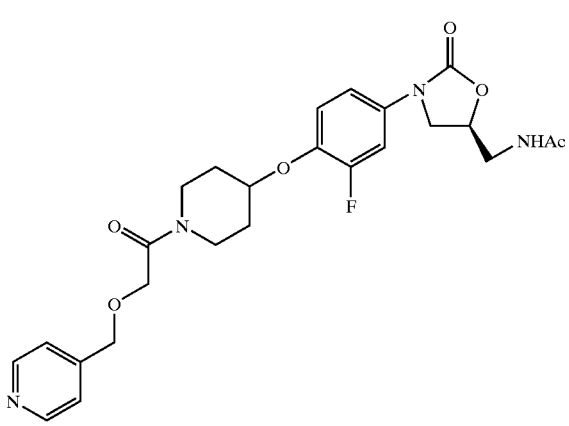

(S)-N-[[3-[4-{N-(Chloroacetyl)piperidinyl-4-oxy}phenyl]-2-oxo-5-5 oxazolidinyl]methylacetamide A solution of 4.19 g (9.00 mmol) of TFA salt of Example 2 and 3 mL of TEA in 125 mL $CH_2Cl_2$ was added dropwise to 0.75 mL of chloroacetylchloride (9.42 mmol) in 100 mL $CH_2Cl_2$. After stirring at room temperature for 2 h, the reaction was poured into 300 mL water and extracted. The organic layer was dried over $MgSO_4$, filtered and evaporated to give (S)-N-[[3-[4-{N-(Chloroacetyl)piperidinyl-4-oxy}phenyl]-2-oxo-5-oxazolidinyl]methylacetamide as a viscous oil.

(S)-N-[[3-[4-{N-(Pyridin-4-ylmethoxyacetyl)piperidinyl-4-oxy}phenyl]-2-oxo-5-oxazolidinyl]methylacetamide (Compound 54):

To 101.1 mg NaH (60% in oil; 2.53 mmol) in 5 mL anh THF at 0° C., was added dropwise 265 mg (2.43 mmol) pyridine-4-methanol in 5 mL anh THF. After stirring for 15 min, 503 mg (1.18 mmol) (S)-N-[[3-[4-{N-(chloroacetyl) piperidinyl-4-oxy}phenyl]-2-oxo-5-oxazolidinyl]-methylacetamide in 5 mL anh THF was added. The reaction was stirred at room temperature for 16 h, and then poured into 125 mL water. This was extracted with 3×100 mL $CH_2Cl_2$. The combined organic layers were dried over $MgSO_4$, filtered and evaporated. Pure (S)-N-[[3-[4-{N-(pyridin-4-ylmethoxyacetyl)piperidinyl-4-oxy}phenyl]-2-oxo-5-oxazolidinyl]methylacetamide, obtained by chromatography using 5% $MeOH/CH_2Cl_2$, was isolated as a white foam. $^1H$ NMR (CDCl$_3$) δ 8.59 (d, J=5.9 Hz, 2H), 7.47 (dd, J=12.9, 2.6 Hz, 1H), 7.28 (d, J=5.9 Hz, 2H), 7.07–7.11 (m, 1H), 6.99 (t, J=8.8 Hz, 1H), 5.91–5.94 (m, 1H), 4.72–4.79 (m, 1H), 4.65 (s, 2H), 4.45–4.49 (m, 1H), 4.26 (s, 2H), 4.02 (t, J=8.9 Hz, 1H), 3.40–3.78 (m, 7H), 2.02 (s, 3H) 1.85–1.95 (m, 4H). MS (Cl) $[M+H]^+$ 501.

EXAMPLE 55

(S)-N-[[3-[4-{N-(Pyridin-3-ylmethoxyacetyl) piperidinyl-4-oxy}phenyl]-2-oxo-5-oxazolidinyl] methylacetamide Compound 55

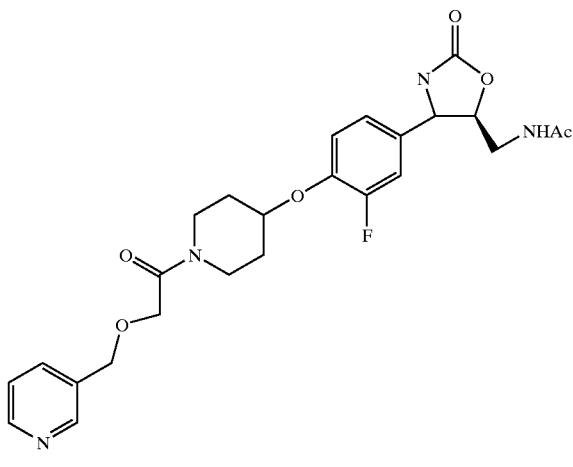

To 117 mg NaH (60% in oil; 2.93 mmol) in 5 mL anh THF at 0° C., was added dropwise 0.24 mL (2.47 mmol) pyridine-3-methanol in 5 mLTHF. After stirring for 15 minutes, 523 mg (1.22 mmol) chloroacetamide from Example 54 in 5 mL anh THF was added in one portion. The reaction was warmed to room temperature and stirred for 72 hours. The reaction was poured into 50 mL water and extracted 3×75 mL $CH_2Cl_2$. The combined organic layers were dried over $MgSO_4$, filtered and evaporated. Chromatography with 3% $MeOH/CH_2Cl_2$ afforded (S)-N-[[3-[4-{N-(pyridin-3-ylmethoxyacetyl)piperidinyl-4-oxy}phenyl]-2-oxo-5-oxazolidinyl]methylacetamide as a clear glass. $^1H$ NMR (CDCl$_3$) δ 8.56–8.60 (m, 2H), 7.73 (d, J=7.8 Hz, 1H), 7.47 (dd, J=13.0, 2.6 Hz, 1H), 7.30 (dd, J=7.8, 5.1 Hz, 1H), 7.08 (dd, J=8.9, 1.6 Hz, 1H), 6.99 (t, J=8.9 Hz, 1H), 6.02 (t, J=6.2 Hz, 1H), 4.70–4.78 (m, 1H), 4.64 (s, 2H), 4.43–4.47 (m, 1H), 4.24 (s, 2H), 4.02 (t, J=8.9 Hz, 1H), 3.57–3.78 (m, 6H), 3.35–3.45 (m, 1H), 2.02 (s, 3H), 1.80–1.96 (m, 4H). MS (Cl) $[M+H]^+$ 501.

EXAMPLE 56

(S)-N-[[3-[4-{N-(Morpholinoacetyl)piperidinyl-4-oxy}phenyl]-2-oxo-5-oxazolidinyl]methylacetamide Compound 56

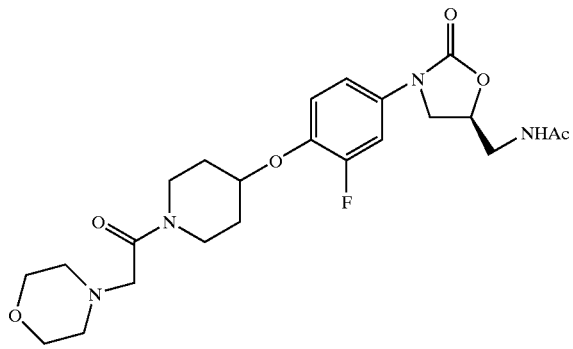

To 415 mg (0.97 mmol) of chloroacetamide from Example 54 in 15 mL THF, was added 0.25 mL (2.87 mmol) morpholine. The reaction was stirred for 72 hours at room temperature, poured into 50 mL water and extracted 3×50 mL CH$_2$Cl$_2$. The combined organic layers were washed with water, dried over MgSO$_4$, filtered and evaporated. (S)-N-[[3-[4-{N-Morpholinoacetyl)-piperidinyl-4-oxy}phenyl]-2-oxo-5-oxazolidinyl]methylacetamide was obtained as a clear glass after chromatography (3% MeOH/CH$_2$Cl$_2$). $^1$H NMR (CDCl$_3$) δ 7.47 (dd, J=13.0, 2.6 Hz, 1H), 7.07–7.11 (m, 1H), 7.00 (t, J=8.8 Hz, 1H), 5.93 (brt, J=6.1 Hz, 1H), 4.73–4.79 (m, 1H), 4.44–4.78 (m, 1H), 4.02 (t, J=9.0 Hz, 1H), 3.51–3.85 (m, 11H), 3.20 (s, 2H), 2.47–2.51 (m, 4H), 2.03 (s, 3H), 1.81–1.96 (m, 4H). MS (Cl) [M+H]$^+$ 479.

EXAMPLE 57

(S)-N-[[3-[3-Fluoro-4-{N-(methanesulfonyl)azetidinyl-3-oxy}phenyl]-2-oxo-5-oxazolidinyl]methyl]acetamide Compound 57

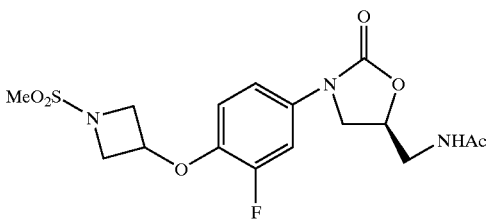

1-[N-(Diphenylmethyl)azetidinyl-3-oxy]-2-fluoro-4-nitrobenzene:

To 5.40 g (22.56 mmol) N-(diphenylmethyl)azetidin-4-ol in 200 mL THF at 0° C., was added 30 mL KOtBu (1M in THF; 30 mmol). After stirring for 0.5 h, 2.5 mL (22.58 mmol) 3,4-difluoronitrobenzene was added. The reaction was warmed to room temperature and stirred for 18 h. After evaporation of the THF, the residue was partitioned between 300 mL water and 250 mL CH$_2$Cl$_2$. The aqueous was washed with additional CH$_2$Cl$_2$. The combined organic layers were dried over MgSO$_4$, filtered and evaporated. Chromatography with 15% EtOAc/hexanes afforded pure 1-[N-(Diphenylmethyl)azetidinyl-4-oxy]-2-fluoro-4-nitrobenzene as a viscous gold oil. $^1$H NMR (CDCl$_3$) δ 7.96–8.01 (m, 2H), 7.16–7.47 (m, 10H), 6.72–6.80 (m, 1H), 4.88–5.00 (m, 1H), 4.94 (s, 1H), 3.70–3.81 (m, 2H), 3.17–3.27 (m, 2H). MS (Cl) [M+H]$^+$ 379.

1-[N-(Diphenylmethyl)azetidinyl-3-oxy]-2-fluoro-4-aminobenzene:

7.55 g (19.95 mmol) 1-[N-(diphenylmethyl)azetidinyl-4-oxy]-2-fluoro-4-nitrobenzene, 7.31 g (116 mmol) ammonium formate, and approximately 250 mg 10% Pd/C in 500 mL MeOH were heated at reflux for 21 h. After cooling, the reaction was filtered through a pad of Celite and the methanol evaporated to afford crude 1-[N-(diphenylmethyl)azetidinyl-4-oxy]-2-fluoro-4-aminobenzene as a mustard yellow semisolid. $^1$H NMR (CDCl$_3$) δ 7.13–7.48 (m, 1OH), 6.57 (t, J=8.8 Hz, 1H), 6.43 (dd, J=12.9, 2.6 Hz, 1H), 6.23–6.30 (m, 1H), 4.67–4.80 (m, 1H), 4.52 (s, 1H), 4.00 (brs, 2H), 3.73–3.85 (m, 2H), 3.13–3.23 (m, 2H). MS (Cl) [M+H]$^+$ 349.

2-Fluoro-1-{N-(diphenylmethyl)azetidinyl-3-oxy}-4-(benzyloxycarbonylamino)benzene:

Crude aniline (6.19 g; 17.77 mmol) in 750 mL of acetone/water (2:1) was cooled to 0° C. 3.34 g (39.76 mmol) sodium bicarbonate was added followed by 3.3 mL (23.39 mmol) benzylchloroformate. The reaction was stirred at room temperature for 20 h and the volatiles were evaporated. The aqueous residue was extracted 3×250 mL EtOAc. The combined organic layers were dried over MgSO$_4$, filtered and evaporated. Chromatography with 50% EtOAc/hexanes afforded pure 2-fluoro-1-{N-(diphenylmethyl)azetidinyl-3-oxy}-4-(benzyloxycarbonylamino)benzene as a white solid; mp=128–131° C.; MS (Cl) [M+H]$^+$ 483.

(R)-[3-[3-Fluoro-4-{N-(diphenylmethyl)azetidinyl-3-oxy}phenyl]-2-oxo-5-oxazolidinyl]methanol:

To 2.13 g (4.41 mmol) of 2-fluoro-1-{N-(diphenylmethyl)azetidinyl-3-oxy}-4-(benzyloxycarbonylamino)benzene in 75 mL of THF at –78° C. under a nitrogen atmosphere, was added 2.5 mL nBuLi (2.5 M in hexanes; 6.25 mmol). The reaction was stirred for 0.5 h and then 0.65 mL of (R)-glycidyl butyrate (4.59 mmol) was added. The reaction was stirred at room temperature overnight, poured into 75 mL of saturated ammonium chloride (aq) and extracted 3×100 mL EtOAc. The combined organic layers were washed with water, dried over MgSO$_4$, filtered and evaporated. Chromatography with 60% EtOAc/hexanes afforded (R)-[3-[3-Fluoro-4-{N-(diphenylmethyl)azetidinyl-3-oxy}phenyl]-2-oxo-5-oxazolidinyl]methanol as an off-white foam. $^1$H NMR (CDCl$_3$) δ 7.17–7.51 (m, 11 H), 7.03 (d, J=8.9 Hz, 1H), 6.70 (t, J=8.9 Hz, 1H), 4.70–4.90 (m, 2H), 4.44 (s, 1H), 3.87–4.13 (m, 3H), 3.68–3.76 (m, 3H), 3.13–3.18 (m, 2H), 2.05 (brt, 1H). MS (Cl) [M+H]$^+$ 449.

(S)-[3-[3-Fluoro-4-{N-(diphenylmethyl)azetidinyl-3-oxy}phenyl]-2-oxo-5-oxazolidinyl]methyl Azide:

To 1.40 g (3.12 mmol) of (R)-[3-[3-fluoro-4-{N-(diphenylmethyl)-azetidinyl-3-oxy}phenyl]-2-oxo-5-oxazolidinyl]methanol and 0.90 mL (6.46 mmol) TEA in 90 mL CH$_2$Cl$_2$ at 0° C. under a nitrogen atmosphere, was added 0.3 mL (3.87 mmol) methanesulfonyl chloride. After stirring for 1.5 h, the reaction was poured into 150 mL water and extracted. The aqueous layer was washed with an additional portion of CH$_2$Cl$_2$. The combined organic layers were dried over MgSO$_4$, filtered and evaporated to give crude mesylate. MS (Cl) [M+H]$^+$ 527. This mesylate (3.08 mmol) and 0.80 g (12.31 mmol) sodium azide in 75 mL DMF were heated at 70° C. for 2.5 hours under a nitrogen atmosphere. After cooling, the reaction was poured into 400 mL water and extracted 3×150 mL EtOAc. The combined organic layers were washed with several portions of water, dried over MgSO$_4$, filtered and evaporated to yield (R)-[3-[3-fluoro-4-{N-(diphenylmethyl)azetidinyl-3-oxy}phenyl]-2-oxo-5-oxazolidinyl]methyl azide as a semi-solid. $^1$H NMR (CDCl$_3$) δ 7.19–7.50 (m, 11H), 7.05 (d, J=9.0 Hz, 1H), 6.74 (t, J=9.0 Hz, 1H), 4.71–4.87 (m, 2H), 4.46 (s, 1H), 4.03 (t, J=8.8 Hz, 1H), 3.50–3.88 (m, 5H), 3.10–3.21 (m, 2MS [M+H]$^+$ 474.

(S)-[3-[3-Fluoro-4-{N-(diphenylmethyl)azetidinyl-3-oxy}phenyl]-2-oxo-5-oxazolidinyl]methylacetamide:

1.13 g (2.39 mmol) (R)-[3-[3-Fluoro-4-{N-(diphenylmethyl)azetidinyl-3-oxy}phenyl]-2-oxo-5-oxazolidinyl]methyl azide and 0.85 g (3.24 mmol) triphenylphosphine in 60 mL THF were stirred at room temperature under a nitrogen atmosphere overnight. 3.0 mL water was added and the reaction heated at 70° C. for 6 h. The volatiles were evaporated and the remaining water azeotroped with several portions of benzene to give a mixture of crude amine and triphenylphosphine oxide. MS (Cl) [M+H]$^+$ 448. The crude amine, 0.3 mL (3.17 mmol) acetic anhydride and 0.6 mL (7.42 mmol) pyridine in 75 mL EtOAc were stirred at room temperature under a nitrogen atmosphere overnight. The reaction was extracted with 100 mL water. The organic layer was dried over MgSO$_4$, filtered and evaporated. Chromatography with 2% MeOH/CH$_2$Cl$_2$ afforded (S)-[3-[3-Fluoro-4-{N-(diphenylmethyl)azetidinyl-3-oxy}phenyl]-2-oxo-5-oxazolidinyl]methylacetamide as a white foam. $^1$H NMR (CDCl$_3$) δ 7.13–7.50 (m, 11 H), 6.92–7.03 (m, 1H), 6.70 (t, J=8.9 Hz, 1H), 5.96 (br s, 1H), 4.68–4.85 (m2H), 4.45 (s, 1H), 3.97 (t, J=9.0 Hz, 1H), 3.50–3.76 (m, 5H), 3.10–3.19 (m, 2H), 2.03 (s, 3H). MS (Cl) [M+H]$^+$ 490.

(S)-N-[[3-[3-Fluoro-4-{N-(methanesulfonyl)azetidinyl-3-oxy}phenyl]-2-oxo-5-oxazolidinyl]methyl]acetamide (Compound 57):

To 160 mg (0.327 mmol) (S)-[3-[3-fluoro-4-{N-(diphenylmethyl)azetidinyl-3-oxy}phenyl]-2-oxo-5-oxazolidinyl]methylacetamide in 5 mL 1,2-dichloroethane, was added 0.04 mL (0.371 mmol) α-chloroethylchloroformate. The reaction was heated at 70° C. for 5 h. Ten mL MeOH was added and reflux continued overnight.

The volatiles were evaporated to afford the crude hydrochloride salt of the deprotected amine. This was suspended in 20 mL CH$_2$Cl$_2$ and 0.15 mL (1.07 mmol) TEA was added followed by 0.1 mL (1.29 mmol) methanesulfonyl chloride. The reaction was stirred overnight, poured into 100 mL water and extracted. The organic layer was washed with 1N HCl (aq), dried over MgSO$_4$, filtered and evaporated. Chromatography with 3% MeOH/CH$_2$Cl$_2$ afforded (S)-N-[[3-[3-fluoro-4-{N-(methanesulfonyl)azetidinyl-3-oxy}phenyl]-2-oxo-5-oxazolidinyl]methyl]acetamide as a white foam. $^1$H NMR (CDCl$_3$) δ 7.52 (dd, J=13.1, 2.7 Hz, 1H), 7.06–7.10 (m, 1H), 6.76 (t, J=8.9 Hz, 1H), 5.91 (brt, 1H 4.87–4.95 (m, 1H), 4.72–4.81 (m, 1H), 4.28 (dd, J=9.7, 6.4 Hz, 2H), 4.09 (dd, J=9.7, 4.8 Hz, 2H), 4.01 (t, J=8.9 Hz, 1H), 3.56–3.77 (m, 3H), 2.93 (s, 3H), 2.02 (s, 3H). MS (Cl) [M+H]$^+$ 402.

EXAMPLE 58

(S)-N-[[3-[3-Fluoro-4-{N-(benzyloxyacetyl)azetidinyl-3-oxy}phenyl]-2-oxo-5-oxazolidinyl]methyl]acetamide Compound 58

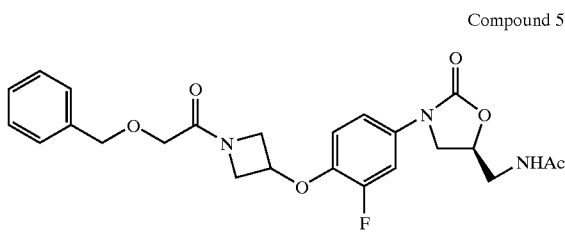

258 mg (0.527 mmol) (S)-[3-[3-fluoro-4-{N-(diphenylmethyl)azetidinyl-3-oxy}phenyl]-2-oxo-5-oxazolidinyl]methylacetamide from Example 57 and 0.20 mL (1.26 mmol) benzyloxyacetyl chloride in 10 mL 1,2-dichloroethane were heated at reflux for 48 h under a nitrogen atmosphere. After cooling, the reaction was diluted with 100 mL CH$_2$Cl$_2$ and extracted with 50 mL 1 N HCl. The organic layer was washed with water, dried over MgSO$_4$, filtered and evaporated. Chromatography with 3% MeOH/CH$_2$Cl$_2$ yielded (S)-N-[[3-[3-Fluoro-4-{N-(benzyloxyacetyl)azetidinyl-3-oxy}phenyl]-2-oxo-5-oxazolidinyl]methyl]acetamide as a white powder; mp=119–121° C.; MS (Cl) [M+H]$^+$ 472.

EXAMPLE 59

(S)-N-[[3-[3-Fluoro-4-{N-(acetoxyacetyl)azetidinyl-3-oxy}phenyl]-2-oxo-5-oxazolidinyl]methyl] acetamide Compound 59

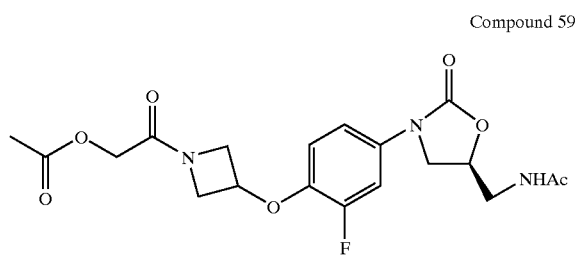

323 mg (0.660 mmol) (S)-[3-[3-fluoro-4-{N-(diphenylmethyl)azetidinyl-3-oxy}phenyl]-2-oxo-5-oxazolidinyl]methylacetamide from Example 57 and 0.2 mL (1.86 mmol) acetoxyacetyl chloride in 15 mL 1,2-dichloroethane were heated at reflux for 24 h. After cooling, the volatiles were evaporated and the residue chromatographed with 3% MeOH/CH$_2$Cl$_2$. (S)-N-[[3-[3-Fluoro-4-{N-(acetoxyacetyl)azetidinyl-3-oxy}phenyl]-2-oxo-5-oxazolidinyl]methyl]-acetamide was isolated as a white solid; mp=172–175° C.; MS (Cl) [M+H]$^+$ 424.

EXAMPLE 60

(S)-N-[[3-[3-Fluoro-4-{N-(acetoxyacetyl)azetidinyl-3-oxy}phenyl]-2-oxo-5-oxazolidinyl]methyl]-N-[α-acetoxyacetyl]acetamide Compound 60

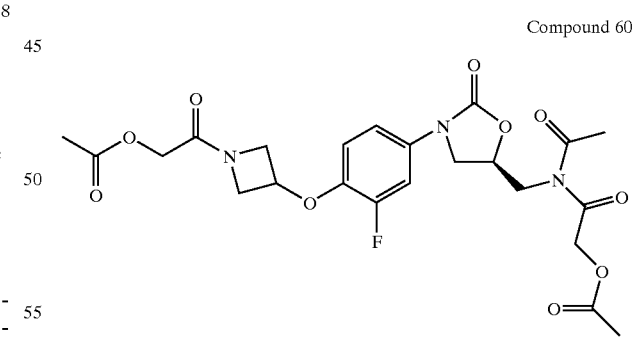

This was also isolated (as a white foam) from the reaction mixture in Example 59. $^1$H NMR (CDCl$_3$) δ 7.53 (dd, J=13.0, 2.8 Hz, 1H), 7.04–7.10 (m, 1H), 6.78 (t, J=8.8 Hz, 1H), 4.95–5.18 (m, 3H), 4.75–4.89 (m, 1H), 4.30–4.68 (m, 5H), 4.00–4.30 (m, 3H), 3.83–3.91 (m, 1H), 3.68–3.79 (m, 1H), 2.47 (s, 3H), 2.02 (s, 3H), 2.18 (s, 3H). MS (Cl) [M+Na]$^+$ 546.

EXAMPLE 61

(S)-N-[[3-[3-Fluoro-4-{N-((α-hydroxyacetyl )azetidinyl-3-oxy}phenyl]-2-oxo-5-oxazolidinyl] methyl]acetamide Compound 61

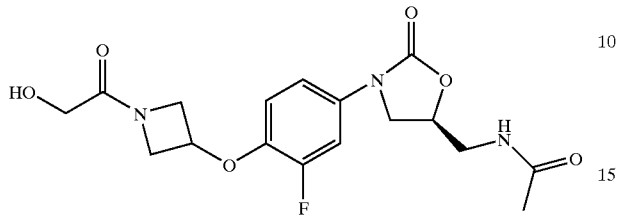

150 mg (0.354mmol) (S)-N-[[3-[3-Fluoro-4-{N-(acetoxyacetyl)azetidinyl-3-oxy}phenyl]-2-oxo-5-oxazolidinyl]methyl]acetamide from Example 59 and 55 mg potassium carbonate in 30 mL MeOH were stirred at room temperature for 20 minutes under a nitrogen atmosphere. The volatiles were evaporated and the sample dissolved in 50 mL CH$_2$Cl$_2$. This was washed with 50 mL water, dried over MgSO$_4$, filtered and evaporated to afford (S)-N-[[3-[3-fluoro-4-{N-(α-hydroxyacetyl)azetidinyl-3-oxy}phenyl]-2-oxo-5-oxazolidinyl]methyl]acetamide as a white solid, mp=158–160° C.; $^1$H NMR (MeOH-d$_4$) δ 7.57 (dd, J=13.3, 2.6 Hz, 1H), 7.15–7.18 (m, 1H), 6.91 (t, J=9.0 Hz, 1H), 5.04–5.12 (m, 1H), 4.66–4.80 (m, 2H), 4.44 (dd, J=10.6, 6.7 Hz, 1H), 4.27–4.34 (m, 1H), 4.01–4.11 (m, 4H), 3.78 (dd, J=9.2, 6.4 Hz, 1H), 3.55 (d, J=5.0 Hz, 2H), 1.96 (s, 3H). MS (Cl) [M+H]$^+$ 382.

The invention has been described in detail with particular reference to the above embodiments thereof. The above embodiments and examples are given to illustrate the scope and spirit of the present invention. These embodiments and examples will make apparent, to those skilled in the art, other embodiments and examples. These other embodiments and examples are within the contemplation of the present invention. It will be understood that variations and modifications can be effected within the spirit and scope of the invention; therefore, the instant invention should be limited only by the appended claims.

We claim:

1. A compound of Formula I

Formula I

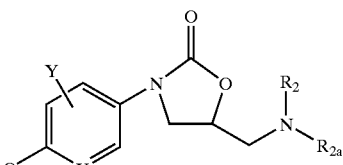

wherein

R$_1$ is selected from 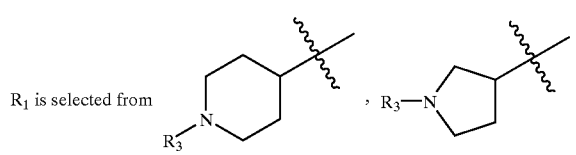

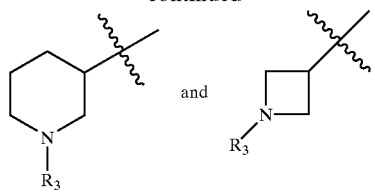

and wherein (a) R$_3$ is selected from H, alkyl, —COR$_4$, —(CH$_2$)$_t$heteroaryl, —CHR$_5$R$_6$, —(CH$_2$)$_t$aryl, —SO$_2$NR$_5$R$_6$, and —SO$_2$R$_9$;

(b) R$_4$ is selected from H, —OR$_5$, alkyl, alkylaryl, —(CH$_2$)$_t$aryl, —(CH$_2$)$_t$heteroaryl, —(CH$_2$)$_t$OR$_5$, —(CH$_2$)$_t$NR$_7$R$_8$, —CHR$_5$R$_6$, and —NR$_5$R$_6$ optionally forming a cyclic amino derivative;

(c) R$_5$ and R$_6$ are independently selected from H, alkyl, alkylaryl, haloaryl, —(CH$_2$)$_t$aryl, —(CH$_2$)$_t$heteroaryl, and acyl;

(d) R$_7$ and R$_8$ are independently selected from H, alkyl, —COR$_9$, —SO$_2$R$_9$ and —CO$_2$R$_9$; and (e) R$_9$ is selected from H, alkyl, aryl and alkylaryl;

R$_2$ is selected from C(O)RG and C(O)OR$_9$,

R$_{2a}$ is H or acyl with the proviso that when R$_3$ is selected from alkyl, —(CH$_2$)$_t$aryl, —(CH$_2$)$_t$heteroaryl, and —CHR$_5$R$_6$, R$_{2a}$ is H;

X is N or CH;

Y is selected from H, halogen, alkoxy, and alkyl; and t is an integer of 0 to 4;

or an optical isomer, enantiomer, diastereomer, racemate or racemic mixture thereof, or a pharmaceutically acceptable salt thereof.

2. The compound of claim 1 wherein X is CH.

3. The compound of claim 1 wherein R$_2$ is —C(O)R$_9$ wherein R$_9$ is as claimed in claim 1.

4. The compound of claim 3 wherein R$_9$ is H or alkyl.

5. The compound of claim 1 wherein R$_1$ is

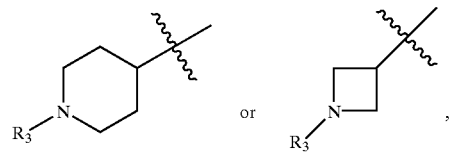

wherein R$_3$ is as claimed in claim 1.

6. The compound of claim 5 wherein R$_{2a}$ is H and R$_3$ is selected from —COR$_4$, —SO$_2$R$_9$ and —(CH$_2$)$_t$heteroaryl wherein R$_4$, R$_9$ and t are as claimed in claim 1.

7. The compound of claim 5 wherein R$_4$ is selected from —OR$_5$, —(CH$_2$)$_t$OR$_5$, alkyl, —(CH$_2$)$_t$aryl, and —(CH$_2$)$_t$heteroaryl wherein R$_5$ and t are as claimed in claim 1.

8. The compound of claim 7 wherein R$_5$ is alkyl and R$_9$ is H or alkyl.

9. A compound of claim 1 or a pharmaceutically acceptable salt thereof, which is (S)-N-[[3-[3-fluoro-4-{N-(benzyloxyacetyl)piperidinyl-4-oxy}phenyl]-2-oxo-5-oxazolidinyl]methyl]acetamide.

10. A compound of claim 1 or a pharmaceutically acceptable salt thereof, which is (S)-N-[[3-[3-fluoro-4-{N-(α-hydroxyacetyl)piperidinyl-4-oxy}phenyl]-2-oxo-5-oxazolidinyl]methyl]acetamide.

11. A compound of claim 1 or a pharmaceutically acceptable salt thereof, which is (S)-N-[[3-[3-fluoro-4-{N-

(methanesulfonyl)piperidinyl-4-oxy}phenyl]-2-oxo-5-oxazolidinyl]methyl]acetamide.

12. A compound of claim 1 or a pharmaceutically acceptable salt thereof, which is (S)-N-[[3-[3-fluoro-4-{N-(methoxycarbonyl)piperidinyl-4-oxy}phenyl]-2-oxo-5-oxazolidinyl]methyl]acetamide.

13. A compound of claim 1 or a pharmaceutically acceptable salt thereof, which is (S)-N-[[3-[3-fluoro-4-{N-(2-pyrimidinyl)piperidinyl-4-oxy}phenyl]-2-oxo-5-oxazolidinyl]methyl]acetamide.

14. A compound of claim 1 or a pharmaceutically acceptable salt thereof, which is (S)-N-[[3-[3-fluoro-4-{N-(3-cyanobenzoyl)piperidinyl-4-oxy}phenyl]-2-oxo-5-oxazolidinyl]methyl]acetamide.

15. A compound of claim 1 of a pharmaceutically acceptable salt thereof, which is (S)-N-[[3-[3-fluoro-4-{N-(5-cyano-2-pyridyl)piperidinyl-4-oxy}phenyl]-2-oxo-5-oxazolidinyl]methyl]acetamide.

16. A compound of claim 1 or a pharmaceutically acceptable salt thereof, which is (S)-N-[[3-[3-fluoro-4-{N-(2-thienylcarbonyl)piperidinyl-4-oxy}phenyl]-2-oxo-5-oxazolidinyl]methyl]acetamide.

17. A compound of claim 1 or a pharmaceutically acceptable salt thereof, which is (S)-N-[[3-[3-fluoro-4-{N-(α-hydroxyacetyl)piperidinyl-3-oxy}phenyl]-2-oxo-5-oxazolidinyl]methyl]acetamide.

18. A compound of claim 1 or a pharmaceutically acceptable salt thereof, which is (S)-N-[[3-[3-Fluoro-4-{N-(benzyloxyacetyl)pyrrolidinyl-3-oxy}phenyl]-2-oxo-5-oxazolidinyl]methyl]acetamide.

19. A pharmaceutical composition comprising a compound of claim 1 and a pharmaceutically acceptable carrier.

20. A method of treating a subject having a condition caused by or contributed to by bacterial infection, which comprises administering to said subject a therapeutically effective amount of the compound of Formula I as defined in claim 1.

21. A method of preventing a subject from suffering from a condition caused by or contributed to by bacterial infection, which comprises administering to the subject a prophylactically effective amount of the compound of Formula I as defined in claim 1.

22. The method of claim 20 or 21 wherein said condition is selected from community-acquired pneumonia, upper and lower respiratory tract infections, skin and soft tissue infections, bone and joint infections, and hospital-acquired lung infections.

23. The method of claim 20 or 21 wherein said bacterium is selected from *S. aureus, S. epidermidis, S. pneumoniae,* Enterococcus spp., *Moraxella catarrhalis* and *H. influenzae.*

24. The method of claim 20 or 21 wherein said bacterium is a Gram-positive coccus.

25. The method of claim 24 wherein said Gram-positive coccus is antibiotic-resistant.

\* \* \* \* \*